United States Patent
Link, Jr. et al.

(10) Patent No.: US 6,541,197 B2
(45) Date of Patent: *Apr. 1, 2003

(54) VEHICLES FOR STABLE TRANSFER OF GREEN FLUORESCENT PROTEIN GENE AND METHODS OF USE FOR SAME

(75) Inventors: Charles J. Link, Jr., Des Moines, IA (US); John P. Levy, West Des Moines, IA (US); Suming Wang, Des Moines, IA (US); Tatiana Seregina, West Des Moines, IA (US)

(73) Assignee: Human Gene Therapy Research Institute, Des Moines, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/786,531

(22) Filed: Jan. 21, 1997

(65) Prior Publication Data

US 2002/0015979 A1 Feb. 7, 2002

Related U.S. Application Data

(60) Provisional application No. 60/010,371, filed on Jan. 22, 1996.

(51) Int. Cl.$^7$ ............................. C12Q 1/70; C12Q 1/68; C12N 15/86; C12N 5/10
(52) U.S. Cl. ................ 435/5; 435/4; 435/6; 435/320.1; 435/325; 435/350; 435/351; 435/352; 435/366
(58) Field of Search ............................... 435/69.1, 69.7, 435/252.3, 320.1, 189, 70.3, 70.4, 4–6, 325, 350–352, 366; 536/24.1, 23.5, 24.2, 23.4

(56) References Cited

U.S. PATENT DOCUMENTS 5,681,562 A * 10/1997 Sobol et al. ............. 424/93.21
5,874,304 A *  2/1999 Zolotukhin et al. ......... 435/366

FOREIGN PATENT DOCUMENTS

WO      WO 95/21191       8/1995

OTHER PUBLICATIONS

Clontech catalog (1996) Catalog #6088–1, sequence and restriction information, phGFP–S65T humanized vector.*
Grantham et al. (1980) Nucleic acid research 8, pp. 49–62.*
Rosenberg et al. (1990) The New England J. Med. 323, pp. 570–578.*
Miller et al. (1993) Meth. Enzymol. 217, pp. 581–599.*
Heim et al. (1995) Nature 373, pp. 663–664.*
Cormack et al. (1996) Gene 173, pp. 33–38.*
Kasahara, N, Nov. 1994, "Tissue–Specific Targeting of Retroviral Vectors Through Ligand–Receptor Interactions", Science, 266(25) 1373–1376.
Barinaga, M, "Step Taken Toward Improved Vectors for Gene Transfer", Science, 266(25) 1326 (1994).
Somia, N, "Generation of Targeted Retroviral Vectors by Using Single–Chain Variable Fragment: An Approach to in vivo Gene Delivery", Proc. Natl. Acad. Sci. USA, 92:7570–7574, Aug. 1995.
Cody, C., "Chemical Structure of Hexapeptide Chromophore of the Aequorea Green–Fluorescent Protein", Biochemistry, 1993, 32:1212–1218.
Inouye, S., "Aequorea Green Fluorescent Protein Expression of the Gene and Fluorescence Characteristics of the Recombinant Protein", FEBS Lett. 341 (1994) 277–280.
Prasher, D., (1992) "Primary Structure of the Aequorea victoria Green–Fluorescent Protein", Gene, 111:229–233, Elsevier Science Publishers.
Perozzo, M., "X–Ray Diffraction and Time–Resolved Fluorescence Analyses of Aequorea Green Fluorescent Protein Crystals", The J. of Biological Chemistry, 263(16) 7713–7716 (1988).
Ward, W., "Reversible Denaturation of Aequorea Green–Fluorescent Protein: Physical Separation and Characterization of the Renatured Protein", Biochemistry, 21(19) 4535–4540 (1982).
Deschamps, J., "Rapid Purification of Recombinant Green Fluorescent Protein Using the Hydrophobic Properties of an HPLC Size–Exclusion Column", Protein Expression and Purification 6:555–558 (1985).
Prasher, D., "Using GFP to See the Light", TIG 11(8) 320–323 (1995).
Chalfie, M., "Green Fluorescent Protein as a Marker for Gene Expression", Science, 263:802–805.

* cited by examiner

Primary Examiner—Elizabeth Slobodyansky
(74) Attorney, Agent, or Firm—McKee, Voorhees & Sease, P.L.C.

(57) ABSTRACT

The present invention describes an efficient retroviral or viral based method that allows easy and quick identification of gene transfer in living, transduced mammalian cells. Retroviral and viral vector producer cells were generated containing a gene for an improved humanized red-shifted, Green Fluorescent Protein (hRGFP) which increases the resulting fluorescence yield after excitation. This humanized, red-shifted GFP (hRGFP) gene was cloned into several vectors and transfected into various packaging cell lines to produce vibrant green fluorescence after excitation with blue light at 450–490 nm. These vectors represent a substantial advance over currently available gene transfer marking systems or wild-type GFP marker systems none of which have been stably transfected into cells.

5 Claims, 55 Drawing Sheets

(8 of 55 Drawing Sheet(s) Filed in Color)

pLEL pLEL is a retroviral plasmid expressing the enhanced GFP gene driven by the LTR promoter.

```
  1 gaattgctag caattgctag caattgctag caattcatac cagatcaccg aaaactgtcc
 61 tccaaatgtg tcccctcac actcccaaat tcgcgggctt ctgcctctta gaccactcta
121 ccctattccc cacactcacc ggagccaaag ccgcggccct tccgtttctt tgcttttgaa
181 agaccccacc cgtaggtggc aagctagctt aagtaacgcc actttgcaag gcatggaaaa
241 atacataact gagaatagaa aagttcagat caaggtcagg aacaaagaaa cagctgaata
301 ccaaacagga tatctgtggt aagcggttcc tgccccggct cagggccaag aacagatgag
361 acagctgagt gatgggccaa acaggatatc tgtggtaagc agttcctgcc ccggctcggg
421 gccaagaaca gatggtcccc agatgcggtc cagccctcag cagtttctag tgaatcatca
481 gatgttccca gggtgcccca aggacctgaa aatgaccctg taccttattt gaactaacca
541 atcagttcgc ttctcgcttc tgttcgcgcg cttccgctct ccgagctcaa taaaagagcc
601 cacaacccct cactcggcgc gccagtcttc cgatagactg cgtcgcccgg gtacccgtat
661 tcccaataaa gcctcttgct gtttgcatcc gaatcgtggt ctcgctgttc cttgggaggg
721 tctcctctga gtgattgact acccacgacg ggggtctttc atttgggggc tcgtccggga
781 tttggagacc cctgcccagg gaccaccgac ccaccaccgg gaggtaagct ggccagcaac
841 ttatctgtgt ctgtccgatt gtctagtgtc tatgtttgat gttatgcgcc tgcgtctgta
901 ctagttagct aactagctct gtatctggcg gacccgtggt ggaactgacg agttctgaac
961 acccggccgc aaccctggga gacgtcccag ggactttggg ggccgttttt gtggcccgac
```

Fig.16A 1021 ctgaggaagg gagtcgatgt ggaatccgac cccgtcagga tatgtggttc tggtaggaga 1081 cgagaaccta aaacagttcc cgcctccgtc tgaatttttg ctttcggttt ggaaccgaag 1141 ccgcgcgtct tgtctgctgc agcgctgcag catcgttctg tgttgtctct gtctgactgt 1201 gtttctgtat ttgtctgaaa attagggcca gactgttacc actcccttaa gtttgacctt 1261 aggtcactgg aaagatgtcg agcggatcgc tcacaaccag tcggtagatg tcaagaagag 1321 acgttgggtt accttctgct ctgcagaatg gccaaccttt aacgtcggat ggccgcgaga 1381 cggcaccttt aaccgagacc tcatcaccca ggttaagatc aaggtctttt cacctggccc 1441 gcatggacac ccagaccagg tccctacat cgtgacctgg gaagccttgg cttttgaccc 1501 ccctccctgg gtcaagccct ttgtacaccc taagcctccg cctcctcttc ctccatccgc 1561 cccgtctctc cccttgaac ctcctcgttc gaccccgcct cgatcctccc tttatccagc 1621 cctcactcct tctctaggcg ccggaattcg ttGCTACCGG TCGCCAACAT GGTGAGCAAG

1681 GGCGAGGAGC TGTTCACCGG GGTGGTGCCC ATCCTGGTCG AGCTGGACGG CGACGTGAAC

1741 GGCCACAAGT TCAGCGTGTC CGGCGAGGGC GAGGGCGATG CCACCTACGG CAAGCTGACC

1801 CTGAAGTTCA TCTGCACCAC CGGCAAGCTG CCCGTGCCCT GGCCCACCCT CGTGACCACC

1861 CTGACCTACG GCGTGCAGTG CTTCAGCCGC TACCCCGACC ACATGAAGCA GCACGACGTC

1921 TTCAAGTCCG CCATGCCCGA AGGCTACGTC CAGGAGCGCA CCATCTTCTT CAAGGACGAC

1981 GGCAACTACA AGACCCGCGC CGAGGTGAAG TTCGAGGGCG ACACCCTGGT GAACCGCATC

2041 GAGCTGAAGG GCATCGACTT CAAGGAGGAC GGCAACATCC TGGGGCACAA GCTGGAGTAC

2101 AACTACAACA GCCACAACGT CTATATCATG GCCGACAAGC AGAAGAACGG CATCAAGGTG

2161 AACTTCAAGA TCCGCCACAA CATCGAGGAC GGCAGCGTGC AGCTCGCCGA CCACTACCAG

2221 CAGAACACCC CCATCGGCGA CGGCCCCGTG CTGCTGCCCG ACAACCACTA CCTGAGCACC

*Fig.16B*

2281 CAGTCCGCCC TGAGCAAAGA CCCCAACGAG AAGCGCGATC ACATGGTCCT GCTGGAGTTC

2341 GTGACCGCCG CCGGGATCAC TCACGGCATG GACGAGCTGT ACAAGTAGCG GCCATGCTaa 2401 ctcgaggatc cGAaagaccc cacctgtagg tttggcaagc tagcttaagt aacgccattt 2461 tgcaaggcat ggaaaaatac ataactgaga atagagaagt tcagatcaag gtcaggaaca 2521 gatggaacag ctgaatatgg gccaaacagg atatctgtgg taagcagttc ctgccccggc 2581 tcagggccaa gaacagatgg aacagctgaa tatgggccaa acaggatatc tgtggtaagc 2641 agttcctgcc ccggctcagg gccaagaaca gatggtcccc agatgcggtc cagccctcag 2701 cagtttctag agaaccatca gatgtttcca gggtgcccca aggacctgaa atgaccctgt 2761 gccttatttg aactaaccaa tcagttcgct tctcgcttct gttcgcgcgc ttctgctccc 2821 cgagctcaat aaaagagccc acaaccccctc actcggggcg ccagtcctcc gattgactga 2881 gtcgcccggg tacccgtgta tccaataaac cctcttgcag ttgcatccga cttgtggtct 2941 cgctgttcct tgggagggtc tcctctgagt gattgactac ccgtcagcgg gggtctttca 3001 tttgggggct cgtccgggat cgggagaccc ctgcccaggg accaccgacc caccaccggg 3061 aggtaagctg gctgcctcgc gcgtttcggt gatgacggtg aaaacctctg acacatgcag 3121 ctcccggaga cggtcacagc ttgtctgtaa gcggatgccg ggagcagaca agcccgtcag 3181 ggcgcgtcag cgggtgttgg cgggtgtcgg ggcgcagcca tgacccagtc acgtagcgat 3241 agcggagtgt atactggctt aactatgcgg catcagagca gattgtactg agagtgcacc 3301 atatgcggtg tgaaataccg cacagatgcg taaggagaaa ataccgcatc aggcgctctt 3361 ccgcttcctc gctcactgac tcgctgcgct cggtcgttcg gctgcggcga gcggtatcag 3421 ctcactcaaa ggcggtaata cggttatcca cagaatcagg ggataacgca ggaaagaaca 3481 tgtgagcaaa aggccagcaa aaggccagga accgtaaaaa ggccgcgttg ctggcgtttt

*Fig.16C*

3541 tccataggct ccgccccct gacgagcatc acaaaaatcg acgctcaagt cagaggtggc 3601 gaaacccgac aggactataa agataccagg cgtttccccc tggaagctcc ctcgtgcgct 3661 ctcctgttcc gaccctgccg cttaccggat acctgtccgc ctttctccct tcgggaagcg 3721 tggcgctttc tcatagctca cgctgtaggt atctcagttc ggtgtaggtc gttcgctcca 3781 agctgggctg tgtgcacgaa ccccccgttc agcccgaccg ctgcgcctta tccggtaact 3841 atcgtcttga gtccaacccg gtaagacacg acttatcgcc actggcagca gccactggta 3901 acaggattag cagagcgagg tatgtaggcg gtgctacaga gttcttgaag tggtggccta 3961 actacggcta cactagaagg acagtatttg gtatctgcgc tctgctgaag ccagttacct 4021 tcggaaaaag agttggtagc tcttgatccg gcaaacaaac caccgctggt agcggtggtt 4081 ttttgtttg caagcagcag attacgcgca gaaaaaaagg atctcaagaa gatcctttga 4141 tcttttctac ggggtctgac gctcagtgga acgaaaactc acgttaaggg attttggtca 4201 tgagattatc aaaaaggatc ttcacctaga tccttttaaa ttaaaaatga agttttaaat 4261 caatctaaag tatatatgag taaacttggt ctgacagtta ccaatgctta atcagtgagg 4321 cacctatctc agcgatctgt ctatttcgtt catccatagt tgcctgactc cccgtcgtgt 4381 agataactac gatacgggag ggcttaccat ctggccccag tgctgcaatg ataccgcgag 4441 acccacgctc accggctcca gatttatcag caataaacca gccagccgga agggccgagc 4501 gcagaagtgg tcctgcaact ttatccgcct ccatccagtc tattaattgt tgccgggaag 4561 ctagagtaag tagttcgcca gttaatagtt tgcgcaacgt tgttgccatt gctgcaggca 4621 tcgtggtgtc acgctcgtcg tttggtatgg cttcattcag ctccggttcc caacgatcaa 4681 ggcgagttac atgatccccc atgttgtgca aaaaagcggt tagctccttc ggtcctccga 4741 tcgttgtcag aagtaagttg gccgcagtgt tatcactcat ggttatggca gcactgcata

*Fig. 16D*

4801 attctcttac tgtcatgcca tccgtaagat gcttttctgt gactggtgag tactcaacca 4861 agtcattctg agaatagtgt atgcggcgac cgagttgctc ttgcccggcg tcaacacggg 4921 ataataccgc gccacatagc agaactttaa aagtgctcat cattggaaaa cgttcttcgg 4981 ggcgaaaact ctcaaggatc ttaccgctgt tgagatccag ttcgatgtaa cccactcgtg 5041 cacccaactg atcttcagca tcttttactt tcaccagcgt ttctgggtga gcaaaaacag 5101 gaaggcaaaa tgccgcaaaa aagggaataa gggcgacacg gaaatgttga atactcatac 5161 tcttcctttt tcaatattat tgaagcattt atcagggtta ttgtctcatg agcggataca 5221 tatttgaatg tatttagaaa aataaacaaa taggggttcc gcgcacattt ccccgaaaag 5281 tgccacctga cgtctaagaa accattatta tcatgacatt aacctataaa aataggcgta 5341 tcacgaggcc ctttcgtctt caa
//

*Fig.16E* pLESN pLESN is a retroviral plasmid expressing the enhanced GFP gene driven by the LTR promoter.

```
  1 gaattgctag caattgctag caattgctag caattcatac cagatcaccg aaaactgtcc
 61 tccaaatgtg tccccctcac actcccaaat tcgcgggctt ctgcctctta gaccactcta
121 ccctattccc cacactcacc ggagccaaag ccgcggccct tccgtttctt tgcttttgaa
181 agaccccacc cgtaggtggc aagctagctt aagtaacgcc actttgcaag gcatggaaaa
241 atacataact gagaatagaa aagttcagat caaggtcagg aacaaagaaa cagctgaata
301 ccaaacagga tatctgtggt aagcggttcc tgccccggct cagggccaag aacagatgag
361 acagctgagt gatgggccaa acaggatatc tgtggtaagc agttcctgcc ccggctcggg
421 gccaagaaca gatggtcccc agatgcggtc cagccctcag cagtttctag tgaatcatca
481 gatgtttcca gggtgcccca aggacctgaa aatgaccctg taccttattt gaactaacca
541 atcagttcgc ttctcgcttc tgttcgcgcg cttccgctct ccgagctcaa taaaagagcc
601 cacaacccct cactcggcgc gccagtcttc cgatagactg cgtcgcccgg gtacccgtat
661 tcccaataaa gcctcttgct gtttgcatcc gaatcgtggt ctcgctgttc cttgggaggg
721 tctcctctga gtgattgact acccacgacg ggggtctttc atttgggggc tcgtccggga
781 tttggagacc cctgcccagg gaccaccgac ccaccaccgg gaggtaagct ggccagcaac
841 ttatctgtgt ctgtccgatt gtctagtgtc tatgtttgat gttatgcgcc tgcgtctgta
901 ctagttagct aactagctct gtatctggcg gacccgtggt ggaactgacg agttctgaac
961 acccggccgc aaccctggga gacgtcccag ggactttggg ggccgttttt gtggcccgac
1021 ctgaggaagg gagtcgatgt ggaatccgac cccgtcagga tatgtggttc tggtaggaga
1081 cgagaaccta aaacagttcc cgcctccgtc tgaattttg ctttcggttt ggaaccgaag
```

Fig. 17A 1141 ccgcgcgtct tgtctgctgc agcgctgcag catcgttctg tgttgtctct gtctgactgt 1201 gtttctgtat ttgtctgaaa attagggcca gactgttacc actcccttaa gtttgacctt 1261 aggtcactgg aaagatgtcg agcggatcgc tcacaaccag tcggtagatg tcaagaagag 1321 acgttgggtt accttctgct ctgcagaatg gccaaccttt aacgtcggat ggccgcgaga 1381 cggcaccttt aaccgagacc tcatcaccca ggttaagatc aaggtctttt cacctggccc 1441 gcatggacac ccagaccagg tccctacat cgtgacctgg gaagccttgg cttttgaccc 1501 ccctccctgg gtcaagccct ttgtacaccc taagcctccg cctcctcttc ctccatccgc 1561 cccgtctctc cccttgaac ctcctcgttc gaccccgcct cgatcctccc tttatccagc 1621 cctcactcct tctctaggcg ccggaattcg ttgctaccgg tcgccaccAT GGTGAGCAAG

1681 GGCGAGGAGC TGTTCACCGG GGTGGTGCCC ATCCTGGTCG AGCTGGACGG CGACGTGAAC

1741 GGCCACAAGT TCAGCGTGTC CGGCGAGGGC GAGGGCGATG CCACCTACGG CAAGCTGACC

1801 CTGAAGTTCA TCTGCACCAC CGGCAAGCTG CCCGTGCCCT GGCCCACCCT CGTGACCACC

1861 CTGACCTACG GCGTGCAGTG CTTCAGCCGC TACCCCGACC ACATGAAGCA GCACGACGTC

1921 TTCAAGTCCG CCATGCCCGA AGGCTACGTC CAGGAGCGCA CCATCTTCTT CAAGGACGAC

1981 GGCAACTACA AGACCCGCGC CGAGGTGAAG TTCGAGGGCG ACACCCTGGT GAACCGCATC

2041 GAGCTGAAGG GCATCGACTT CAAGGAGGAC GGCAACATCC TGGGGCACAA GCTGGAGTAC

2101 AACTACAACA GCCACAACGT CTATATCATG GCCGACAAGC AGAAGAACGG CATCAAGGTG

2161 AACTTCAAGA TCCGCCACAA CATCGAGGAC GGCAGCGTGC AGCTCGCCGA CCACTACCAG

2221 CAGAACACCC CCATCGGCGA CGGCCCCGTG CTGCTGCCCG ACAACCACTA CCTGAGCACC

2281 CAGTCCGCCC TGAGCAAAGA CCCCAACGAG AAGCGCGATC ACATGGTCCT GCTGGAGTTC

2341 GTGACCGCCG CCGGGATCAC TCACGGCATG GACGAGCTGT ACAAGTAGCG GCCAtgctaa

*Fig.17B*

2401 ctcgaggatc cggctgtgga atgtgtgtca gttagggtgt ggaaagtccc caggctcccc 2461 agcaggcaga agtatgcaaa gcatgcatct caattagtca gcaaccaggt gtggaaagtc 2521 cccaggctcc ccagcaggca gaagtatgca aagcatgcat ctcaattagt cagcaaccat 2581 agtcccgccc ctaactccgc ccatcccgcc cctaactccg cccagttccg cccattctcc 2641 gccccatggc tgactaattt tttttattta tgcagaggcc gaggccgcct cggcctctga 2701 gctattccag aagtagtgag gaggcttttt tggaggccta ggcttttgca aaaagcttgg 2761 gctgcaggtc gaggcggatc tgatcaagag acaggatgag gatcgtttcg catgattgaa 2821 caagatggat tgcacgcagg ttctccggcc gcttgggtgg agaggctatt cggctatgac 2881 tgggcacaac agacaatcgg ctgctctgat gccgccgtgt tccggctgtc agcgcagggg 2941 cgcccggttc tttttgtcaa gaccgacctg tccggtgccc tgaatgaact gcaggacgag 3001 gcagcgcggc tatcgtggct ggccacgacg ggcgttcctt gcgcagctgt gctcgacgtt 3061 gtcactgaag cgggaaggga ctggctgcta ttgggcgaag tgccggggca ggatctcctg 3121 tcatctcacc ttgctcctgc cgagaaagta tccatcatgg ctgatgcaat gcggcggctg 3181 catacgcttg atccggctac ctgcccattc gaccaccaag cgaaacatcg catcgagcga 3241 gcacgtactc ggatggaagc cggtcttgtc gatcaggatg atctggacga agagcatcag 3301 gggctcgcgc cagccgaact gttcgccagg ctcaaggcgc gcatgcccga cggcgaggat 3361 ctcgtcgtga cccatggcga tgcctgcttg ccgaatatca tggtggaaaa tggccgcttt 3421 tctggattca tcgactgtgg ccggctgggt gtggcggacc gctatcagga catagcgttg 3481 gctacccgtg atattgctga agagcttggc ggcgaatggg ctgaccgctt cctcgtgctt 3541 tacggtatcg ccgctcccga ttcgcagcgc atcgccttct atcgccttct tgacgagttc 3601 ttctgagcgg gactctgggg ttcgataaaa taaaagattt tatttagtct ccagaaaaag

*Fig.17C*

3661 gggggaatga aagaccccac ctgtaggttt ggcaagctag cttaagtaac gccattttgc 3721 aaggcatgga aaaatacata actgagaata gagaagttca gatcaaggtc aggaacagat 3781 ggaacagctg aatatgggcc aaacaggata tctgtggtaa gcagttcctg ccccggctca 3841 gggccaagaa cagatggaac agctgaatat gggccaaaca ggatatctgt ggtaagcagt 3901 tcctgccccg gctcagggcc aagaacagat ggtccccaga tgcggtccag ccctcagcag 3961 tttctagaga accatcagat gtttccaggg tgccccaagg acctgaaatg accctgtgcc 4021 ttatttgaac taaccaatca gttcgcttct cgcttctgtt cgcgcgcttc tgctccccga 4081 gctcaataaa agagcccaca acccctcact cggggcgcca gtcctccgat tgactgagtc 4141 gcccgggtac ccgtgtatcc aataaaccct cttgcagttg catccgactt gtggtctcgc 4201 tgttccttgg gagggtctcc tctgagtgat tgactacccg tcagcggggg tctttcattt 4261 ggggctcgt ccgggatcgg gagacccctg cccagggacc accgacccac caccgggagg 4321 taagctggct gcctcgcgcg tttcggtgat gacggtgaaa acctctgaca catgcagctc 4381 ccggagacgg tcacagcttg tctgtaagcg gatgccggga gcagacaagc ccgtcagggc 4441 gcgtcagcgg gtgttggcgg gtgtcggggc gcagccatga cccagtcacg tagcgatagc 4501 ggagtgtata ctggcttaac tatgcggcat cagagcagat tgtactgaga gtgcaccata 4561 tgcggtgtga ataccgcac agatgcgtaa ggagaaaata ccgcatcagg cgctcttccg 4621 cttcctcgct cactgactcg ctgcgctcgg tcgttcggct gcggcgagcg gtatcagctc 4681 actcaaaggc ggtaatacgg ttatccacag aatcagggga taacgcagga aagaacatgt 4741 gagcaaaagg ccagcaaaag gccaggaacc gtaaaaaggc cgcgttgctg gcgtttttcc 4801 ataggctccg ccccctgac gagcatcaca aaaatcgacg ctcaagtcag aggtggcgaa 4861 acccgacagg actataaaga taccaggcgt ttccccctgg aagctccctc gtgcgctctc

*Fig. 17D*

4921 ctgttccgac cctgccgctt accggatacc tgtccgcctt tctcccttcg ggaagcgtgg 4981 cgctttctca tagctcacgc tgtaggtatc tcagttcggt gtaggtcgtt cgctccaagc 5041 tgggctgtgt gcacgaaccc cccgttcagc ccgaccgctg cgccttatcc ggtaactatc 5101 gtcttgagtc caacccggta agacacgact tatcgccact ggcagcagcc actggtaaca 5161 ggattagcag agcgaggtat gtaggcggtg ctacagagtt cttgaagtgg tggcctaact 5221 acggctacac tagaaggaca gtatttggta tctgcgctct gctgaagcca gttaccttcg 5281 gaaaaagagt tggtagctct tgatccggca aacaaaccac cgctggtagc ggtggttttt 5341 ttgtttgcaa gcagcagatt acgcgcagaa aaaaaggatc tcaagaagat cctttgatct 5401 tttctacggg gtctgacgct cagtggaacg aaaactcacg ttaagggatt ttggtcatga 5461 gattatcaaa aaggatcttc acctagatcc ttttaaatta aaaatgaagt tttaaatcaa 5521 tctaaagtat atatgagtaa acttggtctg acagttacca atgcttaatc agtgaggcac 5581 ctatctcagc gatctgtcta tttcgttcat ccatagttgc ctgactcccc gtcgtgtaga 5641 taactacgat acgggagggc ttaccatctg gccccagtgc tgcaatgata ccgcgagacc 5701 cacgctcacc ggctccagat ttatcagcaa taaaccagcc agccggaagg gccgagcgca 5761 gaagtggtcc tgcaacttta tccgcctcca tccagtctat taattgttgc cgggaagcta 5821 gagtaagtag ttcgccagtt aatagtttgc gcaacgttgt tgccattgct gcaggcatcg 5881 tggtgtcacg ctcgtcgttt ggtatggctt cattcagctc cggttcccaa cgatcaaggc 5941 gagttacatg atcccccatg ttgtgcaaaa aagcggttag ctccttcggt cctccgatcg 6001 ttgtcagaag taagttggcc gcagtgttat cactcatggt tatggcagca ctgcataatt 6061 ctcttactgt catgccatcc gtaagatgct tttctgtgac tggtgagtac tcaaccaagt 6121 cattctgaga atagtgtatg cggcgaccga gttgctcttg cccggcgtca acacgggata

*Fig. 17E*

6181 ataccgcgcc acatagcaga actttaaaag tgctcatcat tggaaaacgt tcttcggggc 6241 gaaaactctc aaggatctta ccgctgttga gatccagttc gatgtaaccc actcgtgcac 6301 ccaactgatc ttcagcatct tttactttca ccagcgtttc tgggtgagca aaaacaggaa 6361 ggcaaaatgc cgcaaaaaag ggaataaggg cgacacggaa atgttgaata ctcatactct 6421 tcctttttca atattattga agcatttatc agggttattg tctcatgagc ggatacatat 6481 ttgaatgtat ttagaaaaat aaacaaatag gggttccgcg cacatttccc cgaaaagtgc 6541 cacctgacgt ctaagaaacc attattatca tgacattaac ctataaaaat aggcgtatca 6601 cgaggccctt tcgtcttcaa
//

*Fig.17F* pLNCE pLNCE is a retroviral plasmid expressing the enhanced GFP gene driven by the CMV promoter.

```
   1 gaattcatac cagatcaccg aaaactgtcc tccaaatgtg tccccctcac actcccaaat
  61 tcgcgggctt ctgcctctta gaccactcta ccctattccc cacactcacc ggagccaaag
 121 ccgcggccct tccgtttctt tgcttttgaa agaccccacc cgtaggtggc aagctagctt
 181 aagtaacgcc actttgcaag gcatggaaaa atacataact gagaatagaa aagttcagat
 241 caaggtcagg aacaaagaaa cagctgaata ccaaacagga tatctgtggt aagcggttcc
 301 tgccccggct cagggccaag aacagatgag acagctgagt gatgggccaa acaggatatc
 361 tgtggtaagc agttcctgcc ccggctcggg gccaagaaca gatggtcccc agatgcggtc
 421 cagccctcag cagtttctag tgaatcatca gatgtttcca gggtgcccca aggacctgaa
 481 aatgaccctg taccttattt gaactaacca atcagttcgc ttctcgcttc tgttcgcgcg
 541 cttccgctct ccgagctcaa taaaagagcc cacaacccct cactcggcgc gccagtcttc
 601 cgatagactg cgtcgcccgg gtacccgtat tcccaataaa gcctcttgct gtttgcatcc
 661 gaatcgtggt ctcgctgttc cttgggaggg tctcctctga gtgattgact acccacgacg
 721 ggggtctttc atttggggc tcgtccggga tttggagacc cctgcccagg gaccaccgac
 781 ccaccaccgg gaggtaagct ggccagcaac ttatctgtgt ctgtccgatt gtctagtgtc
 841 tatgtttgat gttatgcgcc tgcgtctgta ctagttagct aactagctct gtatctggcg
 901 gacccgtggt ggaactgacg agttctgaac acccggccgc aaccctggga gacgtcccag
 961 ggactttggg ggccgttttt gtggcccgac ctgaggaagg gagtcgatgt ggaatccgac
1021 cccgtcagga tatgtggttc tggtaggaga cgagaaccta aaacagttcc cgcctccgtc
```

Fig.18A 1081 tgaatttttg ctttcggttt ggaaccgaag ccgcgcgtct tgtctgctgc agcgctgcag 1141 catcgttctg tgttgtctct gtctgactgt gtttctgtat ttgtctgaaa attagggcca 1201 gactgttacc actcccttaa gtttgacctt aggtcactgg aaagatgtcg agcggatcgc 1261 tcacaaccag tcggtagatg tcaagaagag acgttgggtt accttctgct ctgcagaatg 1321 gccaaccttt aacgtcggat ggccgcgaga cggcaccttt aaccgagacc tcatcaccca 1381 ggttaagatc aaggtctttt cacctggccc gcatggacac ccagaccagg tcccctacat 1441 cgtgacctgg gaagccttgg cttttgaccc ccctccctgg gtcaagccct ttgtacaccc 1501 taagcctccg cctcctcttc ctccatccgc cccgtctctc cccctttgaac ctcctcgttc 1561 gaccccgcct cgatcctccc tttatccagc cctcactcct tctctaggcg ccggaattcc 1621 gatctgatca agagacagga tgaggatcgt ttcgcatgat tgaacaagat ggattgcacg 1681 caggttctcc ggccgcttgg gtggagaggc tattcggcta tgactgggca caacagacaa 1741 tcggctgctc tgatgccgcc gtgttccggc tgtcagcgca ggggcgcccg gttcttttg 1801 tcaagaccga cctgtccggt gccctgaatg aactgcagga cgaggcagcg cggctatcgt 1861 ggctggccac gacgggcgtt ccttgcgcag ctgtgctcga cgttgtcact gaagcgggaa 1921 gggactggct gctattgggc gaagtgccgg ggcaggatct cctgtcatct caccttgctc 1981 ctgccgagaa agtatccatc atggctgatg caatgcggcg gctgcatacg cttgatccgg 2041 ctacctgccc attcgaccac caagcgaaac atcgcatcga gcgagcacgt actcggatgg 2101 aagccggtct tgtcgatcag gatgatctgg acgaagagca tcaggggctc gcgccagccg 2161 aactgttcgc caggctcaag gcgcgcatgc ccgacggcga ggatctcgtc gtgacccatg 2221 gcgatgcctg cttgccgaat atcatggtgg aaaatggccg cttttctgga ttcatcgact 2281 gtggccggct gggtgtggcg gaccgctatc aggacatagc gttggctacc cgtgatattg 2341 ctgaagagct tggcggcgaa tgggctgacc gcttcctcgt gctttacggt atcgccgctc

*Fig.18B*

2401 ccgattcgca gcgcatcgcc ttctatcgcc ttcttgacga gttcttctga gcgggactct 2461 ggggttcgaa atgaccgacc aagcgacgcc caacctgcca tcacgagatt tcgattccac 2521 cgccgccttc tatgaaaggt tgggcttcgg aatcgttttc cgggacgccg gctggatgat 2581 cctccagcgc ggggatctca tgctggagtt cttcgcccac cccgggctcg atcccctcgc 2641 gagttggttc agctgctgcc tgaggctgga cgacctcgcg gagttctacc ggcagtgcaa 2701 atccgtcggc atccaggaaa ccagcagcgg ctatccgcgc atccatgccc ccgaactgca 2761 ggagtgggga ggcacgatgg ccgctttggt cgaggcGGAT CCGCGGCCGC Ctagttatta 2821 atagtaatca attacggggt cattagttca tagcccatat atggagttcc gcgttacata 2881 acttacggta aatggcccgc ctggctgacc gcccaacgac ccccgcccat tgacgtcaat 2941 aatgacgtat gttcccatag taacgccaat agggactttc cattgacgtc aatgggtgga 3001 gtatttacgg taaactgccc acttggcagt acatcaagtg tatcatatgc caagtacgcc 3061 ccctattgac gtcaatgacg gtaaatggcc cgcctggcat tatgcccagt acatgacctt 3121 atgggacttt cctacttggc agtacatcta cgtattagtc atcgctatta ccatggtgat 3181 gcggttttgg cagtacatca atgggcgtgg atagcggttt gactcacggg gatttccaag 3241 tctccacccc attgacgtca atgggagttt gttttggcac caaaatcaac gggactttcc 3301 aaaatgtcgt aacaactccg ccccattgac gcaaatgggc ggtaggcgtg tacggtggga 3361 ggtctatata agcagagctg gtttagtgaa ccgtcagatc cgctagcgct accggtcgcc 3421 accATGGTGA GCAAGGGCGA GGAGCTGTTC ACCGGGGTGG TGCCCATCCT GGTCGAGCTG

3481 GACGGCGACG TGAACGGCCA CAAGTTCAGC GTGTCCGGCG AGGGCGAGGG CGATGCCACC

3541 TACGGCAAGC TGACCCTGAA GTTCATCTGC ACCACCGGCA AGCTGCCCGT GCCCTGGCCC

3601 ACCCTCGTGA CCACCCTGAC CTACGGCGTG CAGTGCTTCA GCCGCTACCC CGACCACATG

*Fig. 18C*

3661 AAGCAGCACG ACGTCTTCAA GTCCGCCATG CCCGAAGGCT ACGTCCAGGA GCGCACCATC

3721 TTCTTCAAGG ACGACGGCAA CTACAAGACC CGCGCCGAGG TGAAGTTCGA GGGCGACACC

3781 CTGGTGAACC GCATCGAGCT GAAGGGCATC GACTTCAAGG AGGACGGCAA CATCCTGGGG

3841 CACAAGCTGG AGTACAACTA CAACAGCCAC AACGTCTATA TCATGGCCGA CAAGCAGAAG

3901 AACGGCATCA AGGTGAACTT CAAGATCCGC CACAACATCG AGGACGGCAG CGTGCAGCTC

3961 GCCGACCACT ACCAGCAGAA CACCCCCATC GGCGACGGCC CCGTGCTGCT GCCCGACAAC

4021 CACTACCTGA GCACCCAGTC CGCCCTGAGC AAAGACCCCA ACGAGAAGCG CGATCACATG

4081 GTCCTGCTGG AGTTCGTGAC CGCCGCCGGG ATCACTCACG GCATGGACGA GCTGTACAAG

4141 TAGCGGCCAa gcttgttaac atcgataaaa taaaagattt tatttagtct ccagaaaaag 4201 gggggaatga agaccccac ctgtaggttt ggcaagctag cttaagtaac gccattttgc 4261 aaggcatgga aaaatacata actgagaata gagaagttca gatcaaggtc aggaacagat 4321 ggaacagctg aatatgggcc aaacaggata tctgtggtaa gcagttcctg ccccggctca 4381 gggccaagaa cagatggaac agctgaatat gggccaaaca ggatatctgt ggtaagcagt 4441 tcctgccccg gctcagggcc aagaacagat ggtccccaga tgcggtccag ccctcagcag 4501 tttctagaga accatcagat gtttccaggg tgccccaagg acctgaaatg accctgtgcc 4561 ttatttgaac taaccaatca gttcgcttct cgcttctgtt cgcgcgcttc tgctccccga 4621 gctcaataaa agagcccaca acccctcact cggggcgcca gtcctccgat tgactgagtc 4681 gcccgggtac ccgtgtatcc aataaaccct cttgcagttg catccgactt gtggtctcgc 4741 tgttccttgg gagggtctcc tctgagtgat tgactacccg tcagcggggg tctttcattt 4801 ggggggctcgt ccgggatcgg gagacccctg cccagggacc accgacccac caccgggagg 4861 taagctggct gcctcgcgcg tttcggtgat gacggtgaaa acctctgaca catgcagctc

Fig.18D 4921 ccggagacgg tcacagcttg tctgtaagcg gatgccggga gcagacaagc ccgtcagggc 4981 gcgtcagcgg gtgttggcgg gtgtcggggc gcagccatga cccagtcacg tagcgatagc 5041 ggagtgtata ctggcttaac tatgcggcat cagagcagat tgtactgaga gtgcaccata 5101 tgcggtgtga ataccgcac agatgcgtaa ggagaaaata ccgcatcagg cgctcttccg 5161 cttcctcgct cactgactcg ctgcgctcgg tcgttcggct gcggcgagcg gtatcagctc 5221 actcaaaggc ggtaatacgg ttatccacag aatcagggga taacgcagga agaacatgt 5281 gagcaaaagg ccagcaaaag gccaggaacc gtaaaaaggc cgcgttgctg gcgtttttcc 5341 ataggctccg ccccctgac gagcatcaca aaaatcgacg ctcaagtcag aggtggcgaa 5401 acccgacagg actataaaga taccaggcgt ttccccctgg aagctccctc gtgcgctctc 5461 ctgttccgac cctgccgctt accggatacc tgtccgcctt tctcccttcg ggaagcgtgg 5521 cgctttctca tagctcacgc tgtaggtatc tcagttcggt gtaggtcgtt cgctccaagc 5581 tgggctgtgt gcacgaaccc cccgttcagc ccgaccgctg cgccttatcc ggtaactatc 5641 gtcttgagtc caacccggta agacacgact tatcgccact ggcagcagcc actggtaaca 5701 ggattagcag agcgaggtat gtaggcggtg ctacagagtt cttgaagtgg tggcctaact 5761 acggctacac tagaaggaca gtatttggta tctgcgctct gctgaagcca gttaccttcg 5821 gaaaaagagt tggtagctct tgatccggca aacaaaccac cgctggtagc ggtggttttt 5881 ttgtttgcaa gcagcagatt acgcgcagaa aaaaggatc tcaagaagat cctttgatct 5941 tttctacggg gtctgacgct cagtggaacg aaaactcacg ttaagggatt ttggtcatga 6001 gattatcaaa aaggatcttc acctagatcc ttttaaatta aaaatgaagt tttaaatcaa 6061 tctaaagtat atatgagtaa acttggtctg acagttacca atgcttaatc agtgaggcac 6121 ctatctcagc gatctgtcta tttcgttcat ccatagttgc ctgactcccc gtcgtgtaga

*Fig.18E*

6181 taactacgat acgggagggc ttaccatctg gccccagtgc tgcaatgata ccgcgagacc 6241 cacgctcacc ggctccagat ttatcagcaa taaaccagcc agccggaagg gccgagcgca 6301 gaagtggtcc tgcaacttta tccgcctcca tccagtctat taattgttgc cgggaagcta 6361 gagtaagtag ttcgccagtt aatagtttgc gcaacgttgt tgccattgct gcaggcatcg 6421 tggtgtcacg ctcgtcgttt ggtatggctt cattcagctc cggttcccaa cgatcaaggc 6481 gagttacatg atcccccatg ttgtgcaaaa aagcggttag ctccttcggt cctccgatcg 6541 ttgtcagaag taagttggcc gcagtgttat cactcatggt tatggcagca ctgcataatt 6601 ctcttactgt catgccatcc gtaagatgct tttctgtgac tggtgagtac tcaaccaagt 6661 cattctgaga atagtgtatg cggcgaccga gttgctcttg cccggcgtca acacgggata 6721 ataccgcgcc acatagcaga actttaaaag tgctcatcat tggaaaacgt tcttcggggc 6781 gaaaactctc aaggatctta ccgctgttga gatccagttc gatgtaaccc actcgtgcac 6841 ccaactgatc ttcagcatct tttactttca ccagcgtttc tgggtgagca aaaacaggaa 6901 ggcaaaatgc cgcaaaaaag gaataagggc gacacggaa atgttgaata ctcatactct 6961 tcctttttca atattattga agcatttatc agggttattg tctcatgagc ggatacatat 7021 ttgaatgtat ttagaaaaat aaacaaatag gggttccgcg cacatttccc cgaaaagtgc 7081 cacctgacgt ctaagaaacc attattatca tgacattaac ctataaaaat aggcgtatca 7141 cgaggccctt tcgtcttcaa
//

*Fig.18F* pLNChRG pLNChRG is a retroviral plasmid expressing the hRGFP gene driven by the CMV promoter.

```
   1 gaattcatac cagatcaccg aaaactgtcc tccaaatgtg tccccctcac actcccaaat
  61 tcgcgggctt ctgcctctta gaccactcta ccctattccc cacactcacc ggagccaaag
 121 ccgcggccct tccgtttctt tgcttttgaa agaccccacc cgtaggtggc aagctagctt
 181 aagtaacgcc actttgcaag gcatggaaaa atacataact gagaatagaa aagttcagat
 241 caaggtcagg aacaaagaaa cagctgaata ccaaacagga tatctgtggt aagcggttcc
 301 tgccccggct cagggccaag aacagatgag acagctgagt gatgggccaa acaggatatc
 361 tgtggtaagc agttcctgcc ccggctcggg gccaagaaca gatggtcccc agatgcggtc
 421 cagccctcag cagtttctag tgaatcatca gatgtttcca gggtgcccca aggacctgaa
 481 aatgaccctg taccttattt gaactaacca atcagttcgc ttctcgcttc tgttcgcgcg
 541 cttccgctct ccgagctcaa taaaagagcc cacaacccct cactcggcgc gccagtcttc
 601 cgatagactg cgtcgcccgg gtacccgtat tcccaataaa gcctcttgct gtttgcatcc
 661 gaatcgtggt ctcgctgttc cttgggaggg tctcctctga gtgattgact acccacgacg
 721 ggggtctttc atttgggggc tcgtccggga tttggagacc cctgcccagg gaccaccgac
 781 ccaccaccgg gaggtaagct ggccagcaac ttatctgtgt ctgtccgatt gtctagtgtc
 841 tatgtttgat gttatgcgcc tgcgtctgta ctagttagct aactagctct gtatctggcg
 901 gacccgtggt ggaactgacg agttctgaac acccggccgc aaccctggga gacgtcccag
 961 ggactttggg ggccgttttt gtggcccgac ctgaggaagg gagtcgatgt ggaatccgac
1021 cccgtcagga tatgtggttc tggtaggaga cgagaaccta aaacagttcc cgcctccgtc
```

*Fig.19A*

1081 tgaatttttg ctttcggttt ggaaccgaag ccgcgcgtct tgtctgctgc agcgctgcag 1141 catcgttctg tgttgtctct gtctgactgt gtttctgtat ttgtctgaaa attagggcca 1201 gactgttacc actcccttaa gtttgacctt aggtcactgg aaagatgtcg agcggatcgc 1261 tcacaaccag tcggtagatg tcaagaagag acgttgggtt accttctgct ctgcagaatg 1321 gccaaccttt aacgtcggat ggccgcgaga cggcaccttt aaccgagacc tcatcaccca 1381 ggttaagatc aaggtctttt cacctggccc gcatggacac ccagaccagg tcccctacat 1441 cgtgacctgg gaagccttgg cttttgaccc ccctccctgg gtcaagccct ttgtacaccc 1501 taagcctccg cctcctcttc ctccatccgc cccgtctctc cccttgaac ctcctcgttc 1561 gaccccgcct cgatcctccc tttatccagc cctcactcct tctctaggcg ccggaattcc 1621 gatctgatca agagacagga tgaggatcgt ttcgcatgat tgaacaagat ggattgcacg 1681 caggttctcc ggccgcttgg gtggagaggc tattcggcta tgactgggca caacagacaa 1741 tcggctgctc tgatgccgcc gtgttccggc tgtcagcgca ggggcgcccg gttcttttg 1801 tcaagaccga cctgtccggt gccctgaatg aactgcagga cgaggcagcg cggctatcgt 1861 ggctggccac gacgggcgtt ccttgcgcag ctgtgctcga cgttgtcact gaagcgggaa 1921 gggactggct gctattgggc gaagtgccgg ggcaggatct cctgtcatct caccttgctc 1981 ctgccgagaa agtatccatc atggctgatg caatgcggcg gctgcatacg cttgatccgg 2041 ctacctgccc attcgaccac caagcgaaac atcgcatcga gcgagcacgt actcggatgg 2101 aagccggtct tgtcgatcag gatgatctgg acgaagagca tcagggggctc gcgccagccg 2161 aactgttcgc caggctcaag gcgcgcatgc ccgacggcga ggatctcgtc gtgacccatg 2221 gcgatgcctg cttgccgaat atcatggtgg aaaatggccg cttttctgga ttcatcgact 2281 gtggccggct gggtgtggcg gaccgctatc aggacatagc gttggctacc cgtgatattg 2341 ctgaagagct tggcggcgaa tgggctgacc gcttcctcgt gctttacggt atcgccgctc

*Fig.19B*

2401 ccgattcgca gcgcatcgcc ttctatcgcc ttcttgacga gttcttctga gcgggactct 2461 ggggttcgaa atgaccgacc aagcgacgcc caacctgcca tcacgagatt tcgattccac 2521 cgccgccttc tatgaaaggt tgggcttcgg aatcgttttc cgggacgccg gctggatgat 2581 cctccagcgc ggggatctca tgctggagtt cttcgcccac cccgggctcg atcccctcgc 2641 gagttggttc agctgctgcc tgaggctgga cgacctcgcg gagttctacc ggcagtgcaa 2701 atccgtcggc atccaggaaa ccagcagcgg ctatccgcgc atccatgccc ccgaactgca 2761 ggagtgggga ggcacgatgg ccgctttggt cgaggcggat ccggccatta gccatattat 2821 tcattggtta tatagcataa atcaatattg gctattggcc attgcatacg ttgtatccat 2881 atcataaatat gtacatttat attggctcat gtccaacatt accgccatgt tgacattgat 2941 tattgactag ttattaatag taatcaatta cggggtcatt agttcatagc ccatatatgg 3001 agttccgcgt tacataactt acggtaaatg gcccgcctgg ctgaccgccc aacgaccccc 3061 gcccattgac gtcaataatg acgtatgttc ccatagtaac gccaataggg actttccatt 3121 gacgtcaatg ggtggagtat ttacggtaaa ctgcccactt ggcagtacat caagtgtatc 3181 atatgccaag tacgccccct attgacgtca atgacggtaa atggcccgcc tggcattatg 3241 cccagtacat gaccttatgg gactttccta cttggcagta catctacgta ttagtcatcg 3301 ctattaccat ggtgatgcgg ttttggcagt acatcaatgg gcgtggatag cggtttgact 3361 cacggggatt tccaagtctc caccccattg acgtcaatgg gagtttgttt tggcaccaaa 3421 atcaacggga ctttccaaaa tgtcgtaaca actccgcccc attgacgcaa atgggcggta 3481 ggcatgtacg gtgggaggtc tatataagca gagctcgttt agtgaaccgt cagatcgcct 3541 ggagacgcca tccacgctgt tttgacctcc atagaagaca ccgggaccga tccagcctcc 3601 gcggccccaa gcttgttGGC CGCCGCCACC atgagcaagg gcgaggaact gttcactggc

*Fig.19C*

3661 gtggtcccaa ttctcgtgga actggatggc gatgtgaatg ggcacaaatt ttctgtcagt 3721 ggagagggtg aaggtgatgc aacatacgga aagctcaccc tgaaattcat ctgcaccact 3781 ggaaagctcc ctgtgccatg gccaacactg gtcactacct tcacctatgg cgtgcagtgc 3841 ttttccagat acccagacca tatgaagcag catgactttt tcaagagtgc catgcccgag 3901 ggctatgtgc aggagagaac catcttttc aaagatgacg ggaactacaa gacccgcgct 3961 gaagtcaagt tcgaaggtga caccctggtg aatagaatcg agttgaaggg cattgacttt 4021 aaggaagatg gaaacattct cggccacaag ctggaataca actataactc ccacaatgtg 4081 tacatcatgg ccgacaagca aaagaatggc atcaaggtca acttcaagat cagacacaac 4141 attgaggatg gatccgtgca gctggccgac cattatcaac agaacactcc aatcggcgac 4201 ggccctgtgc tcctcccaga caaccattac ctgtccaccc agtctgccct gtctaaagat 4261 cccaacgaaa agagagacca catggtcctg ctggagtttg tgaccgctgc tgggatcaca 4321 catggcatgg acgagctgta caagtgaGCa acatcgataa aataaaagat tttatttagt 4381 ctccagaaaa aggggggaat gaaagacccc acctgtaggt ttggcaagct agcttaagta 4441 acgccatttt gcaaggcatg gaaaaataca taactgagaa tagagaagtt cagatcaagg 4501 tcaggaacag atggaacagc tgaatatggg ccaaacagga tatctgtggt aagcagttcc 4561 tgccccggct cagggccaag aacagatgga acagctgaat atgggccaaa caggatatct 4621 gtggtaagca gttcctgccc cggctcaggg ccaagaacag atggtcccca gatgcggtcc 4681 agccctcagc agtttctaga gaaccatcag atgtttccag ggtgccccaa ggacctgaaa 4741 tgaccctgtg ccttatttga actaaccaat cagttcgctt ctcgcttctg ttcgcgcgct 4801 tctgctcccc gagctcaata aaagagccca aaccccctca ctcggggcgc cagtcctccg 4861 attgactgag tcgcccgggt acccgtgtat ccaataaacc ctcttgcagt tgcatccgac

Fig.19D 4921 ttgtggtctc gctgttcctt gggagggtct cctctgagtg attgactacc cgtcagcggg 4981 ggtctttcat ttgggggctc gtccgggatc gggagacccc tgcccaggga ccaccgaccc 5041 accaccggga ggtaagctgg ctgcctcgcg cgtttcggtg atgacggtga aaacctctga 5101 cacatgcagc tcccggagac ggtcacagct tgtctgtaag cggatgccgg gagcagacaa 5161 gcccgtcagg gcgcgtcagc gggtgttggc gggtgtcggg gcgcagccat gacccagtca 5221 cgtagcgata gcggagtgta tactggctta actatgcggc atcagagcag attgtactga 5281 gagtgcacca tatgcggtgt gaaataccgc acagatgcgt aaggagaaaa taccgcatca 5341 ggcgctcttc cgcttcctcg ctcactgact cgctgcgctc ggtcgttcgg ctgcggcgag 5401 cggtatcagc tcactcaaag gcggtaatac ggttatccac agaatcaggg gataacgcag 5461 gaaagaacat gtgagcaaaa ggccagcaaa aggccaggaa ccgtaaaaag gccgcgttgc 5521 tggcgttttt ccataggctc cgcccccctg acgagcatca caaaaatcga cgctcaagtc 5581 agaggtggcg aaacccgaca ggactataaa gataccaggc gtttccccct ggaagctccc 5641 tcgtgcgctc tcctgttccg accctgccgc ttaccggata cctgtccgcc tttctccctt 5701 cgggaagcgt ggcgctttct catagctcac gctgtaggta tctcagttcg gtgtaggtcg 5761 ttcgctccaa gctgggctgt gtgcacgaac cccccgttca gcccgaccgc tgcgccttat 5821 ccggtaacta tcgtcttgag tccaacccgg taagacacga cttatcgcca ctggcagcag 5881 ccactggtaa caggattagc agagcgaggt atgtaggcgg tgctacagag ttcttgaagt 5941 ggtggcctaa ctacggctac actagaagga cagtatttgg tatctgcgct ctgctgaagc 6001 cagttacctt cggaaaaaga gttggtagct cttgatccgg caaacaaacc accgctggta 6061 gcggtggttt ttttgtttgc aagcagcaga ttacgcgcag aaaaaaagga tctcaagaag 6121 atcctttgat cttttctacg gggtctgacg ctcagtggaa cgaaaactca cgttaaggga 6181 ttttggtcat gagattatca aaaaggatct tcacctagat ccttttaaat taaaaatgaa

*Fig.19E*

6241 gttttaaatc aatctaaagt atatatgagt aaacttggtc tgacagttac caatgcttaa 6301 tcagtgaggc acctatctca gcgatctgtc tatttcgttc atccatagtt gcctgactcc 6361 ccgtcgtgta gataactacg atacgggagg gcttaccatc tggccccagt gctgcaatga 6421 taccgcgaga cccacgctca ccggctccag atttatcagc aataaaccag ccagccggaa 6481 gggccgagcg cagaagtggt cctgcaactt tatccgcctc catccagtct attaattgtt 6541 gccgggaagc tagagtaagt agttcgccag ttaatagttt gcgcaacgtt gttgccattg 6601 ctgcaggcat cgtggtgtca cgctcgtcgt ttggtatggc ttcattcagc tccggttccc 6661 aacgatcaag gcgagttaca tgatccccca tgttgtgcaa aaaagcggtt agctccttcg 6721 gtcctccgat cgttgtcaga agtaagttgg ccgcagtgtt atcactcatg gttatggcag 6781 cactgcataa ttctcttact gtcatgccat ccgtaagatg cttttctgtg actggtgagt 6841 actcaaccaa gtcattctga gaatagtgta tgcggcgacc gagttgctct tgcccggcgt 6901 caacacggga taataccgcg ccacatagca gaactttaaa agtgctcatc attggaaaac 6961 gttcttcggg gcgaaaactc tcaaggatct taccgctgtt gagatccagt tcgatgtaac 7021 ccactcgtgc acccaactga tcttcagcat cttttacttt caccagcgtt tctgggtgag 7081 caaaaacagg aaggcaaaat gccgcaaaaa agggaataag ggcgacacgg aaatgttgaa 7141 tactcatact cttccttttt caatattatt gaagcattta tcaggttat tgtctcatga 7201 gcggatacat atttgaatgt atttagaaaa ataaacaaat aggggttccg cgcacatttc 7261 cccgaaaagt gccacctgac gtctaagaaa ccattattat catgacatta acctataaaa 7321 ataggcgtat cacgaggccc tttcgtcttc aa
//

*Fig.19F* pLTKOCEGFP pLTKOCEGFP is a retroviral plasmid expressing 2 genes, LTR promoting HSVTK gene and CMV promoting the enhanced GFP gene.

```
    1 GAATTGCTAG CAATTGCTAG CAATTGCTAG CAATTCATAC
      CAGATCACCG AAAACTGTCC
   61 TCCAAATGTG TCCCCCTCAC ACTCCCAAAT TCGCGGGCTT
      CTGCCTCTTA GACCACTCTA
  121 CCCTATTCCC CACACTCACC GGAGCCAAAG CCGCGGCCCT
      TCCGTTTCTT TGCTTTTGAA
  181 AGACCCCACC CGTAGGTGGC AAGCTAGCTT AAGTAACGCC
      ACTTTGCAAG GCATGGAAAA
  241 ATACATAACT GAGAATAGAA AAGTTCAGAT CAAGGTCAGG
      AACAAAGAAA CAGCTGAATA
  301 CCAAACAGGA TATCTGTGGT AAGCGGTTCC TGCCCCGGCT
      CAGGGCCAAG AACAGATGAG
  361 ACAGCTGAGT GATGGGCCAA ACAGGATATC TGTGGTAAGC
      AGTTCCTGCC CCGGCTCGGG
  421 GCCAAGAACA GATGGTCCCC AGATGCGGTC CAGCCCTCAG
      CAGTTTCTAG TGAATCATCA
  481 GATGTTTCCA GGGTGCCCCA AGGACCTGAA AATGACCCTG
      TACCTTATTT GAACTAACCA
  541 ATCAGTTCGC TTCTCGCTTC TGTTCGCGCG CTTCCGCTCT
      CCGAGCTCAA TAAAAGAGCC
  601 CACAACCCCT CACTCGGCGC GCCAGTCTTC CGATAGACTG
      CGTCGCCCGG GTACCCGTAT
  661 TCCCAATAAA GCCTCTTGCT GTTTGCATCC GAATCGTGGT
      CTCGCTGTTC CTTGGGAGGG
  721 TCTCCTCTGA GTGATTGACT ACCCACGACG GGGGTCTTTC
      ATTTGGGGGC TCGTCCGGGA
  781 TTTGGAGACC CCTGCCCAGG GACCACCGAC CCACCACCGG
      GAGGTAAGCT GGCCAGCAAC
  841 TTATCTGTGT CTGTCCGATT GTCTAGTGTC TATGTTTGAT
      GTTATGCGCC TGCGTCTGTA
  901 CTAGTTAGCT AACTAGCTCT GTATCTGGCG GACCCGTGGT
      GGAACTGACG AGTTCTGAAC
  961 ACCCGGCCGC AACCCTGGGA GACGTCCCAG GGACTTTGGG
      GGCCGTTTTT GTGGCCCGAC
 1021 CTGAGGAAGG GAGTCGATGT GGAATCCGAC CCCGTCAGGA
      TATGTGGTTC TGGTAGGAGA
```

Fig.20A

1081 CGAGAACCTA AAACAGTTCC CGCCTCCGTC TGAATTTTTG CTTTCGGTTT GGAACCGAAG

1141 CCGCGCGTCT TGTCTGCTGC AGCGCTGCAG CATCGTTCTG TGTTGTCTCT GTCTGACTGT

1201 GTTTCTGTAT TTGTCTGAAA ATTAGGGCCA GACTGTTACC ACTCCCTTAA GTTTGACCTT

1261 AGGTCACTGG AAAGATGTCG AGCGGATCGC TCACAACCAG TCGGTAGATG TCAAGAAGAG

1321 ACGTTGGGTT ACCTTCTGCT CTGCAGAATG GCCAACCTTT AACGTCGGAT GGCCGCGAGA

1381 CGGCACCTTT AACCGAGACC TCATCACCCA GGTTAAGATC AAGGTCTTTT CACCTGGCCC

1441 GCATGGACAC CCAGACCAGG TCCCCTACAT CGTGACCTGG GAAGCCTTGG CTTTTGACCC

1501 CCCTCCCTGG GTCAAGCCCT TGTACACCC TAAGCCTCCG CCTCCTCTTC CTCCATCCGC

1561 CCCGTCTCTC CCCCTTGAAC CTCCTCGTTC GACCCCGCCT CGATCCTCCC TTTATCCAGC

1621 CCTCACTCCT TCTCTAGGCG CCGGAATTCG GCTTCCAAGC TTCGGCCAGC GCCTTGTAGA

1681 AGCGCGTATG GCTTCGTACC CCTGCCATCA ACACGCGTCT GCGTTCGACC AGGCTGCGCG

1741 TTCTCGCGGC CATAGCAACC GACGTACGGC GTTGCGCCCT CGCCGGCAGC AAGAAGCCAC

1801 GGAAGTCCGC CTGGAGCAGA AAATGCCCAC GCTACTGCGG GTTTATATAG ACGGTCCTCA

1861 CGGGATGGGG AAAACCACCA CCACGCAACT GCTGGTGGCC CTGGGTTCGC GCGACGATAT

1921 CGTCTACGTA CCCGAGCCGA TGACTTACTG GCGGGTGCTG GGGGCTTCCG AGACAATCGC

1981 GAACATCTAC ACCACACAAC ACCGCCTCGA CCAGGGTGAG ATATCGGCCG GGACGCGGC

2041 GGTGGTAATG ACAAGCGCCC AGATAACAAT GGGCATGCCT TATGCCGTGA CCGACGCCGT

2101 TCTGGCTCCT CATGTCGGGG GGGAGGCTGG GAGTTCACAT GCCCCGCCCC CGGCCCTCAC

2161 CCTCATCTTC GACCGCCATC CCATCGCCGC CCTCCTGTGC TACCCGGCCG CGCGATACCT

2221 TATGGGCAGC ATGACCCCCC AGGCCGTGCT GGCGTTCGTG GCCCTCATCC CGCCGACCTT

2281 GCCCGGCACA ACATCGTGT TGGGGGCCCT TCCGGAGGAC AGACACATCG ACCGCCTGGC

*Fig.20B*

2341 CAAACGCCAG CGCCCCGGCG AGCGGCTTGA CCTGGCTATG CTGGCCGCGA TTCGCCGCGT

2401 TTACGGGCTG CTTGCCAATA CGGTGCGGTA TCTGCAGGGC GGCGGGTCGT GGTGGGAGGA

2461 TTGGGGACAG CTTTCGGGGA CGGCCGTGCC GCCCCAGGGT GCCGAGCCCC AGAGCAACGC

2521 GGGCCCACGA CCCCATATCG GGGACACGTT ATTTACCCTG TTTCGGGCCC CCGAGTTGCT

2581 GGCCCCCAAC GGCGACCTGT ATAACGTGTT TGCCTGGGCC TTGGACGTCT TGGCCAAACG

2641 CCTCCGTCCC ATGCACGTCT TTATCCTGGA TTACGACCAA TCGCCCGCCG GCTGCCGGGA

2701 CGCCCTGCTG CAACTTACCT CCGGGATGGT CCAGACCCAC GTCACCACCC CAGGCTCCAT

2761 ACCGACGATC TGCGACCTGG CGCGCACGTT TGCCCGGGAG ATGGGGGAGG CTAACTGAAA

2821 CACGGAAGGA GACAATACCG GAAGCTTGGA AGCCGAATTC GTTAACTCGA gGGATCCGCG

2881 GCCGCCtagt tattaatagt aatcaattac ggggtcatta gttcatagcc catatatgga 2941 gttccgcgtt acataactta cggtaaatgg cccgcctggc tgaccgccca acgaccccg 3001 cccattgacg tcaataatga cgtatgttcc catagtaacg ccaataggga ctttccattg 3061 acgtcaatgg gtggagtatt tacggtaaac tgcccacttg gcagtacatc aagtgtatca 3121 tatgccaagt acgccccta ttgacgtcaa tgacggtaaa tggcccgcct ggcattatgc 3181 ccagtacatg accttatggg actttcctac ttggcagtac atctacgtat tagtcatcgc 3241 tattaccatg gtgatgcggt tttggcagta catcaatggg cgtggatagc ggtttgactc 3301 acggggattt ccaagtctcc accccattga cgtcaatggg agtttgtttt ggcaccaaaa 3361 tcaacgggac tttccaaaat gtcgtaacaa ctccgcccca ttgacgcaaa tgggcggtag 3421 gcgtgtacgg tgggaggtct atataagcag agctggttta gtgaaccgtc agatccgcta 3481 gcgctaccgg tcgccaccAT GGTGAGCAAG GGCGAGGAGC TGTTCACCGG GGTGGTGCCC

3541 ATCCTGGTCG AGCTGGACGG CGACGTGAAC GGCCACAAGT TCAGCGTGTC CGGCGAGGGC

*Fig. 20C*

3601 GAGGGCGATG CCACCTACGG CAAGCTGACC CTGAAGTTCA TCTGCACCAC CGGCAAGCTG

3661 CCCGTGCCCT GGCCCACCCT CGTGACCACC CTGACCTACG GCGTGCAGTG CTTCAGCCGC

3721 TACCCCGACC ACATGAAGCA GCACGACGTC TTCAAGTCCG CCATGCCCGA AGGCTACGTC

3781 CAGGAGCGCA CCATCTTCTT CAAGGACGAC GGCAACTACA AGACCCGCGC CGAGGTGAAG

3841 TTCGAGGGCG ACACCCTGGT GAACCGCATC GAGCTGAAGG GCATCGACTT CAAGGAGGAC

3901 GGCAACATCC TGGGGCACAA GCTGGAGTAC AACTACAACA GCCACAACGT CTATATCATG

3961 GCCGACAAGC AGAAGAACGG CATCAAGGTG AACTTCAAGA TCCGCCACAA CATCGAGGAC

4021 GGCAGCGTGC AGCTCGCCGA CCACTACCAG CAGAACACCC CCATCGGCGA CGGCCCCGTG

4081 CTGCTGCCCG ACAACCACTA CCTGAGCACC CAGTCCGCCC TGAGCAAAGA CCCCAACGAG

4141 AAGCGCGATC ACATGGTCCT GCTGGAGTTC GTGACCGCCG CCGGGATCAC TCACGGCATG

4201 GACGAGCTGT ACAAGTAGCG GCCAagcttg ttaacatcga taaaataaaa gattttattt 4261 agtctccaga aaagggggg aatgaaagac cccacctgta ggtttggcaa gctagcttaa 4321 gtaacgccat tttgcaaggc atggaaaaat acataactga gaatagagaa gttcagatca 4381 aggtcaggaa cagatggaac agctgaatat gggccaaaca ggatatctgt ggtaagcagt 4441 tcctgccccg gctcagggcc aagaacagat ggaacagctg aatatgggcc aaacaggata 4501 tctgtggtaa gcagttcctg ccccggctca gggccaagaa cagatggtcc ccagatgcgg 4561 tccagccctc agcagtttct agagaaccat cagatgtttc cagggtgccc caaggacctg 4621 aaatgaccct gtgccttatt tgaactaacc aatcagttcg cttctcgctt ctgttcgcgc 4681 gcttctgctc cccgagctca ataaaagagc ccacaacccc tcactcgggg cgccagtcct 4741 ccgattgact gagtcgcccg ggtacccgtg tatccaataa accctcttgc agttgcatcc 4801 gacttgtggt ctcgctgttc cttgggaggg tctcctctga gtgattgact acccgtcagc

*Fig.20D*

4861 gggggtctttt catttgggggg ctcgtccggg atcgggagac ccctgcccag ggaccaccga 4921 cccaccaccg ggaggtaagc tggctgcctc gcgcgtttcg gtgatgacgg tgaaaacctc 4981 tgacacatgc agctcccgga gacggtcaca gcttgtctgt aagcggatgc cgggagcaga 5041 caagcccgtc agggcgcgtc agcgggtgtt ggcgggtgtc ggggcgcagc catgacccag 5101 tcacgtagcg atagcggagt gtatactggc ttaactatgc ggcatcagag cagattgtac 5161 tgagagtgca ccatatgcgg tgtgaaatac cgcacagatg cgtaaggaga aaataccgca 5221 tcaggcgctc ttccgcttcc tcgctcactg actcgctgcg ctcggtcgtt cggctgcggc 5281 gagcggtatc agctcactca aaggcggtaa tacggttatc cacagaatca ggggataacg 5341 caggaaagaa catgtgagca aaaggccagc aaaaggccag gaaccgtaaa aaggccgcgt 5401 tgctggcgtt tttccatagg ctccgccccc ctgacgagca tcacaaaaat cgacgctcaa 5461 gtcagaggtg gcgaaacccg acaggactat aaagatacca ggcgtttccc cctggaagct 5521 ccctcgtgcg ctctcctgtt ccgaccctgc cgcttaccgg atacctgtcc gcctttctcc 5581 cttcgggaag cgtggcgctt tctcatagct cacgctgtag gtatctcagt tcggtgtagg 5641 tcgttcgctc caagctgggc tgtgtgcacg aaccccccgt tcagcccgac cgctgcgcct 5701 tatccggtaa ctatcgtctt gagtccaacc cggtaagaca cgacttatcg ccactggcag 5761 cagccactgg taacaggatt agcagagcga ggtatgtagg cggtgctaca gagttcttga 5821 agtggtggcc taactacggc tacactagaa ggacagtatt tggtatctgc gctctgctga 5881 agccagttac cttcggaaaa agagttggta gctcttgatc cggcaaacaa accaccgctg 5941 gtagcggtgg tttttttgtt tgcaagcagc agattacgcg cagaaaaaaa ggatctcaag 6001 aagatccttt gatcttttct acggggtctg acgctcagtg gaacgaaaac tcacgttaag 6061 ggattttggt catgagatta tcaaaaagga tcttcaccta gatcctttta aattaaaaat

Fig.20E 6121 gaagttttaa atcaatctaa agtatatatg agtaaacttg gtctgacagt taccaatgct 6181 taatcagtga ggcacctatc tcagcgatct gtctatttcg ttcatccata gttgcctgac 6241 tccccgtcgt gtagataact acgatacggg agggcttacc atctggcccc agtgctgcaa 6301 tgataccgcg agacccacgc tcaccggctc cagatttatc agcaataaac cagccagccg 6361 gaagggccga gcgcagaagt ggtcctgcaa ctttatccgc ctccatccag tctattaatt 6421 gttgccggga agctagagta agtagttcgc cagttaatag tttgcgcaac gttgttgcca 6481 ttgctgcagg catcgtggtg tcacgctcgt cgtttggtat ggcttcattc agctccggtt 6541 cccaacgatc aaggcgagtt acatgatccc ccatgttgtg caaaaaagcg gttagctcct 6601 tcggtcctcc gatcgttgtc agaagtaagt tggccgcagt gttatcactc atggttatgg 6661 cagcactgca taattctctt actgtcatgc catccgtaag atgcttttct gtgactggtg 6721 agtactCAAC CAAGTCATTC TGAGAATAGT GTATGCGGCG ACCGAGTTGC TCTTGCCCGG

6781 CGTCAACACG GGATAATACC GCGCCACATA GCAGAACTTT AAAAGTGCTC ATCATTGGAA

6841 AACGTTCTTC GGGGCGAAAA CTCTCAAGGA TCTTACCGCT GTTGAGATCC AGTTCGATGT

6901 AACCCACTCG TGCACCCAAC TGATCTTCAG CATCTTTTAC TTTCACCAGC GTTTCTGGGT

6961 GAGCAAAAAC AGGAAGGCAA AATGCCGCAA AAAAGGGAAT AAGGGCGACA CGGAAATGTT

7021 GAATACTCAT ACTCTTCCTT TTTCAATATT ATTGAAGCAT TTATCAGGGT TATTGTCTCA

7081 TGAGCGGATA CATATTTGAA TGTATTTAGA AAAATAAACA AATAGGGGTT CCGCGCACAT

7141 TTCCCCGAAA AGTGCCACCT GACGTCTAAG AAACCATTAT TATCATGACA TTAACCTATA

7201 AAAATAGGCG TATCACGAGG CCCTTTCGTC TTCAA
//

Fig.20F pLNChG65T pLNChG65T is a retroviral plasmid expressing the hGFP-S65T gene driven by the CMV promoter.

```
   1 gaattcatac cagatcaccg aaaactgtcc tccaaatgtg tccccctcac actcccaaat
  61 tcgcgggctt ctgcctctta gaccactcta ccctattccc cacactcacc ggagccaaag
 121 ccgcggccct tccgtttctt tgcttttgaa agaccccacc cgtaggtggc aagctagctt
 181 aagtaacgcc actttgcaag gcatggaaaa atacataact gagaatagaa aagttcagat
 241 caaggtcagg aacaaagaaa cagctgaata ccaaacagga tatctgtggt aagcggttcc
 301 tgccccggct cagggccaag aacagatgag acagctgagt gatgggccaa acaggatatc
 361 tgtggtaagc agttcctgcc ccggctcggg gccaagaaca gatggtcccc agatgcggtc
 421 cagccctcag cagtttctag tgaatcatca gatgtttcca gggtgcccca aggacctgaa
 481 aatgaccctg taccttattt gaactaacca atcagttcgc ttctcgcttc tgttcgcgcg
 541 cttccgctct ccagctcaa taaaagagcc cacaacccct cactcggcgc gccagtcttc
 601 cgatagactg cgtcgcccgg gtacccgtat tcccaataaa gcctcttgct gtttgcatcc
 661 gaatcgtggt ctcgctgttc cttgggaggg tctcctctga gtgattgact acccacgacg
 721 ggggtctttc atttgggggc tcgtccggga tttggagacc cctgcccagg gaccaccgac
 781 ccaccaccgg gaggtaagct ggccagcaac ttatctgtgt ctgtccgatt gtctagtgtc
 841 tatgtttgat gttatgcgcc tgcgtctgta ctagttagct aactagctct gtatctggcg
 901 gacccgtggt ggaactgacg agttctgaac acccggccgc aaccctggga gacgtcccag
 961 ggactttggg ggccgttttt gtggcccgac ctgaggaagg gagtcgatgt ggaatccgac
1021 cccgtcagga tatgtggttc tggtaggaga cgagaaccta aaacagttcc cgcctccgtc
```

*Fig. 21A*

1081 tgaatttttg ctttcggttt ggaaccgaag ccgcgcgtct tgtctgctgc agcgctgcag 1141 catcgttctg tgttgtctct gtctgactgt gtttctgtat ttgtctgaaa attagggcca 1201 gactgttacc actcccttaa gtttgaccttt aggtcactgg aaagatgtcg agcggatcgc 1261 tcacaaccag tcggtagatg tcaagaagag acgttgggtt accttctgct ctgcagaatg 1321 gccaaccttt aacgtcggat ggccgcgaga cggcacctttt aaccgagacc tcatcaccca 1381 ggttaagatc aaggtctttt cacctggccc gcatggacac ccagaccagg tccctacat 1441 cgtgacctgg gaagccttgg cttttgaccc ccctccctgg gtcaagccct ttgtacaccc 1501 taagcctccg cctcctcttc ctccatccgc cccgtctctc ccccttgaac ctcctcgttc 1561 gaccccgcct cgatcctccc tttatccagc cctcactcct tctctaggcg ccggaattcc 1621 gatctgatca agagacagga tgaggatcgt ttcgcatgat tgaacaagat ggattgcacg 1681 caggttctcc ggccgcttgg gtggagaggc tattcggcta tgactgggca caacagacaa 1741 tcggctgctc tgatgccgcc gtgttccggc tgtcagcgca ggggcgcccg gttcttttttg 1801 tcaagaccga cctgtccggt gccctgaatg aactgcagga cgaggcagcg cggctatcgt 1861 ggctggccac gacgggcgtt ccttgcgcag ctgtgctcga cgttgtcact gaagcgggaa 1921 gggactggct gctattgggc gaagtgccgg ggcaggatct cctgtcatct caccttgctc 1981 ctgccgagaa agtatccatc atggctgatg caatgcggcg gctgcatacg cttgatccgg 2041 ctacctgccc attcgaccac caagcgaaac atcgcatcga gcgagcacgt actcggatgg 2101 aagccggtct tgtcgatcag gatgatctgg acgaagagca tcaggggctc gcgccagccg 2161 aactgttcgc caggctcaag gcgcgcatgc ccgacggcga ggatctcgtc gtgacccatg 2221 gcgatgcctg cttgccgaat atcatggtgg aaaatggccg cttttctgga ttcatcgact 2281 gtggccggct gggtgtggcg gaccgctatc aggacatagc gttggctacc cgtgatattg

*Fig.21B*

2341 ctgaagagct tggcggcgaa tgggctgacc gcttcctcgt gctttacggt atcgccgctc 2401 ccgattcgca gcgcatcgcc ttctatcgcc ttcttgacga gttcttctga gcgggactct 2461 ggggttcgaa atgaccgacc aagcgacgcc caacctgcca tcacgagatt tcgattccac 2521 cgccgccttc tatgaaaggt tgggcttcgg aatcgttttc cgggacgccg gctggatgat 2581 cctccagcgc ggggatctca tgctggagtt cttcgcccac cccgggctcg atcccctcgc 2641 gagttggttc agctgctgcc tgaggctgga cgacctcgcg gagttctacc ggcagtgcaa 2701 atccgtcggc atccaggaaa ccagcagcgg ctatccgcgc atccatgccc ccgaactgca 2761 ggagtgggga ggcacgatgg ccgctttggt cgaggcggat ccggccatta gccatattat 2821 tcattggtta tatagcataa atcaatattg gctattggcc attgcatacg ttgtatccat 2881 atcataatat gtacatttat attggctcat gtccaacatt accgccatgt tgacattgat 2941 tattgactag ttattaatag taatcaatta cggggtcatt agttcatagc ccatatatgg 3001 agttccgcgt tacataactt acggtaaatg gcccgcctgg ctgaccgccc aacgaccccc 3061 gcccattgac gtcaataatg acgtatgttc ccatagtaac gccaataggg actttccatt 3121 gacgtcaatg ggtggagtat ttacggtaaa ctgcccactt ggcagtacat caagtgtatc 3181 atatgccaag tacgccccct attgacgtca atgacggtaa atggcccgcc tggcattatg 3241 cccagtacat gaccttatgg gactttccta cttggcagta catctacgta ttagtcatcg 3301 ctattaccat ggtgatgcgg ttttggcagt acatcaatgg gcgtggatag cggtttgact 3361 cacggggatt tccaagtctc cacccccattg acgtcaatgg gagtttgttt tggcaccaaa 3421 atcaacggga ctttccaaaa tgtcgtaaca actccgcccc attgacgcaa atgggcggta 3481 ggcatgtacg gtgggaggtc tatataagca gagctcgttt agtgaaccgt cagatcgcct 3541 ggagacgcca tccacgctgt tttgacctcc atagaagaca ccgggaccga tccagcctcc

*Fig.21C*

3601 gcggccccAA GCTTGCCGCC ACCATGGTGA GCAAGGGCGA GGAGCTCTTC ACCGGGGTGG

3661 TGCCCATCCT GGTCGAGCTG GACGGCGACG TGAACGGCCA CAAGTTCAGC GTGTCCGGCG

3721 AGGGCGACCC CGATGCCACC TACGGCAAGC TGACCCTGAA GTTCATCTGC ACCACCGGCA

3781 AGCTGCCCGT GCCCTGGCCC ACCCTCGTCA CCACCTTCAC CTACGGCGTG CAGTGCTTCA

3841 GCCGCTACCC CGACCACATG AAGCAGCACG ACTTCTTCAA GTCCGCCATG CCCGAAGGCT

3901 ACGTCCAGGA GCGCACCATC TTCTTCAAGG ACGACGGCAA CTACAAGACC CGCGCCGAGG

3961 TGAAGTTCGA GGGCGACACC CTGGTGAACC GCATCGAGCT GAAGGGCATC GACTTCAAGG

4021 AGGACGGCAA CATCCTGGGG CACAAGCTGG AGTACAACTA CAACAGCCAC AACGTCTATA

4081 TCATGGCCGA CAAGCAGAAG AACGGCATCA AGGTGAACTT CAAGATCCCC CACAACATCG

4141 AGGACGGCAG CGTGCAGCTC GCCGACCACT ACCAGCAGAA CACCCCCATC GGCGACGGCC

4201 CCGTGCTGCT GCCCGACAAC CACTACCTGA GCACCCAGTC CGCCCTGAGC AAAGACCCCA

4261 ACGAGAAGCG CGATCACATG GTCCTGCTGG AGTTCGTGAC CGCCGCCGGG ATCACTCACG

4321 GCATGGACGA GCTGTACAAG TAAAGCGGCC aacatcgata aaataaaaga ttttatttag 4381 tctccagaaa aaggggggaa tgaaagaccc cacctgtagg tttggcaagc tagcttaagt 4441 aacgccattt tgcaaggcat ggaaaaatac ataactgaga atagagaagt tcagatcaag 4501 gtcaggaaca gatggaacag ctgaatatgg gccaaacagg atatctgtgg taagcagttc 4561 ctgccccggc tcagggccaa gaacagatgg aacagctgaa tatgggccaa acaggatatc 4621 tgtggtaagc agttcctgcc ccggctcagg gccaagaaca gatggtcccc agatgcggtc 4681 cagccctcag cagtttctag agaaccatca gatgtttcca gggtgcccca aggacctgaa 4741 atgaccctgt gccttatttg aactaaccaa tcagttcgct tctcgcttct gttcgcgcgc 4801 ttctgctccc cgagctcaat aaaagagccc acaaccccctc actcggggcg ccagtcctcc

Fig.21D 4861 gattgactga gtcgcccggg tacccgtgta tccaataaac cctcttgcag ttgcatccga 4921 cttgtggtct cgctgttcct tgggagggtc tcctctgagt gattgactac ccgtcagcgg 4981 gggtctttca tttgggggct cgtccgggat cgggagaccc ctgcccaggg accaccgacc 5041 caccaccggg aggtaagctg gctgcctcgc gcgtttcggt gatgacggtg aaaacctctg 5101 acacatgcag ctcccggaga cggtcacagc ttgtctgtaa gcggatgccg ggagcagaca 5161 agcccgtcag ggcgcgtcag cgggtgttgg cgggtgtcgg ggcgcagcca tgacccagtc 5221 acgtagcgat agcggagtgt atactggctt aactatgcgg catcagagca gattgtactg 5281 agagtgcacc atatgcggtg tgaaataccg cacagatgcg taaggagaaa ataccgcatc 5341 aggcgctctt ccgcttcctc gctcactgac tcgctgcgct cggtcgttcg gctgcggcga 5401 gcggtatcag ctcactcaaa ggcggtaata cggttatcca cagaatcagg ggataacgca 5461 ggaaagaaca tgtgagcaaa aggccagcaa aaggccagga accgtaaaaa ggccgcgttg 5521 ctggcgtttt tccataggct ccgcccccct gacgagcatc acaaaaatcg acgctcaagt 5581 cagaggtggc gaaacccgac aggactataa agataccagg cgtttccccc tggaagctcc 5641 ctcgtgcgct ctcctgttcc gaccctgccg cttaccggat acctgtccgc ctttctccct 5701 tcgggaagcg tggcgctttc tcatagctca cgctgtaggt atctcagttc ggtgtaggtc 5761 gttcgctcca agctgggctg tgtgcacgaa ccccccgttc agcccgaccg ctgcgcctta 5821 tccggtaact atcgtcttga gtccaacccg gtaagacacg acttatcgcc actggcagca 5881 gccactggta acaggattag cagagcgagg tatgtaggcg gtgctacaga gttcttgaag 5941 tggtggccta actacggcta cactagaagg acagtatttg gtatctgcgc tctgctgaag 6001 ccagttacct tcggaaaaag agttggtagc tcttgatccg gcaaacaaac caccgctggt 6061 agcggtggtt tttttgtttg caagcagcag attacgcgca gaaaaaaagg atctcaagaa

*Fig.21E*

6121 gatcctttga tcttttctac ggggtctgac gctcagtgga acgaaaactc acgttaaggg 6181 attttggtca tgagattatc aaaaaggatc ttcacctaga tccttttaaa ttaaaaatga 6241 agttttaaat caatctaaag tatatatgag taaacttggt ctgacagtta ccaatgctta 6301 atcagtgagg cacctatctc agcgatctgt ctatttcgtt catccatagt tgcctgactc 6361 cccgtcgtgt agataactac gatacgggag ggcttaccat ctggccccag tgctgcaatg 6421 ataccgcgag acccacgctc accggctcca gatttatcag caataaacca gccagccgga 6481 agggccgagc gcagaagtgg tcctgcaact ttatccgcct ccatccagtc tattaattgt 6541 tgccgggaag ctagagtaag tagttcgcca gttaatagtt tgcgcaacgt tgttgccatt 6601 gctgcaggca tcgtggtgtc acgctcgtcg tttggtatgg cttcattcag ctccggttcc 6661 caacgatcaa ggcgagttac atgatccccc atgttgtgca aaaaagcggt tagctccttc 6721 ggtcctccga tcgttgtcag aagtaagttg gccgcagtgt tatcactcat ggttatggca 6781 gcactgcata attctcttac tgtcatgcca tccgtaagat gcttttctgt gactggtgag 6841 tactcaacca agtcattctg agaatagtgt atgcggcgac cgagttgctc ttgcccggcg 6901 tcaacacggg ataataccgc gccacatagc agaactttaa aagtgctcat cattggaaaa 6961 cgttcttcgg ggcgaaaact ctcaaggatc ttaccgctgt tgagatccag ttcgatgtaa 7021 cccactcgtg cacccaactg atcttcagca tcttttactt tcaccagcgt ttctgggtga 7081 gcaaaaacag gaaggcaaaa tgccgcaaaa aagggaataa gggcgacacg gaaatgttga 7141 atactcatac tcttcctttt tcaatattat tgaagcattt atcagggtta ttgtctcatg 7201 agcggataca tatttgaatg tatttagaaa aataaacaaa tagggggttcc gcgcacattt 7261 ccccgaaaag tgccacctga cgtctaagaa accattatta tcatgacatt aacctataaa 7321 aataggcgta tcacgaggcc ctttcgtctt caa
//

*Fig.21F*

VEHICLES FOR STABLE TRANSFER OF GREEN FLUORESCENT PROTEIN GENE AND METHODS OF USE FOR SAME

CROSS-REFERENCE TO RELATED APPLICATION

This application is a continuation-in-part of provisional application Serial. No. 60/010,371 filed Jan. 22, 1996.

BACKGROUND OF THE INVENTION

Gene therapy involves the transfer of therapeutic genes into living cells. The potential clinical applications of gene therapy are numerous and include the treatment of a wide variety of diseases, such as those resulting from genetic defects as well as cancer and diseases caused by viral infections, such as AIDS. A number of human genetic diseases that result from a lesion in a single gene have been proposed as candidates for gene therapy. These include bone marrow disorders, erythroid cell defects, metabolic disorders resulting from defects in liver enzymes, and diseases of the central nervous system.

For some of these diseases, the introduction of a functional homolog of the defective gene and the production of even small amounts of the missing gene product would have a beneficial effect. For example, 10–20% production of the normal levels of Factor IX can alleviate severe hemophilia B. Yao, et al. (1991) *B. Proc. Natl. Acad. Sci.* 88:8101–8105.

Since gene therapy evolved in the early 70's there have been several clinical trials involving retroviral transfer of either therapeutic genes or suicide genes. Gene transfer of ADA gene to correct for a genetic defect, was the first gene therapy trial which began in 1990. Culver, K., et al, (1990). Transfer of a suicide gene into brain tumors followed in 1992. Culver, K., et al. (1992) *Science* 256:1550–1552. The gene transfer vehicle in both of these trials is a disabled retrovirus. Retroviral vectors are designed to transfer the gene of interest into target cells which must be undergoing cell division.

ADA is a rare genetic immunodeficiency disease caused when a defect occurs in both copies of the ADA gene. Children affected by this disease may have a severe combined, immunodeficiency (SCID) which could lead to death by common infections in their first months of life. Ex vivo gene transfer of the ADA gene into patients' T lymphocytes resulted in a beneficial therapy for the children in the 1990 trial. However, treatments must be repeated often to maintain sufficient levels of ADA in the bloodstream. In brain tumor trials, in situ gene transfer of the suicide gene, the HsTk gene, followed by ganciclovir treatment was used to eradicate the tumors. Although only a small portion of the tumor cells are transduced using this method, a "bystander" effect is hypothesized to help spread the killing.

In the above-described systems the therapeutic impact of gene therapy is at a minimum. Thus, there is a need to improve the efficiency of gene transfer. Currently, researchers are experimenting with alternative methods to increase transduction efficiency. However, there is a need for a quick and efficient marker gene to assess the results.

Murine retroviral vectors have emerged in the past several years as the most common vehicle to deliver marker genes. Other viral vectors such as adenoviruses, herpes viruses, adeno-associated viruses, and non-viral methods such as plasmids have also been used for gene transfer. Gene transfer systems often include markers such as β-galactosidase, luciferase, chloramphenicol acetyltransferase, and alkaline phosphatase. Detection of these markers involve either cell fixation that kills the cells and the addition of a substrate or antibody mediated detection. These methods are often time consuming and are prone to endogenous high background.

Another group of gene transfer markers convey drug resistance and thus allow positive selection of transfected cells through selection of resistant colonies. Although drug selectable markers allow the detection of living cells by expressing the transgene, they require that the cells survive in a toxic environment over a long period of time. Also, the neomycin-resistance gene, which confers resistance to the neomycin analog G418, has been shown to have deleterious effects upon the expression of other genes in retroviral vectors. Emerman, M., et al. (1986) *Nucleic Acids Res.* 14, 9381–9396.

A novel marker gene is now available that will alleviate these cumbersome and time consuming steps for detecting gene transfer. The Green Fluorescent Protein (GFP) is a vibrant green bioluminescent marker which offers outstanding properties. The gene has been sequenced, humanized and is commercially available through several sources, however there has been much difficulty in finding a suitable transformation vehicle that will give stable expression in mammalian cells.

It is therefore a primary objective of the present invention to provide a gene transfer marker that overcomes the deficiencies of currently available gene transfer markers as described above.

It is another objective of the present invention to provide a gene transfer marker that provides rapid identification of gene transfer in living mammalian cells.

It is a further objective of the present invention to provide a gene transfer marker that can be easily visualized.

It is yet a further objective of the present invention to provide a gene transfer marker that is stable and is effectively and efficiently transferred into living cells.

These and other objectives will become apparent from the following description.

SUMMARY OF THE INVENTION

The present invention describes the cloning and characterization of amphotropic retroviral vectors capable of demonstrating efficient, stable transfer of humanized, red shifted GFP (hRGFP) gene into mammalian cells. Living cells transfected and/or transduced with hRGFP have a stable, bright green fluorescence after excitation with blue light.

The inventors have generated transformation vehicles containing a gene for an improved, humanized and redshifted version of the Aequorea victoria green fluorescent protein (hRGFP) from various viral vectors. The hRGFP gene has been used to produce amphotropic vector producer cell lines that demonstrate vibrant green fluorescence after excitation with blue light. These vehicles represent a substantial improvement over currently available gene transfer marking systems. Bright, long-term expression of the hRGFP gene in living eukaryotic cells will advance the study of gene transfer, gene expression, and gene product function in vitro and in vivo, particularly for human gene therapy applications.

BRIEF DESCRIPTION OF THE DRAWINGS

The file of this patent contains at least one drawing executed in color.

3A: PA317 cells without DNA transfection visualized under 40× magnification using the Green Fluorescent Protein Longpass filter.

3B: PA317 cells transfected with 5 μg pLNCG DNA and visualized after 48 hours under 40× magnification excited using the GFP Longpass filter set (420–470 nm).

3C: PA317 cells transfected with 5 μg pLNChRG DNA and visualized after 40 hours under 40× magnification using the FITC filter set (450–490 nm).

Figure 4:

FIG. 4 relates to the section of hRGFP gene activity in stable, transfected PA317 vector producer cells. The photograph shows the expression of hRGFP in mouse PA317 packaging cell after transfection with plasmid pLNChRG and selection in G418 for 2 weeks. Selected cells were trypsin digested and plated onto glass coverslips for viewing. PA317 cells were transfected with pLNChRG and visualized >24 hours after plating on glass coverslips under 40× magnification using the FITC filter set.

Figure 5A:
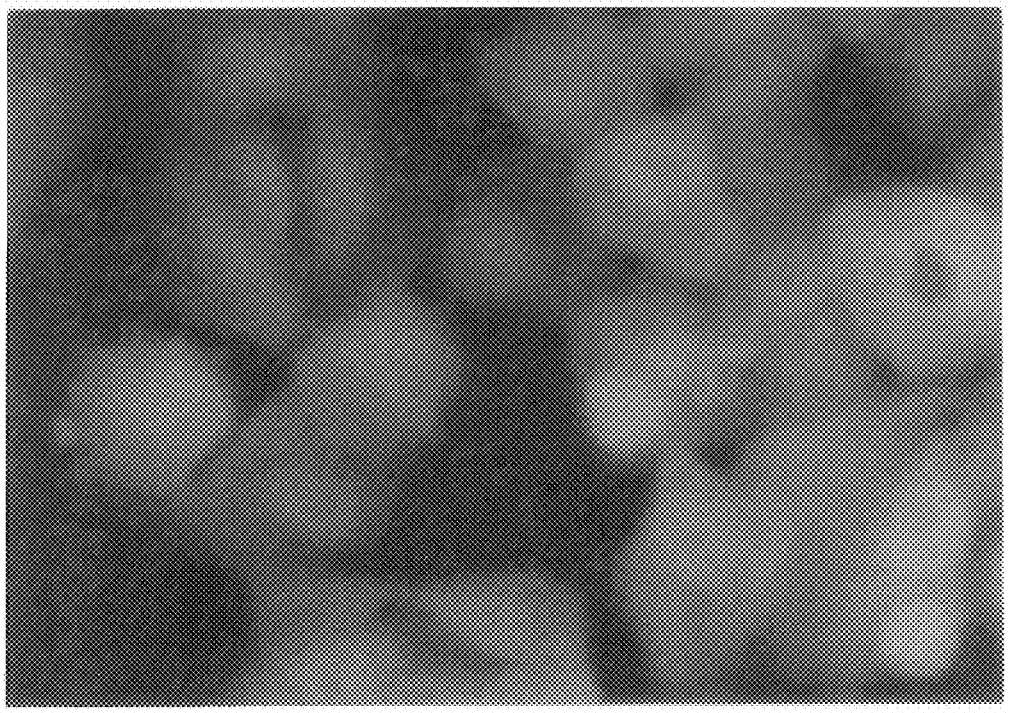
Figure 5B:

FIGS. 5A–5B relate to fluorescence detection in hRGFP transduced A375 melanoma and NIH3T3tk– fibroblast cells. The photograph shows expression of hRGFP in human A375 melanoma and murine NIH3T3tk– fibroblast cells after transduction with the LNChRG retroviral vector. After transduction cells were selected in G418 for 2 weeks. Selected cells were trypsin digested and plated onto glass coverslips for viewing using the FITC filter set.

5A: A375 melanoma cells transduced with LNChRG retroviral vector and visualized under 40× magnification.

5B: NIH3T3tk– murine fibroblast cells transduced with LNChRG retroviral vector under 40× magnification.

FIGS. 6A–6D relate to FACS analysis of pLNChRG transfected PA317 vector producer cells or pLNChRG transduced human melanoma cells. The photographs show the determination of hRGFP activity in G418 selected, stable populations of mammalian cells. Cells were trypsin digested and washed before analysis in a EPICS Profile II Analyzer.

6A: PA317 packaging cells without transfection (negative control).

6B: LNChRG transfected PA317 vector producer cells expressing hRGFP gene activity after excitation. Large shift in peak detected mean fluorescence corresponding with hRGFP activity.

6C: Nontransduced A375 cells demonstrate minimal detectable fluorescence (negative control).

6D: LNChRG transduced A375 cells expressing hRGFP gene activity after excitation. Large shift in peak detected mean fluorescence corresponding with hRGFP activity. All FACS analysis used the FL1 emission channel used to monitor green fluorescence. Count: cell number counted at given fluorescence intensity; y-axis is a log scale of mean intensity of green fluorescence detected.

Figure 7:
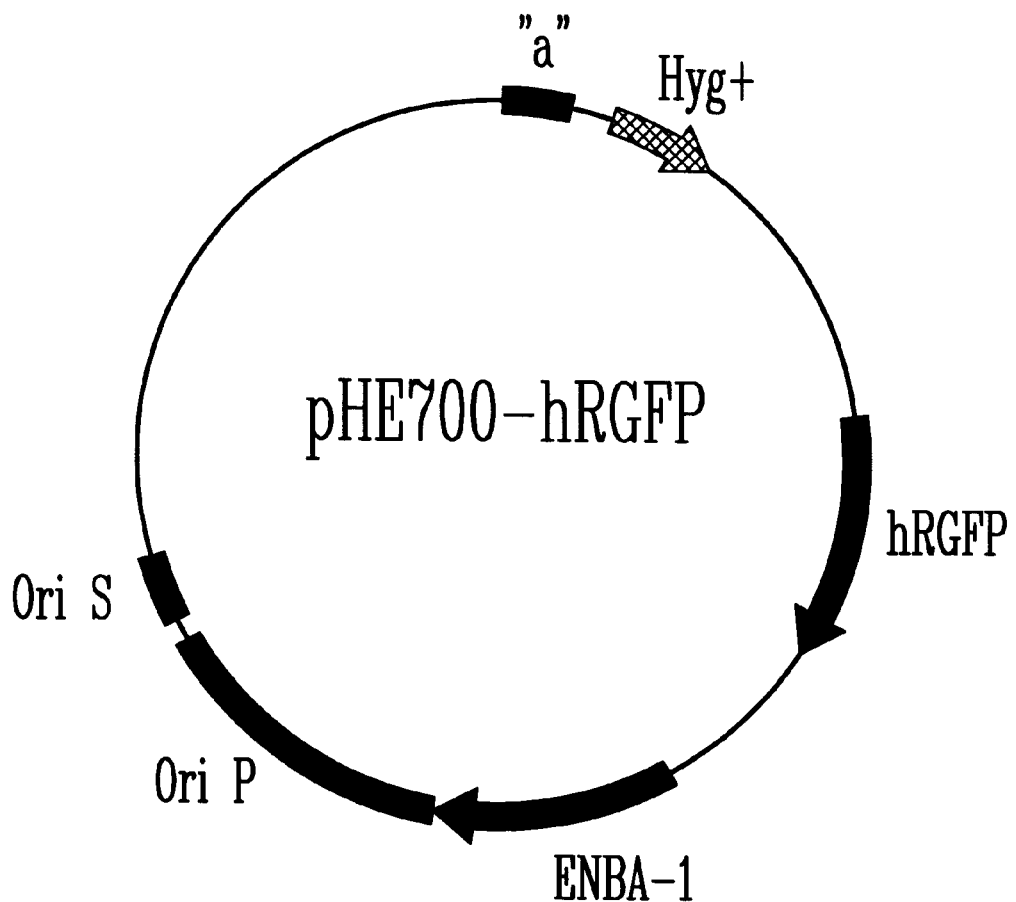

FIG. 7 is a depiction of the plasmid vector pHE700-hRGFP. "a" is a HSV-1 packaging signal; Hyg$^+$ is a hygromycin resistance gene; hRGFP is a humanized red shifted fluorescent protein gene; ENBA-1 is the Epstein-Barr virus gene encoding the EBV nuclear antigen EBNA-1; OriP is the Epstein-Barr virus unique latent replication origin; OriS is a HSV-1 replication origin.

Figure 8A:
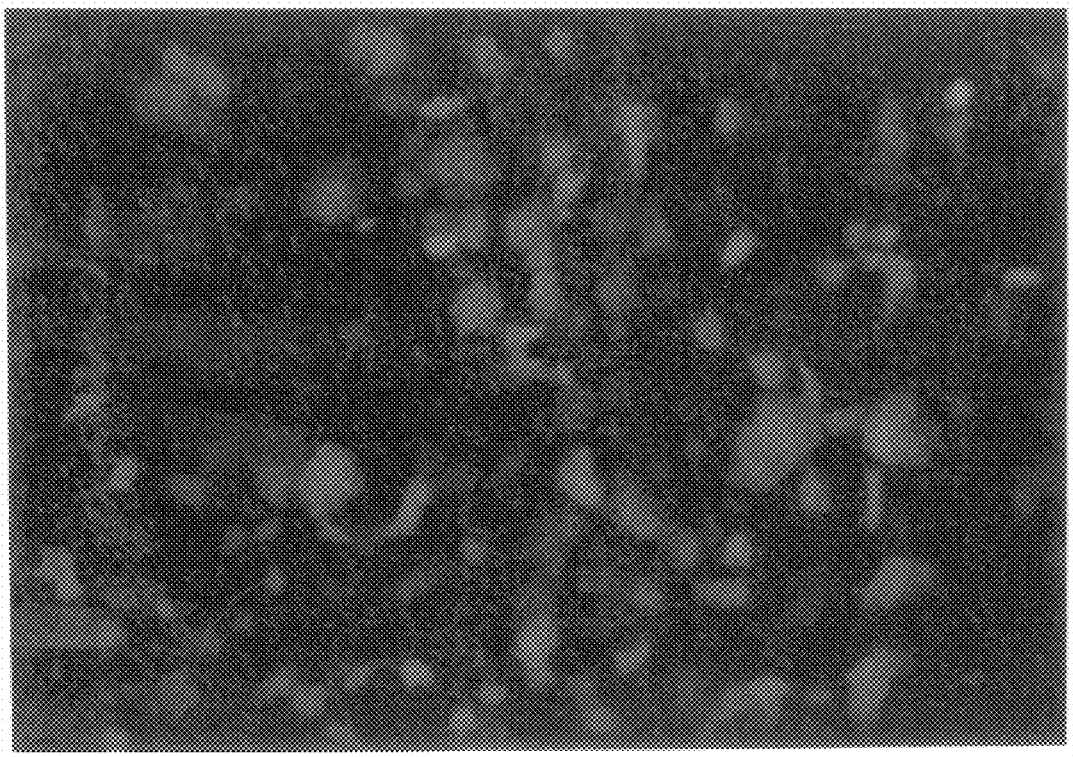
Figure 8B:
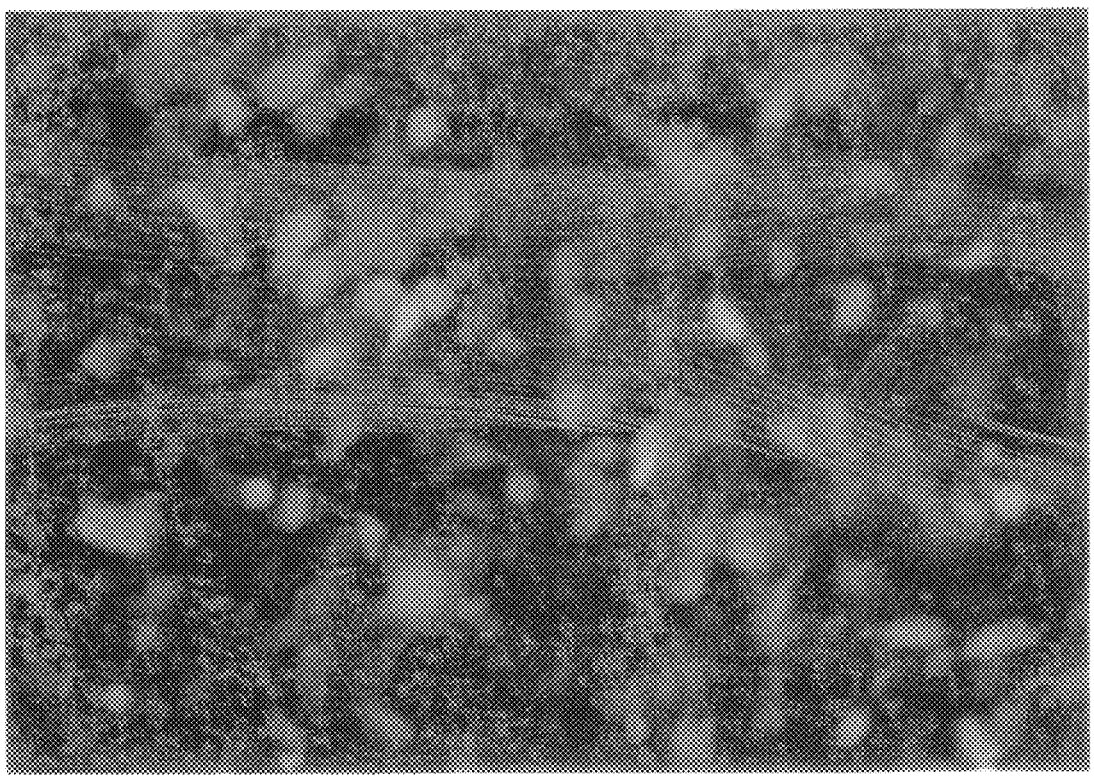
Figure 8C:
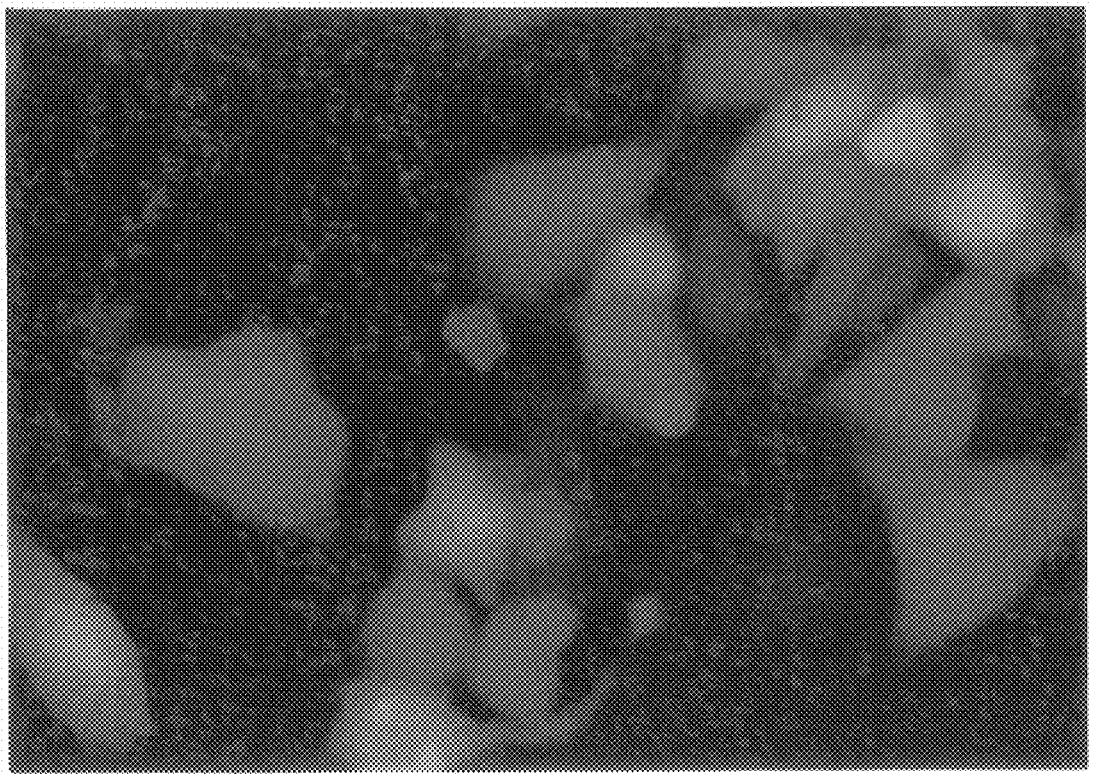

FIGS. 8A–8C depict photographs of pHE 700-hRGFP virus stock which was used to infect VA 13 normal fibroblasts (FIG. 2A), T98G human glioblastoma cells (FIG. 2B) and SV3 CRL9.7 xeroderma pigmentosum fibroblasts (FIG. 2C).

Figure 9:
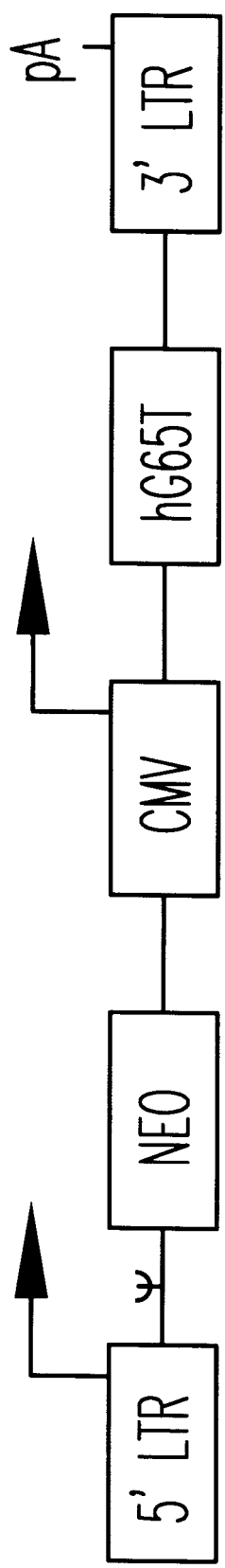

FIG. 9 is a depiction of the pLNChG65T vector.

FIGS. 10(a)–10(f) are depictions of FACS analysis of hGFP-S65T-transduced PA317 vector producer cells and human melanoma cells. All FACS analyses used the FL1 emission channel used to monitor green fluorescence. Count: Cell number counted at given fluorescence intensity; log scale represents the mean intensity of green fluorescence detected at 525 nm. 10(a) is PA317 packaging cells 98.4% negative (bar 2). 10(B) PA317-LNChG65T Cell are 95.8% positive. 10(C) A375 cells are 99.5% negative (bar 1). 10(D) A375-LNChG65T cells are 98.7% positive (bar 2). 10(E) IGROV cells are 98.9% negative (bar 1). 10(F) IGROV-LNChG65T cells are 89% positive (bar 2).

Figure 11A:
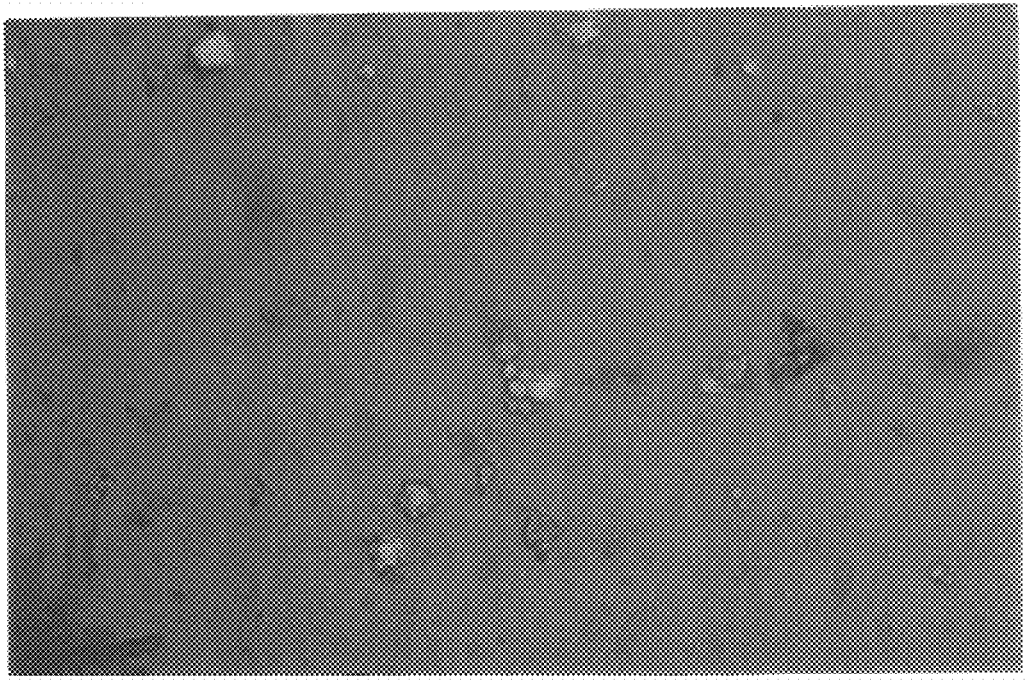
Figure 11B:
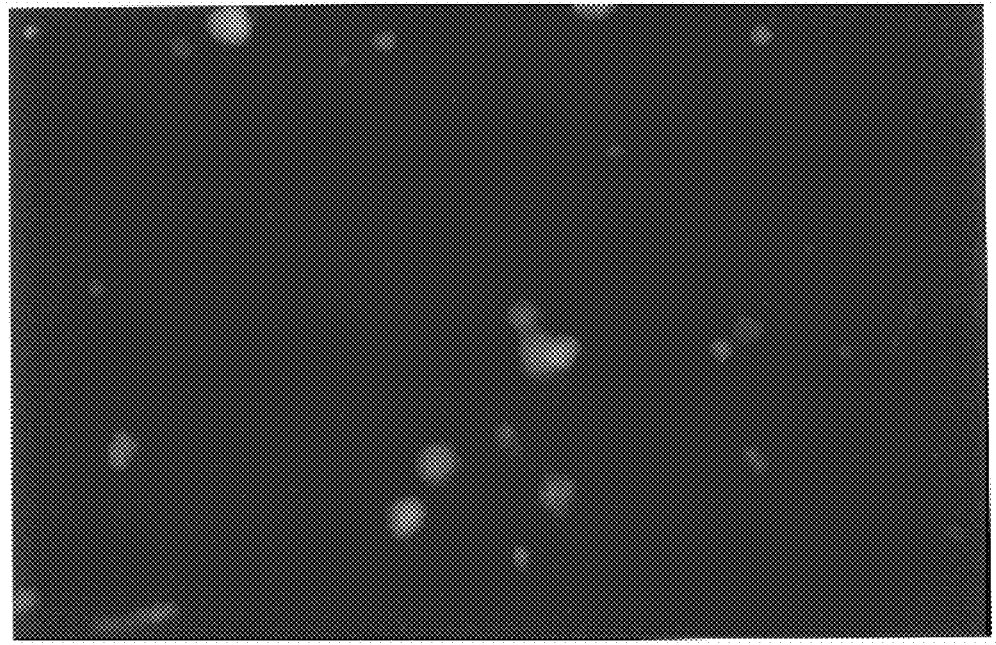

FIGS. 11(a) and 11(b) are photographs of transduced PBL immediately after completion of the transduction procedure.

Figure 12:
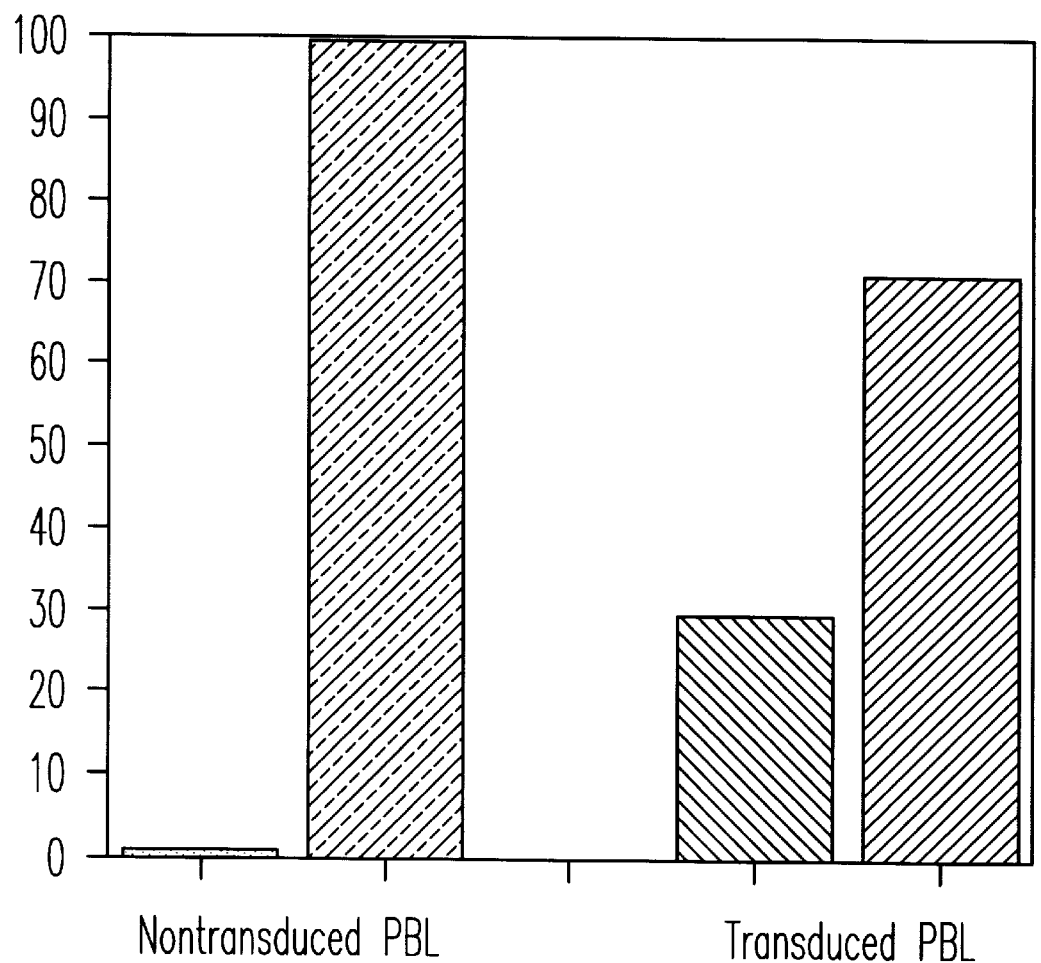
Figure 13A:
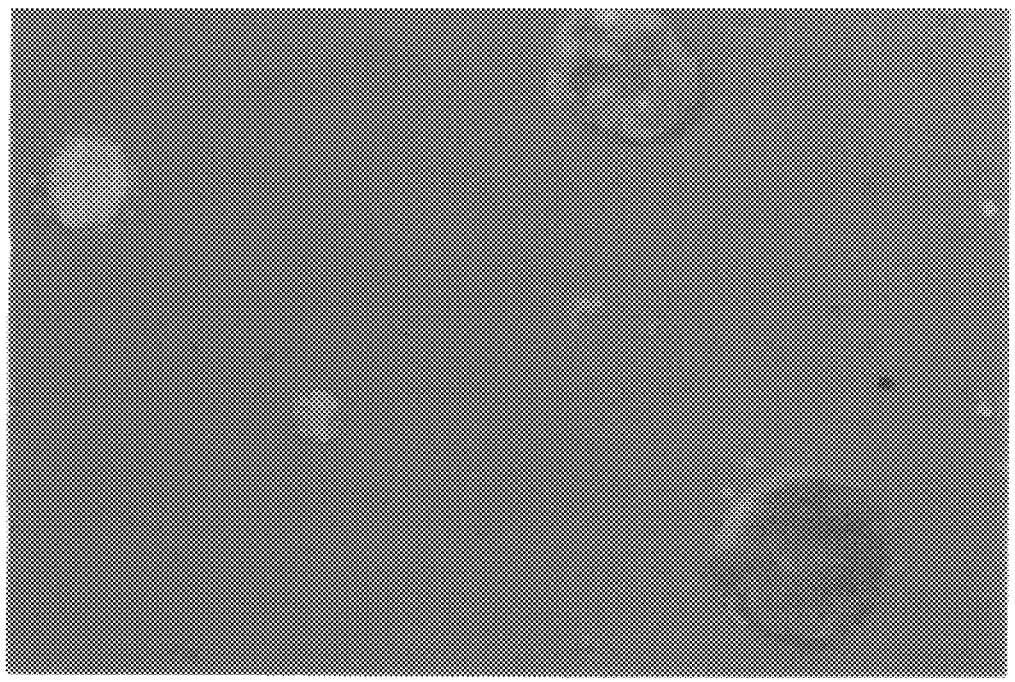
Figure 13B:

FIG. 12 is a graph depicted FACS analysis of PBL transduced with LNChG65T Vector. Dark bars show the percentage of fluorescing cells in transduced and control PBL populations at the end of the transduction procedure FIGS. 13(a) and 13(b) are photographs depicting LNChG65T transduced PBL after g418 selection and expansion.

Figure 14A:
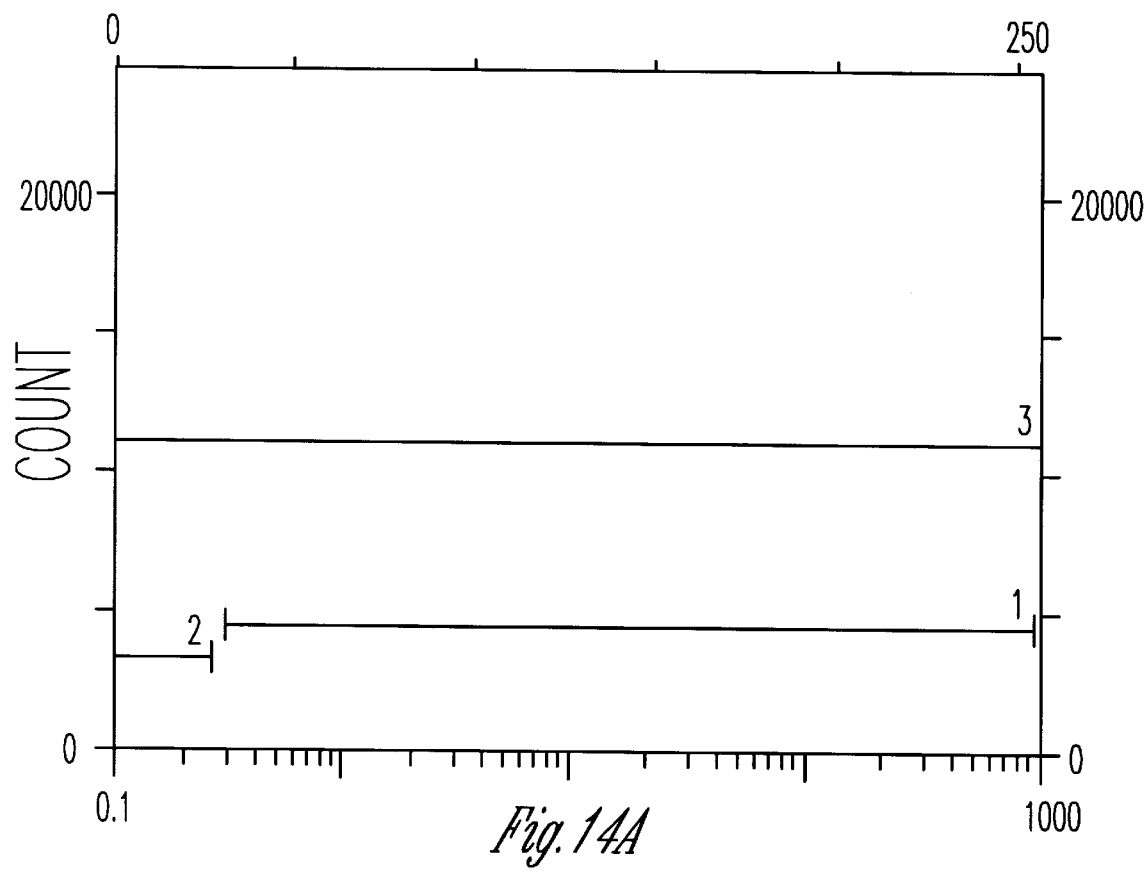
Figure 14B:
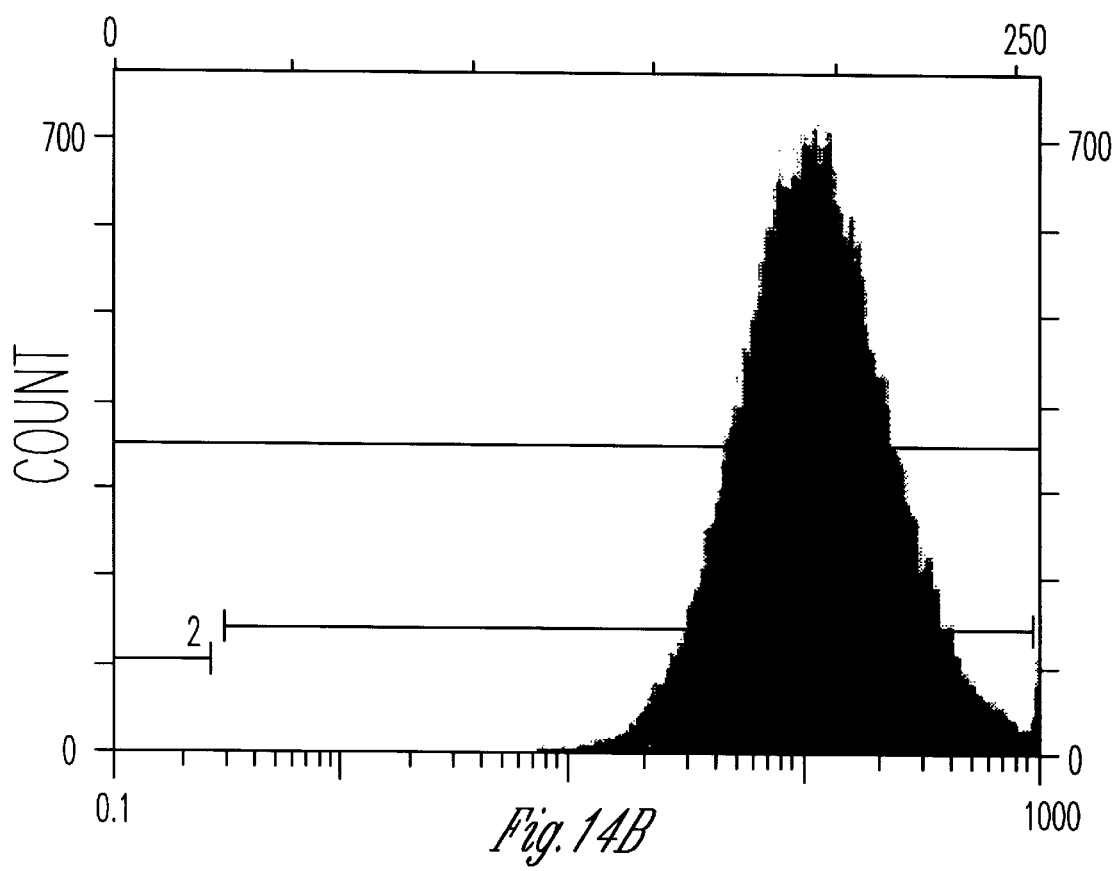

FIGS. 14(a) and 14(b) are graphs depicting the determination of activity of hRGFP in G418-selected PBL populations.

Figure 15:
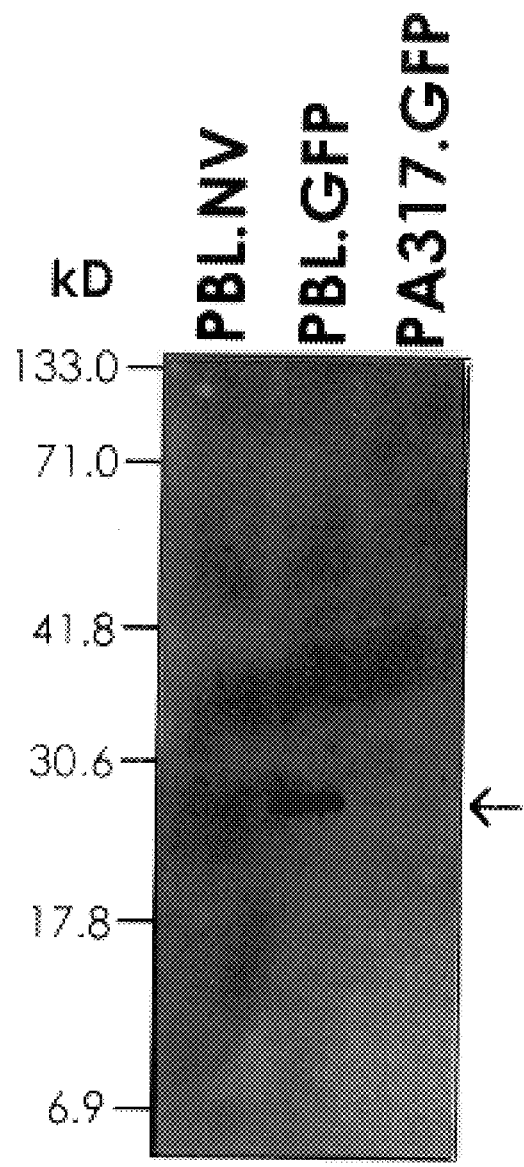

FIG. 15 is a Western Blot analysis of GFP in Peripheral Blood Lymphocytes. 1° Ab anti-GFP polyclonal antibody (1:2000 Clontech Lot #62038). 2° HRP anti-rabbit IgG (1:50000 Sigma Lot #A9189).

FIGS. 16(A)–(E) is the sequence of the plasmid vector pLEL (SEQ ID NO:2).

FIGS. 17(A)–(F) is the sequence of the plasmid vector pLESN SEQ ID NO:3).

FIGS. 18(A)–(F) is the sequence of the plasmid vector pLNCE (SEQ ID NO:5).

FIGS. 19(A)–(F) is the sequence of the plasmid vector pLNChRG (SEQ ID NO:1).

FIGS. 20(A)–(F) is the sequence of the plasmid vector PLTKOCEGFP (SEQ ID NO:6).

FIGS. 21(A)–(F) is the sequence of the plasmid vector pLNChG65T (SEQ ID NO:4).

DETAILED DESCRIPTION OF THE INVENTION

The following definitions that follow will aid in a fuller understanding and exemplification of the invention.

As used herein, "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions.

As used herein, "nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

As used herein, "recombinant expression vector" refers to a transcriptional unit comprising an assembly of (1) a genetic element or promoters or enhancers, (2) a structural or coding sequence which is transcribed into mRNA and translated into protein, and (3) appropriate transcription initiation and termination sequences. Structural units intended for use in eukaryotic expression systems preferably include a leader sequence enabling extracellular secretion of translated protein by a host cell.

A number of species use a bioluminescent GFP to emit green light after energy transfer from either luciferases or photoproteins. Prasher, D. C. (1995) *Trends Genetics* 11:320–323. The GFP gene product can function as a marker in living cells and animals and does not require a substrate (other than light) to visualize gene transfer. Chalfie, M., et al. (1994) *Science* 263:802–805. An excellent review of recent GFP applications has been provided by Prasher (supra).

Figure 1:
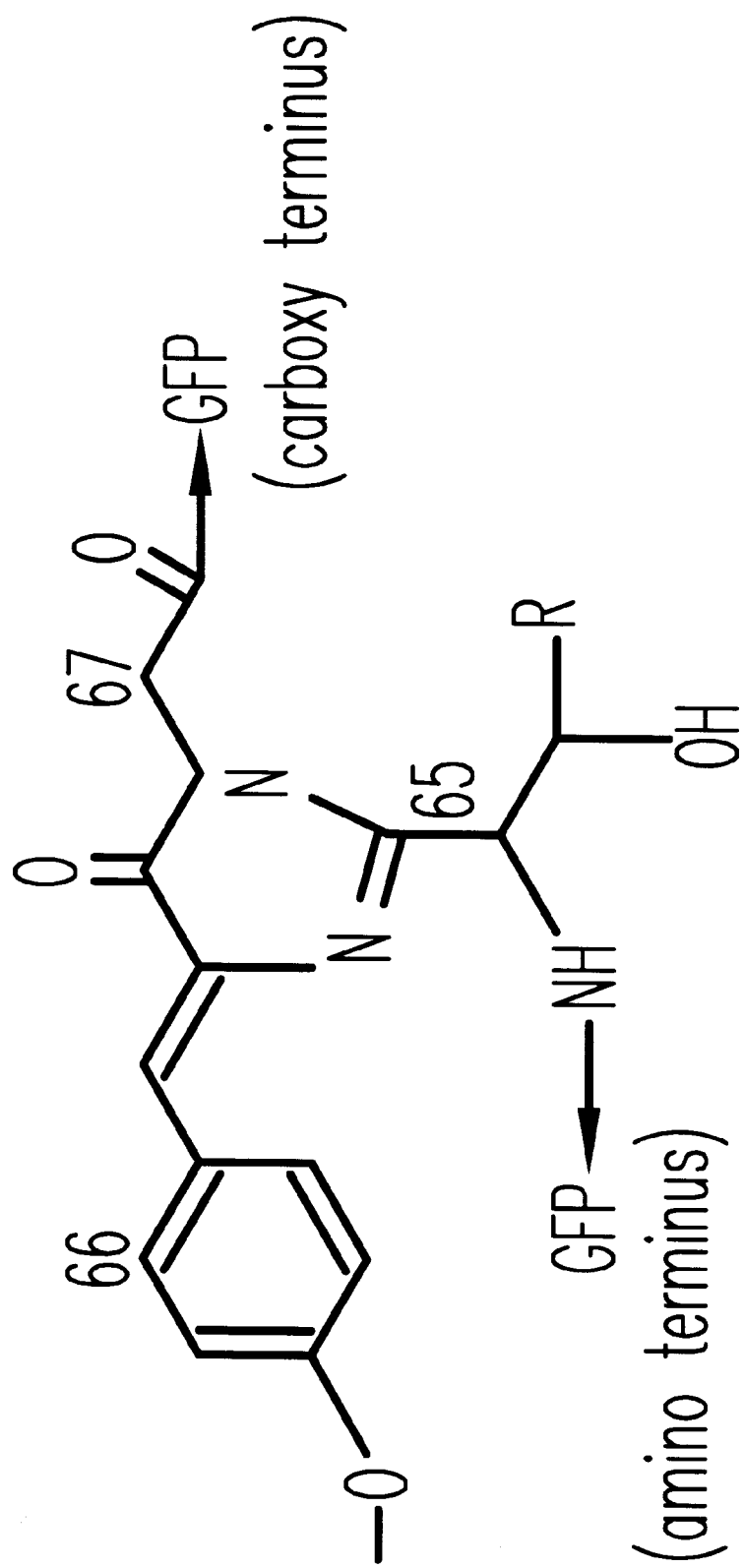
FIG. 1 is the chemical structure of the GFP fluorophore. Blue light stimulates the excitation of a cyclized wild-type GFP fluorophore formed by serine-65, tyrosine-66, and glycine-67 that emits green fluorescence after stimulation. The red shifted variant contains a mutation that converts serine-65 to threonine. This results in a "red shift" of the excitation wavelength, increased amplitude of fluorescence, and a faster rate of fluorophore formation in the mutant GFP. R=H, serine; R=CH$_3$, threonine.

The GFP cDNA is a 730 bp gene encoding a 238 amino acid polypeptide with a molecular weight of 27 Kd protein which has been cloned from the jellyfish, *A. Victoria*. Prasher, D. C., et al., (1992) *Gene* 111:229–233. GFP acts as an energy-transfer acceptor that under physiologic conditions in *A. Victoria* receives energy from an activated aequorin-coelenterazine complex. Cody, C. W., et al. (1993) *Biochemistry* 32:1212–1218. The chromophore is produced from autocyclization of three residues, serine-65, dehydrotyrosine-66, and glycine-67. Cody, C. W., et al. (1993) (supra). GFP protein is inactive until cyclization and oxidation of these three residues to generate a p-hydroxybenzylideneimadazolidinone chromophore (see FIG. 1). Molecular oxygen is required for fluorophore formation. Heim, R., et al. (1994) *Proc Natl Acad Sci* 91:12501–12504.

GFP was found to have extremely stable fluorescence in vitro after stimulation with blue light. Prasher, D. C., et al. (1992) (supra). Upon exposure to blue light, the protein emits a beautiful bold green light. Living eukaryotic cells expressing the protein may be visualized with the aid of a fluorescent microscope containing a GFP cube with excitation at 420–470 nm and emission at 490→600 nm. Cells may be returned to tissue culture without any apparent damage (Levy, unpublished results). There is no need for fixation, staining, antibodies, or drug selection, making GFP an extremely valuable tool for following gene transfer in living systems.

The GFP fluorphore can be column purified, renatured and crystallized and still maintain its fluorescent characteristics. Ward, W. W., et al. (1982) *Biochemistry* 21:4535–4540. These results prompted expression studies of wild-type GFP in prokaryotic and eukaryotic cells. These basic understandings of GFP mechanistic properties have led in turn to additional modifications to extend its usefulness to other systems.

Recently, a gain of function mutant GFP gene was generated that altered the serine-65 codon to a threonine codon resulting in a protein which fluoresces quicker with emission amplitudes from 4 to 6 fold greater than the wild-type gene. Heim, R., et al. (1995) *Nature* 373:663–664. This improved version of GFP has been termed the red shifted GFP because the excitation peak has shifted to the red zone of 470–490 nm. The emission remains green. Recently, more involved genetic modifications of the GFP sequence have been investigated.

A few investigators have "humanized" the wild-type codons to those used more commonly in mammals. Dr. Sergei Zolotukhin and Dr. Nicholas Muzyczka, University of Florida (unpublished results). *A. Victoria* is classified in the phylum Ctenophora and its codon usage is significantly different from mammals. Due to differences in codon usage, mammalian cells may not efficiently translate wild-type GFP transcripts. This latest version is termed the "humanized" red shift GFP(HRGFP).

A humanized GFP is available from Clontech, Inc. therefore (see page 29). Further, those of skill in the art will appreciate that other variations may be created so that human codon usage is proscribed to achieve the desired amino acid sequence. The inventors have now cloned the HRGFP into viral and retroviral systems to provide a means of easily following gene transfer which is also quite beautiful to the eye.

The structure and life cycle of retroviruses make them ideally suited to be gene-transfer vehicles since (i) the majority of sequences coding for their structural genes are deleted and replaced by the gene(s) of interest which are transcribed under control of the retroviral regulatory sequences within its long, terminal repeat region and (ii) they replicate through a DNA intermediate that integrates into the host genome. Although the sites of integration appear to be random with respect to the host genome, the provirus integrates with a defined structure in low copy number. Most of the viral gene sequences can function when supplied in trans. For general information regarding retroviral mediated gene transfer, see McLachlin, et al. (1990) *Progress in Nucleic Acid Research and Molecular Biology* 38:91–135.

Retroviruses are viruses which carry their genetic information in the form of RNA. Once the virus infects a cell, the RNA genome is reverse-transcribed into the DNA form, which integrates into the genomic DNA of the infected cell. The integrated DNA form is called a provirus and the gene order within this provirus is always maintained. The retroviral genome and the proviral DNA have three genes: the gag, the pol and the env, which are flanked by two long terminal repeat sequences (LTRs). The gag gene encodes the internal structural (nucleocapsid) proteins, the pol gene encodes the RNA-directed DNA polymerase (reverse transcriptase), and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site). Mulligan, R. C. (1984) *Proceedings of the National Academy of Sciences, U.S.A.* 81:6349–6353.

In order to generate a viral particle containing the recombinant genome, it is necessary to develop cell lines that provide packaging "help". To accomplish this, a plasmid encoding for example, the retroviral structural genes gag, pol, and env, is introduced into an otherwise untransformed tissue cell line by conventional calcium-phosphate-mediated DNA transfection. These plasmid containing cells are referred to as a packaging cell line. This plasmid containing packaging cell line can be maintained as such or a replication incompetent retroviral vector can be introduced into the cell's genome. In the latter case, the genomic RNA generated by the vector proteins of the packaging line results in the release of retroviral particles into the culture medium. A stable cell line containing the structural gene sequences of the retroviruses is a retroviral "producer cell line."

Because genes can be introduced into progenitor cells using a retroviral vector, they can be "on" (subject to) the retroviral vector control. In such a case, the gene of interest is transcribed from a retroviral promoter. A promoter is a specific nucleotide sequence recognized by RNA polymerase molecules that start RNA synthesis. Alternatively, retroviral vectors having additional promoter elements (in addition to the promoter incorporate in the recombinant retrovirus) which are responsible for the transcription of the genetic material of interest, can be used.

Almost all retroviral vector systems consist of two components: (i) the recombinant retroviral vector molecule that carries the gene(s) of interest and (ii) construct(s) providing retroviral structural proteins in trans. Together, these two components allow the production of recombinant viral particles capable of infecting target cells.

Retroviral vectors are derivatives of wild-type, replication-competent retroviruses in which part of the retroviral coding information (gag, pol, env) has been replaced by the gene(s) to be transferred to the target cell. Usually, these vectors contain at least two heterologous genes: (i) a marker gene that confers a selectable advantage upon infected cells, allowing their easy positive selection, and (ii) the therapeutic gene to be transferred. The two genes can either be expressed from the same retroviral promoter where the natural splicing mechanism of the retrovirus is utilized to generate different RNAs from which the gene products are separately expressed, or from different promoters, one from the retrovirus itself and one introduced along with the gene construct.

Recently, dicistronic retroviral vectors have been described in which two gene products are translated from one mRNA. See for e.g. Levine, et al. (1991), *Gene* 108:167–174. Dicistronic retroviral vectors have been reported to produce higher virus titers, to permit the insertion of larger genes, and to show more stable expression of transferred genes when compared to a two-gene, two-promoter vector. Id.

The present invention also contemplates the use of vehicles other than retroviruses to genetically engineer or modify cell lines. Genetic information of interest can be introduced by means of any virus which can express the new genetic material in such cells. Examples of such viruses include but are not limited to SV40, herpes virus, adenovirus, and human papilloma virus.

The first generation of packaging cell line is typified by the ψ-2 and ψ-am cell lines. Mann, et al. (1983) *Cell* 33:153–159; Cone, R. D., et al. (1984) *Proc. Natl. Acad. Sci.* 81:6349–6353. These cell lines contain a Mo-MuLV provirus that carries a simple deletion in the ψ packaging signal. This packaging construct gives rise to Mo-MuLV transcripts that direct the synthesis of authentic viral gag, pol, and env proteins, but the deletion in the ψ signal precludes the packaging of the genomic-length RNA into virion particles. Ecotropic virus is produced from ψ-2 cells, whereas the ψ-am cells produce amphotropic virus that shows an extended host range. Unfortunately, such cell lines still give rise to wild-type virus at a relatively high frequency because a single recombination event between the packaging construct and the vector construct, which of necessity must carry the ψ signal, will suffice to produce a wild-type genome. Miller, A., et al. (1986) *Int. J. Cancer* 37:173–177.

To reduce the risks of generating wild-type, replication-competent virus, a second generation of retroviral vector system carrying mutations in the LTR of the packaging construct has been constructed so that additional recombination events are required before a replication competent virus can be produced. The packaging cell line PA317 carries an amphotropic provirus, which in addition to the ψ region deletion, lacks part of the 5' LTR and the 3' LTR has been replaced with the polyadenylation signal from SV 40. Thus, at least two recombination events are required to generate replication competent virus.

In gene therapy, the retroviral vector should only infect the cells in which the defect manifests itself and is thus involved in causing the disease. Thus, the expression of the introduced gene should be controlled by regulatory elements that target the expression to the relevant cell type. Replication-competent virus may have to be used for this approach, particularly if the cells of a multicellular organ or dense tumor mass are to be the target or if very high virus titers are required. Also, to prevent unsolicited replication of the retrovirus during or after gene therapy, vectors should be designed that can be conditionally silenced or inactivated.

Amphotropic MuLVs are able to infect cells of most species including rodents and humans. This observed tropism is determined by the env protein of the MuLV together with the availability of the corresponding receptor on the target cell. The env protein of ecotropic Mo-MuLV, gp70, interacts with a cationic amino acid transporter, which serves as the host cell receptor and is expressed in many tissues with the notable exceptions of liver, heart, and muscle. Kim, et al., (1991) *Nature* 352:725–728.

It has also been shown that it is possible to limit the infection spectrum of the Mo-MuLV virus and consequently of Mo-MuLV-based vectors. One approach involves the coupling of antibodies, directed against known proteins that are expressed on the surface of the target cell, to antibodies specific for the virus env protein via streptavidin.

A second strategy for targeting the infection spectrum of retroviral vectors involves the chemical coupling of ligands to the viral env proteins. Viral env proteins can be artificially converted to asialoglycoproteins by coupling them to lactose. Neda, et al., (1991) *J. Biol. Chem.* 266:14143–14146.

Another means of targeting the infection spectrum involves the co-expression of other ligands on the virus surface along with the normal env SU proteins. This strategy would allow normal viral internalization and should also result in a favored uptake by cells expressing the receptor for the co-expressed ligand.

The above disclosure reveals that the GFP has an enormous potential in the field of retroviral and viral gene therapy. Constructs using the wild-type gene in other aspects of biology have already proven to be valuable. Until now, these constructs have proven to be limited in retroviral vectors due to the low levels of expression in stable cell lines. The HS65T has overcome this barrier and provided an astounding display of bioluminescence.

The key to expression seems to lie in the 3 amino acid residues which form a cyclized chromophore. Specifically, the serine at position 65 is a site at which several amino acid replacements show increased intensity and quicken the rate of chromophore formation. The red shift may be responsible for advancing expression to this level. However, humanizing of the coding sequences seems to be providing the dominant contribution. Jellyfish are extremely divergent from mammals and consequently have different codon usage. This may present a translation challenge for mammalian cells of enough proportion to prevent a build up of detectable GFP. The HGS65T GFP gene contains 169 codon changes (Clonetech) representing 71% of the gene. The above results show that this is a superior marker gene to follow retroviral and viral transduction.

In transducing and subsequent selection, it can be determined whether the cells have completed selection or not. In addition, it is possible to determine transduction efficiency in a variety of cell lines. It is expected that the satisfactory expression of GFP is achievable in many other types of mammalian cell lines, including other types of human tumor lines, based on similarities in cell morphology and physiology. Such cell lines can be readily ascertained by those of ordinary skill in the art.

In vivo retroviral transduction experiments may also take advantage of this marker system. PA317-HGS65T VPC cells injected into an established subcutaneous tumor cell will transduce the dividing tumor cells. VPC's used in black mice systems will be destroyed by the immune system within 2 weeks after injection. The F.A.C.S. sorting capabilities also opens up some doors of opportunity for leukemia trials. Overall, this evidence demonstrated that humanized red shift GFP has the potential of becoming a major player in gene therapy.

The instant invention demonstrates the effectiveness of a humanized, red shifted mutant GFP by retroviral and viral mediated gene transfer into human tumor cells and murine fibroblasts. A few molecular genetics groups have now reported mutations of the wild-type GFP gene which can generate GFP gene products with modified excitation and emission spectra. See for e.g. Heim, R., et al. (1994) *Proc Natl Acad Sci. USA* 91:12501–12504. The longer wavelength excitation peak (475 nm) of native *A. Victoria* GFP has lower amplitude than its shorter wavelength excitation peak (470–490 nm) with fluorescence amplitudes from 4–6 fold greater than from the wild-type gene product. Heim, R. (1995) *Nature* 373:663–664. Interestingly, this mutant also had more rapid formation of the fluorochrome. Id. Furthermore, the mutated, red shifted GFP had its codons modified to usage common in mammals (Dr. Sergei Zolotukhi and Dr. Nicholas Muzyczka, University of Florida, unpublished results). The inventors have evaluated this humanized version of a serine-65 to threonine codon mutant that demonstrates excitation at 490 nm and emissions at 510 nm in current gene transfer experiments. Comparisons between the wild-type GFP and the humanized, serine-65 red shifted mutant (hRGFP) demonstrated substantial improvement in fluorescence expression after either transfection and retroviral mediated GFP gene transfer (Table 1).

Wild-type GFP alone and GFP containing fusion proteins have been demonstrated in mammalian cells to provide efficient marking of protein trafficking and gene expression. GFP has also been fused to chromogranin B and fluorescence could be observed in the Golgi apparatus after temperature block at 15° C. Kaether, C., et al. (1995) *FEBS Lett.* 369:267–271. Fluorescence can also be detected after the transient transfection of wild-type GFP, GFP fused to the PML proto-oncogene product, or GFP fused to a human glucocorticoid receptor expressed in COS-1 cells, chicken embryonic retinal cells, and EPC cells (carp). Ogawa, H., et al. (1995) *Proc Natl Acad Sci. USA* 92:11899–11903. Native GFP has also been fused to the microtubule associated protein 4 (MAP 4) gene and permitted the tracking of subcellular reorganization of cytoskeletal elements. Olson, K.R., et al. (1995) *J Cell Biol.* 130:639–650. Wild-type GFP has been fused to the N-methyl-D-aspartate (NMDA) receptor subunit green fluorescence. Marshall, J., et al. (1995) *Neuron* 14:211–215. Fluorescence was detected in cells transfected with GFP alone. The investigators demonstrated NMDAR-1 gene activity by patch clamp analysis after fusion gene transfer. Id. These results demonstrate that the transient transfection of wild-type GFP or chimeric proteins containing GFP can function as an excellent intracellular marker in living cells for proteins and can be used to visualize cell organelle. Of note, these experiments used transient transfection to obtain very high levels of wild-type GFP expression. The present disclosure is in agreement with these results in that transient transfection which transfers multiple transgene copies of wild-type GFP expression cassettes were easily visualized, but the inventors found that stable transduced cells with single transgene copy of wild-type GFP could never be visualized by fluorescence microscopy (Table 1). However, the present invention demonstrates that a humanized, red shifted GFP transgene in single copy can produce excellent fluorescence (FIG. 5).

Transgenic mice have been produced expressing a slightly modified wild-type GFP expressed from the chicken β-actin promoter. Ikawa, M., et al. (1995) *Develop Growth Differ.* 37:455–459. The fingers or tails of these transgenic mice were distinguishable as green under a fluorescent microscope and homogenized tissue from the muscle, pancreas, lung, and kidney demonstrated fluorescence after excitation with 490 nm light. The visualization of vector gene expression in living transduced tissues with hRGFP may become an outstanding method for studying in vivo gene transfer used in human clinical trials.

The present invention demonstrates the ability to analyze and easily detect living, retroviral transduced cells without the need for cell fixation or antibodies. This allows for the clinical application of this marker in living tissue by using the appropriate enhancer/promoter or targeted transduction procedure. This may be particularly useful in bone marrow processing, lymphocyte sorting, and other applications requiring the FACS analysis of living cells. Further, since the GFP gene has not been shown to have any cytotoxicity in vitro, it is expected that the GFP gene will be safe for in vivo use. Future directions will lead to a wider range of useful GFP based mutant proteins with well defined fluorophores with characterized excitation and emission spectra, using mammalian codon usage. For example, Heim and colleagues subjected the native GFP sequence to random mutations in bacteria and developed a series of interesting mutants with altered excitation peaks and found that a substitution of Tyrosine-66 to histidine generated a mutant GFP that demonstrated blue fluorescent emission. Heim, R., et al. (1994) *Proc Natl Acad Sci, USA* 91:12501–12504. This may permit two color separation and analysis of living cells by FACS.

According to the invention retroviral vectors have been prepared which comprise a humanized, red shifted green fluorescent protein (hrGFP) transcription unit comprising a promoter, a gene which encodes humanized red-shifted green fluorescent protein, and a termination or polyadenylation signal sequence. Optionally the transcription unit may contain enhancer elements.

The transcription unit is a part of a retroviral vector construct, a DNA or RNA segment which comprises a viral packaging sequence and optionally a viral long terminal repeat sequence.

In a preferred embodiment the construct also comprises a selectable marker gene such as an antibiotic resistance gene including the ampicillin resistance gene, tetracycline resistance gene, neomycin resistance gene, or any other resistance gene known to those of skill in the art. See generally Maniantis "Molecular Cloning" 2nd ed., Cold Spring Harbor Press (1989) the disclosure of which is incorporated by reference. The selectable marker gene can be embodied within the GFP transcription unit, can be a separate transcription unit, or can include one or more components of the GFP transcription unit.

Figure 2:
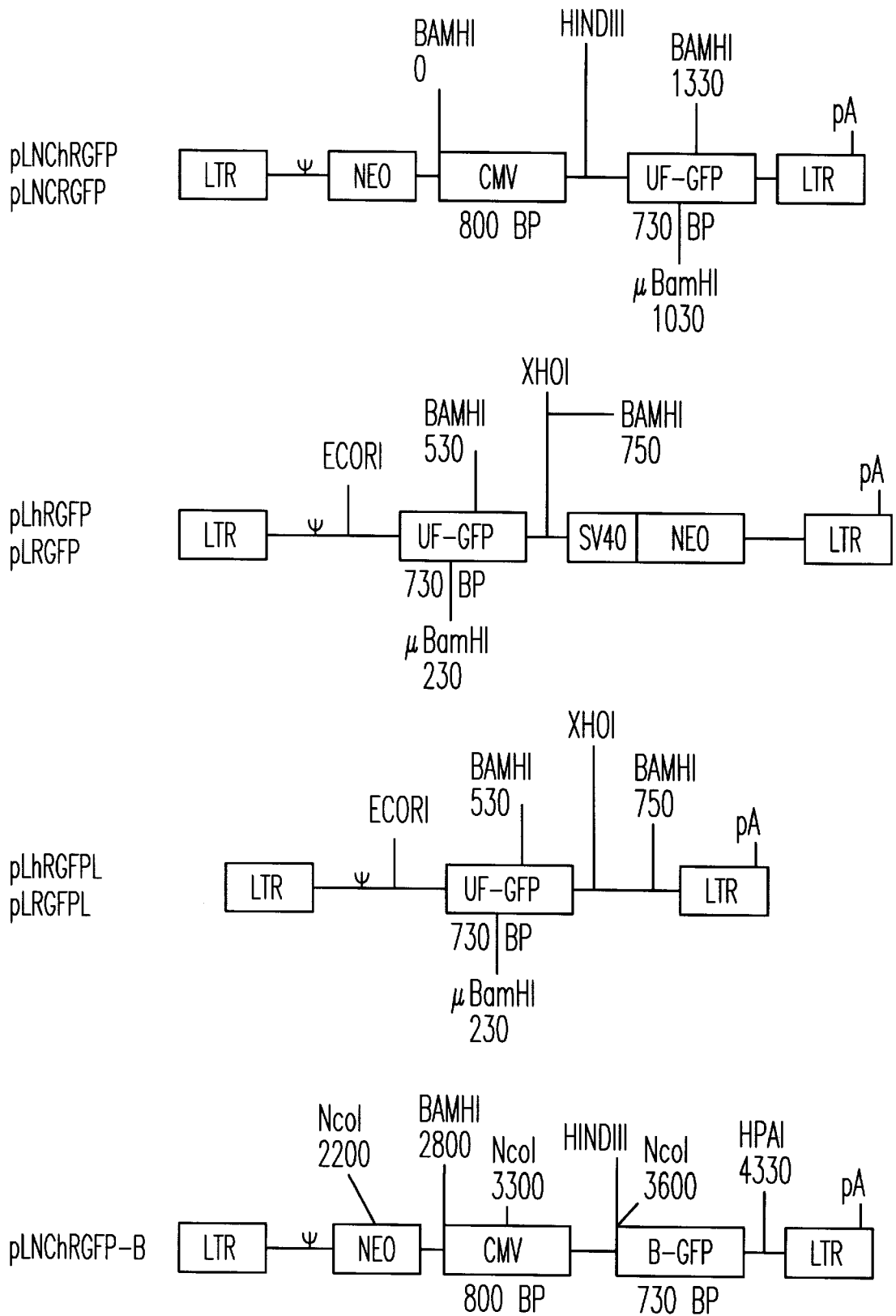
FIG. 2 shows the retroviral constructs containing the red shift, humanized Green Fluorescent Protein. The wild-type GFP and the humanized, red shifted GFP gene were cloned into the pLNCX retroviral backbone. Plasmid pLNCG was constructed by PCR amplification of a wild-type GFP containing DNA fragment and subsequent subcloning into pLNCX. LTR, long terminal repeat; pA, polyadenylation signal; arrows indicate transcriptional start sites; Ψ$^+$ indicates the presence of the viral packaging sequence; GFP, wild-type green fluorescent protein; hRGFP, humanized, red shifted GFP.

In a most preferred embodiment the construct comprises the elements depicted in FIG. 2, the pLNChRGFP, pLNCRGFP, pLhRGFP, pLRGFP, pLhRGFPL, plRGFPL or pLNChRGFP-B constructs.

The components described herein can be arranged in any order and vectors having the same components in a different order are intended to be within the scope of the invention. The only requirement is that transcription units including a gene the expression of which is desired must include a promoter and a termination signal in functional arrangement to the gene to be expressed after the sequence. A transcription unit can comprise more than one coding gene or can contain a second transcription unit within a larger unit that may share a common termination signal or promoter sequence. The vectors of the invention provide for stable long term transfection to recipient cells with detectable fluorescence with only single copy expression. This provides for a number of protocols including fluorescence activated cell sorting (FACS) for separation of transfected from nontransfected cells for ex vivo gene therapy techniques, which cells are harvested, transformed and then re-introduced. One such method involves bone marrow purging with transformation of lymphocytes as shown in the Examples section. Any ex vivo gene therapy application which involves selection of successfully transformed cells is applicable.

The following examples describe the cloning and characterization of ecotrophic and amphotropic retroviral vectors capable of demonstrating efficient, stable transfer of an hRGFP gene into mammalian cells. They are for informational purposes only and are not intended to limit the scope of the present invention in any manner.

EXAMPLE 1

Retroviral Mediated Gene Transfer into Human Melonoma Tumor Cells and Murine Fibroblasts Experimental Protocol Cell Culture. A375 is a human melanoma cell line (ATCC, Manassas, Va.). PA317 is a murine amphotropic, retroviral vector packaging cell line (kindly provided by A. D. Miller, University of Washington). Cells. were grown in RPMI supplemented with 10% fetal calf serum (FCS) (all obtained from Gibco BRL) in monolayers at 37° C. and 5% $CO_2$. All cells were passaged and harvested by standard trypsin (Gibco BRL) digestion at 37° C. Cells were routinely passaged at 80–90% confluence.

Plasmid preparation and digoxin probes. Plasmid pGFP-C1 containing wild-type GFP was obtained from Clontech (Palo Alto, Calif.). The plasmid pTR-UF2 containing the humanized red, shifted GFP (hRGFP) gene was kindly provided by Dr. Sergei Zolotukhin and Dr. Nicholas Muzyczka (University of Florida). Construct plasmid DNA was transformed into DH5a competent cells and colonies grown on L-broth supplemented with ampicillin (50 µg/ml) plates (LB/AMP) and transferred onto nylon membranes. The membrane was proved with a Dig-GFP probe using a digoxin probe kit (Boehringer-Mannaheim). Primers for the Dig-GFP probe amplification of a GFP fragment were 5' primer 5' GGG AAG CTT TTA TTA TTT GTA TAG TTC ATC CAT GCC (SEQ ID NO:7) and 3' primer 5' GGG AAG CTT GCG CGT ATG GGT AAA GGA GAA GAA CTT (SEQ ID NO:8). Positive colonies were grown up in LB/AMP broth and plasmid DNA was isolated using the Qiagen plasmid prep kits (Qiagen Corp., Chatsworth, Calif.).

Construction of GFP retroviral vectors. Primers were made to amplify the 5' end of the CMV promoter/enhancer and the 3' end of the wild-type GFP gene from the GFP-C1 vector (Clontech, Palo Alto, Calif.). The 5' primer includes unique Xba I, Bam HI, and Not I restriction enzyme sites: 5' GGA TCT AGA GGA TCC GCG GCC GCC TAG TTA TTA ATA GTA ATC AAT TAC GGG GTC (SEQ ID NO:9). The 3' primer includes 3 in frame stop codons followed by a Hind III restriction enzyme site: 5'GGA AAG CTT CTA TCA TTA TTG AGC TCG AGA TCT GAG TCC GGA CTT GTA (SEQ ID NO:10). The 1.3 Kb CMV-GFP PCR product was cloned into PCR3-cloning vector (Invitrogen) to generate plasmid pPCR3CG-14. The 1.3 Kb fragment containing the CMV promoter and GFP gene was gel isolated (Jetsorb, Genomed) from the pPCR3CG-14 vector using Bam HI and Hind III restriction digest. The 800 bp retroviral CMV promoter was directionally cloned to generate the pLNCG construct. Finally, plasmid pTR-UF2 was restriction digested with Not I and the 730 bp DNA fragment containing the humanized red shift GFP open reading frame was isolated. After Klenow treatment, the blunt ended DNA was ligated into pLNCX at the Hpa I site. The resulting plasmid was designated pLNChRG.

Fluorescent detection of green fluorescent protein expressing cells. We visualized GFP expressing cells with a Nikon Labophot-2 Fluorescent Microscope (Fryer Company, Inc.). The cube used in the microscope was either the Green Fluorescent Protein Longpass 41015 filter set (excitation at 420–470 nm and emission at 490 to >600 nm) for the wild-type GFP detection (Chroma Technology Corporation) or the FITC dichromic filter set (excitation at 450–490 nm and emission at 520 nm) for the hRGFP detection (Fryer Company, Inc.). Photographs were taken using the Nikon Microflex UFX-DX and AFX-DX systems (Fryer Company, Inc.).

Transient expression of GFP. PA317 cells were seeded on a sterilized coverslip in a 6 well dish 12–24 hours before transfection. Cells were at 30–50% confluence at the time of DNA transfection. Five µg of DNA and 15 µl of DOTAP reagent (Boehringer Mannheim) was used as per the manufacturer's protocol. The mixture was added to the plates containing either RPMI 1640 with 10% FBS, L-glutamine, and penicillin/streptomycin or in serum free media. After 10–18 hours the media was replaced with RPMI with 10% FCS. The coverslip containing the cells was placed on a slide and examined for fluorescence 9–48 hours after transfection. The cells remaining in the well (after the coverslip was removed) were trypsin digested and transferred to tissue culture dishes. After attachment these cells were placed under selection with G418 (1 mg/ml) for 10–14 days.

Construction, subcloning, and titering of LNCG and LNCHRG vector producer cell lines. The plasmid pLNCG or pLNChRG were transfected with DOTAP into the amphotropic retroviral packaging line PA317. Twenty-four hours later, the cells were placed under selection with G418 (1 mg/ml) for 2 weeks. LNCG or LNChRG VPC were grown to approximately 90% confluence and supernates were removed to transduce A375 target cells. Retroviral supernates were filtered through 0.45 μm filters (Nalgene), supplemented with 10 μg/ml of protamine sulfate (Elkins-Sinn) and used to transduce A375 melanoma or NIH3T3tk– fibroblast cells. The target A375 melanoma or NIH3T3tk– cells were 40–60% confluent when transduced. Twenty-four hours after the final transduction cells were placed under G418 (1 mg/ml) selection for 2 weeks. Cells were examined under the fluorescence microscopy after reseeding the cells onto glass cover slips.

Fluorescence activated cell sorter analysis of transduced human cells. Cytometry of stable hRGFP transfected or transduced cells was performed on a Epics Profile II analyzer. Cells were analyzed using a 525 nm band pass filter set (Part #814036, Coulter Corp.). Cultures of nontransfected PA317 cells, LNChRG transfected PA317 cells, nontransduced A375 cells, or LNChRG transduced A375 cells that were 80–90% confluent were trypsin digested washed with RPMI with 10% FCS and resuspended at a concentration of approximately $1 \times 10^6$ cells/ml. All FACS analysis used the FL1 emission channel to monitor green fluorescence (normally a FITC monitor).

Figure 3A:
FIGS. 3A–3C relate to GFP detection in transfected cell lines. The photographs show the expression of GFP and hRGFP in mouse PA317 packaging cells.
Figure 3B:
Figure 3C:

Transfected cell lines. PA317 retroviral packaging cells and A375 melanoma cells were transiently transfected with pLNCG or pLNChRG plasmids (FIG. 3). These two constructs led to significantly different levels of fluorescence after transient transfection (Table 1). Nontransfected PA317 cells did not demonstrate green fluorescence (FIG. 3A). Transfected cells containing the wild-type GFP gene (pLNCG) exhibited a fluorescence in <2% of the cell population that was detected after 48 hours (FIG. 3B). However, once the humanized, red shift GFP retroviral construct (pLNChRG) was transfected the results were outstanding. Fluorescence can be detected as early as 9 hours post-transfection. By 36 hours, 30–40% or more of the cells are easily visualized, and contain enough protein to produce an intense fluorescence (FIG. 3C). Overall, with the fluorescence detection filters used, pLNChRG transfected cells had enhanced fluorescent intensity and efficiency compared to cells transfected with wild-type GFP plasmid (pLNCG). The inventors did not observe any cytopathic or growth inhibiting effect due to GFP or hRGFP in transfected cells.

Stable LNCG and LNChRG retroviral vector producer cells. Stable LNCG or LNChRG PA317 VPC were generated by lipofection with the pLNCG or pLNChRG plasmids, respectively. Transfected PA317 cells were selected in media containing G418 (1 mg/ml). These stable LNCG or LNChRG PA317 VPC were examined by fluorescence microscopy. The LNCG PA317 VPC line that contains the wild-type GFP gene demonstrated no fluorescence after excitation with 420–470 nm light (data not shown). The inventors therefore analyzed the LNCG VPC line by PCR using GFP amplifiers to detect host chromosomal integration of the LNCG vector. The GFP gene was present in all lines tested, despite the fact that no fluorescence occurred (data not shown). In striking contrast, the LNChRG PA317 VPC line demonstrated vibrant green fluorescence in nearly 100% of the cells after G418 selection (FIG. 4). The intensity of fluorescence in the LNChRG VPC line was capable of highlighting many subcellular organelles.

Detection in LNChRG transduced A375 melanoma and NIH3T3tk-transduced cell lines. Supernates from cultures of LNCG or LNChRG PA317 VPC were collected when the cells were 90–100% confluent. Supernates were filtered and transferred into tissue culture plates containing A375 melanoma cells or NIH3T3tk-cells. Twenty-four hours after the final exposure to retroviral supernates, the target cells were placed under selection with media containing G418. With this gene transfer system, most cells will contain only one integrated copy of the retroviral vector (C. Link, unpublished results). A375 cells transduced by LNCG VPC demonstrated no evidence of fluorescence despite the fact that PCR revealed the presence of GFP in the cellular genome (data not shown). However, the $neo^r$ gene transferred by the LNCG vector was functional, since the A375 cell colonies were G418 resistant. In contrast, the LNChRG vector transduced A375 melanoma cells had bright fluorescent activity (FIG. 5A). Similarly, murine NIH3T3tk– fibroblasts transduced with the LNChRG retroviral vector demonstrated strong fluorescence in nearly 100% of the cells (FIG. 5B). The inventors did not observe any cytopathic or growth inhibiting effect due to GFP or hRGFP in transduced cells.

Figure 6A:
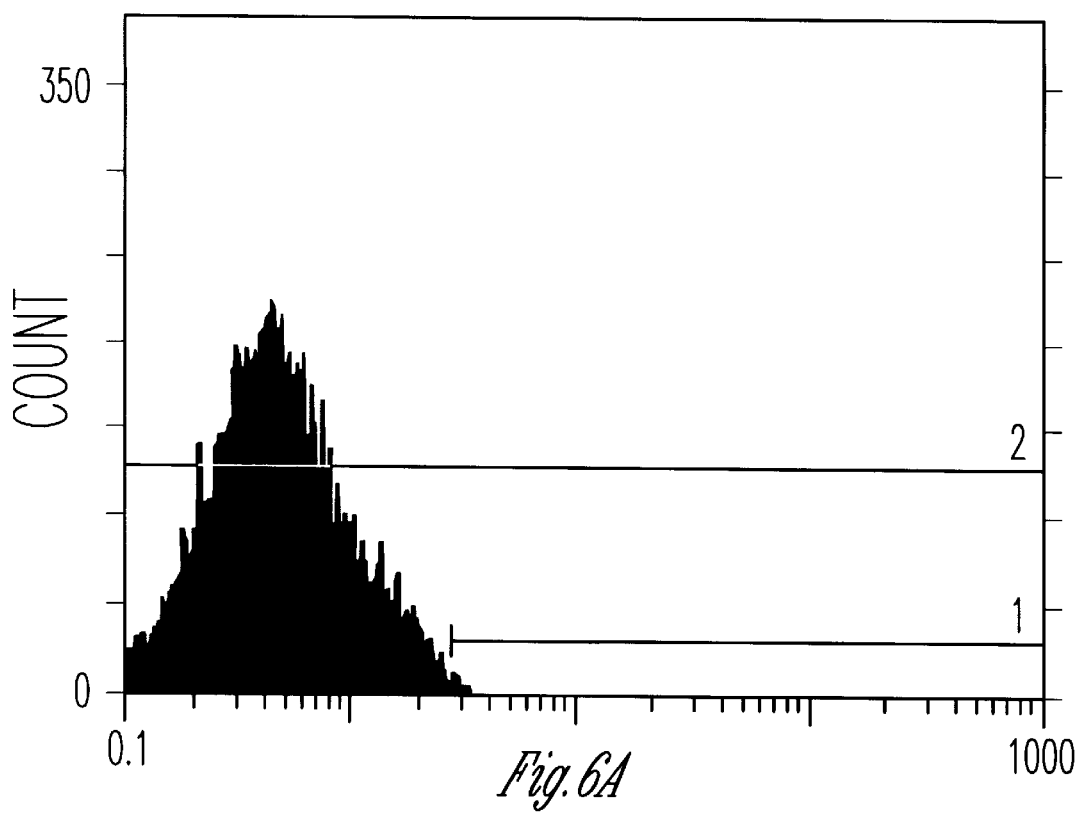
Figure 6B:
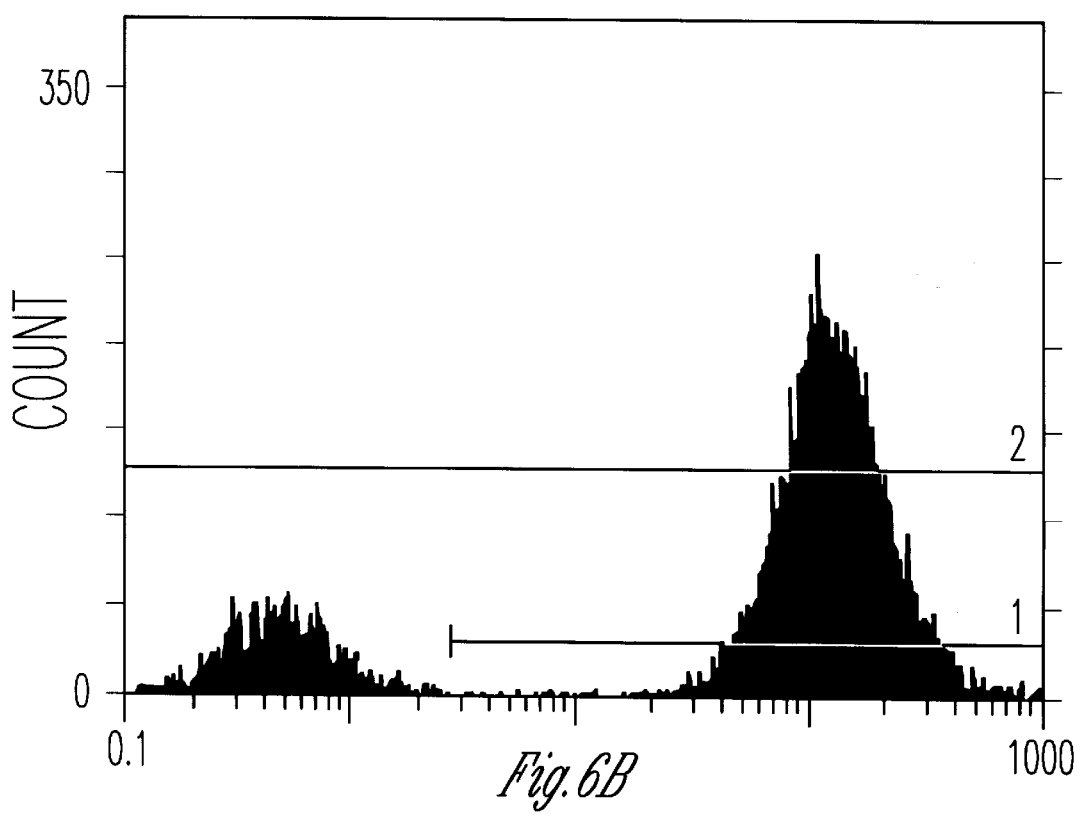
Figure 6C:
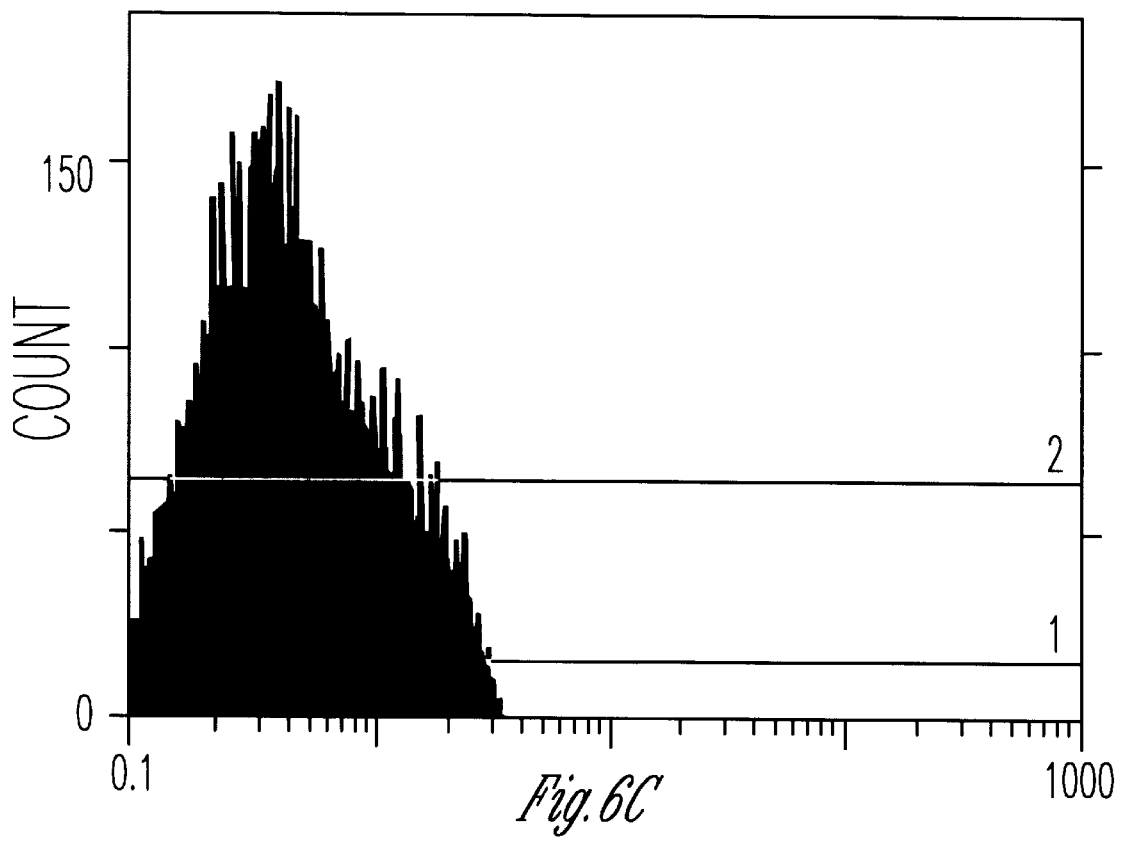
Figure 6D:
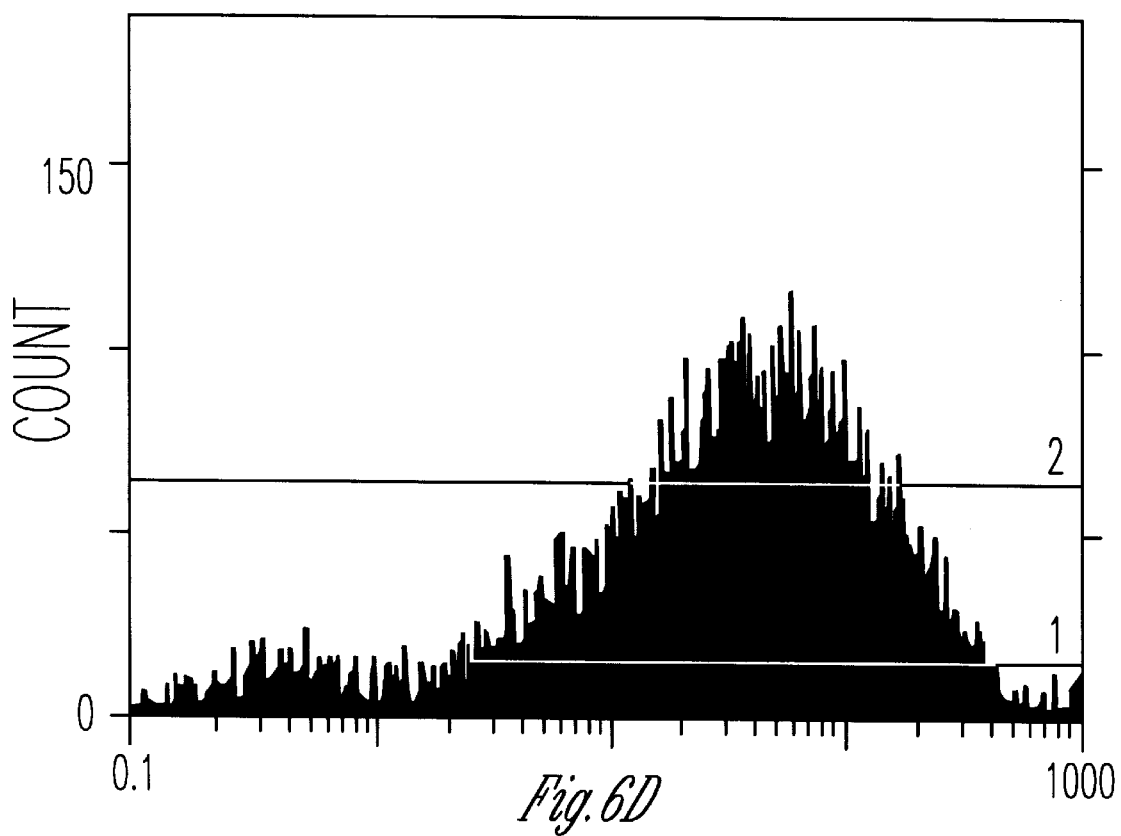

FACS analysis of GFP transfected PA317 vector producer cells and LNChRG transduced A375 melanoma cells. PA317 cells that had been transfected by the LNChRG vector and selected were analyzed by FACS. Excitation with 488 nm light resulted in light emissions at 525 nm in LNChRG containing cells. PA317 cells transfected and expressing hRGFP (FIG. 6B) were easily detected by a two log shift from nontransfected control PA317 cells (FIG. 6A). Using the band pass filter, A375 melanoma cells transduced and selected with the LNChRG vector (FIG. 6D) were readily detected after excitation by a two log shift in detected fluorescence compared to the control nontransduced A375 cells (FIG. 6C).

These results demonstrate the effectiveness of a humanized, red-shifted mutant GFP by retroviral mediated gene transfer into human tumor cells and murine fibroblasts.

TABLE 1

| | Cell Lines Expressing Green Fluorescent Protein | | | |
|---|---|---|---|---|
| Target Cell Line | GFP Gene Transferred | GFP Gene Transfer Method | Fluorescence Intensity# | % Fluorescent Cells@ |
| PA317 fibroblast | GFP | Transient Transfection | + | <2% |
| | GFP | Stable Transfection | 0 | 0 |
| | hRGFP | Transient Transfection | +++++ | 30–40% |
| | hRGFP | Stable Transfection | +++ | >99% |
| A375 | GFP | Transient Transfection | + | <2% |

TABLE 1-continued

Cell Lines Expressing Green Fluorescent Protein

| Target Cell Line | GFP Gene Transferred | GFP Gene Transfer Method | Fluorescence Intensity# | % Fluorescent Cells@ |
|---|---|---|---|---|
| melanoma | GFP | Stable Retroviral Transfection | 0 | 0 |
|  | hRGFP | Transient Transfection | +++ | 30–40% |
|  | hRGFP | Stable Retroviral Transfection | +++ | >99% |

GFP: wild-type GFP gene without red-shift mutation or codon modifications, transfected via pLNCG.
hRGFP: GFP gene modified to convert codon 65-serine to threonine and codon sequences modified to common mammalian usage transfected via pLNChRG.
Relative fluorescence intensity under examination by microscopy
@Percentage of cells exhibiting fluorescence in the transfected population

EXAMPLE 2

Retroviral Transduction GFP into Human Melanoma, Ovarian Carcinoma and Murine Fibroblasts Experimental Protocol Cell culture. A375 is a human melanoma cell line (ATCC, Manassas, Va.). PA317 is a murine amphotropic, retroviral vector packaging cell line (kindly provided by A. D. Miller, University of Washington). GPE86 is a murine ecotropic, retroviral packaging cell line (kindly provided by Arthur Banks). IGROV is an ovarian carcinoma cell line (kindly provided by Patrick Hwu). Cells were grown in RPMI supplemented with 10% fetal calf serum (FCS) (all obtained from Gibco BRL) in monolayers at 370C and 5% $CO_2$. Retroviral vector producer cells (VPC) were grown in RPMI with 10% FCS in monolayers at 37° C and 5% $CO_2$. All cells were passaged and harvested by standard trypsin (Gibco BRL) digestion at 37° C. Cells were routinely passaged at 80–90% confluence.

Plasmid preparation. Plasmid phGFP-S65T was obtained from Clontech (FIG. 7 and Table 2) (Palo Alto, Calif.). The plasmid was kindly provided by Dr. Paul Kitts and Dr. Steve Kain. Cloned construct plasmid DNA was transformed into DH5α competent cells and colonies grown on L-broth supplemented with ampicillin (50 μg/ml) plates (LB/AMP). Positive colonies were grown up in LB/AMP broth and plasmid DNA was isolated using the Qiagen plasmid prep kits (Qiagen Corp., Chatsworth, Calif.).

TABLE 2

SEQUENCE AND RESTRICTION SITE INFORMATION phGFP-S65T Humanized GFP Vector (SEQ ID NO:1) (GenBank Accession # U43284)

Location of features

Human cytomegalovirus (CMV) immediate early
  promoter: 152–739
    Enhancer region: 229–635
    TATA box: 724–730
  T7 promoter: 784–803
  Green fluorescent protein gene (S65T variant)
    Start codon (ATG): 826–828; Stop codon: 1543–1545
    GFP fluorescent chromophore: 1021–1029
  SV40 small t antigen intron: 1642–1706
  SV40 early mRNA polyadenylation signal
    Polyadenylation signals: 2312–2317 & 2341–2346
    mRNA 3' ends: 2350 & 2362
  SV40 origin of replication: 2805–2740
  pBR322 plasmid replication origin: 2767–3347
  M13 single-strand DNA origin: 3367–3934
  Synthetic supF gene: 4145–3947

TABLE 2-continued

Geneology

| From | To | |
|---|---|---|
| 1549 | 811 | pCDM7 vector backbone (Not I-Hind III) |
| 1 | 151 | Fragment from the Rous Sarcoma Virus (RSV) LTR |
| 152 | 738 | Fragment from Human Cytcmegalovirus (CMV) containing the immediate early promoter |
| 812 | 1548 | Synthetic GFP gene using optimal human codons |
| 817 | 829 | Synthetic Kozak consensus translation initiation sequence |
| 829 | 831 | Additional valine not present in wt GFP |
| 1021 | 1023 | S65T mutation in GFP chromophore replacing serine 65 with threonine [Heim, R. et al. (1995) Nature 373:663–664] |
| 1565 | 2174 | Fragment from SV40 providing small antigen intron |
| 2175 | 2415 | Fragment from SV40 providing polyadenylation signals |
| 2416 | 2759 | Fragment from SV40 providing origin of replication |
| 2767 | 3347 | Fragment from pBR322 providing origin of replication |
| 3367 | 3934 | Fragment from M13 providing single-stranded DNA origin |
| 3947 | 4145 | Synthetic supF gene |

Propagation in E. coli

Suitable host strain: MC1061/P3
Selectable Marker: The supF gene confers resistance to ampicillin (25–40 μg/ml) and tetracycline (7.5–10 μg/ml) to MC1061/P3 due to expression of a tRNA that suppresses amber mutations in the ampicillin and tetracycline genes on the P3 plasmid.
E. coli replication origin: pBR322 (rop⁻)
Copy number: = 100–200
Plasmid incompatibility group: pMB1/ColE1

Construction of GFP retroviral vector. Plasmid phGFP-S65T was restriction digested with Hind III and Not I. The 750 bp fragment containing GFP was gel isolated (Jetsorb, Genomed). Plasmid pLNCX was restriction digested with Hind III and Hpa I. The GFP fragment was then ligated into pLNCX followed by a klenow reaction to blunt the 3' end of the GFP. A second ligation was then performed to ligate the 3' end into the Hpa I site to produce plasmid pLNChGS65T. Positive clones drop out a 300, 500, and 600 bp fragment following restriction digest with Ban HI and Nco I.

Transient expression of GFP. PA317 cells were seeded on a sterilized coverslip in a 6 well dish 12–24 hours before transfection. Cells were at 30–50% confluence at the time of DNA transfection. Five μg of DNA and 15 μl of DOTAP reagent (Boehringer Mannheim) was used as per the manufacturer's protocol. The mixture was added to the plates containing RPMI 1640 with 10% FBS, L-glutamine, and penicillin/streptomycin. After 10–18 hours the media was replaced with fresh RPMI media. The coverslip containing the cells was inverted, placed on a slide and examined for fluorescence 9–48 hours after transfection.

Production of the vector producer cell line—PA317-HGS65T VPC. GPE86 cells were seeded in a 6 well dish 24 hours before transfection. Cells were at 30–50% confluence at the time of DNA transfection. Five $\mu$g of DNA and 15 $\mu$l of DOTAP reagent (Boehringer Mannheim) was used per the manufacturer's protocol. The mixture was added to the dishes containing RPMI 1640 with 10% FBS, L-glutamine, and penicillin/streptomycin. After 12 hours the cells were rinsed once and 1 ml of RPMI media was placed in each well. Retroviral supernate was collected 24 hours later, sterile filtered and 10 $\mu$g/ml protamine sulfate solution was added. This supernate was transferred to a 6 well dish containing PA317 cells which were at 30–50% confluence. After an additional 24 hours cells from each well were trypsin digested and transferred to a 10 cm tissue culture dish (Falcon). G418 (1 mg/ml) was added after another 24 hours for 10–14 days.

Transduction of A375 and IGROV cell lines. PA317-HGS65T VPC cells were grown to 80–90% confluency in a T175 flask. The media was then replaced with 20 ml fresh media. 24 hours later the retroviral supernate was collected, filtered (0.45 $\mu$m costar) and supplemented with 10 $\mu$g/ml protamine sulfate. A375 and IGROV cells were seeded in a 10 cm tissue culture dish and in 6 well dishes containing sterile coverslips. 10 ml of supernate was added to the culture dish, and 2 ml was added to each well. 24 hours later the supernate was removed and replaced with G418 (1 mg/ml). Coverslips were removed 72 hours post transduction and later for fluorescent microscopy and photography.

Fluorescent detection of green fluorescent protein expressing cells. The inventors visualized GFP expressed cells with a Nikon Labophot-2 Fluorescent Microscope (Fryer Company, Inc.). The cube used in the microscope was the FITC dichromic filter set (excitation at 450–490 nm and emission at 520 nm) for the hRGFP detection. Photographs were taken using the Nikon Microflex AFX-DX systems (Fryer Company, Inc.).

Fluorescence activated cell sorted analysis of and transduced cells. Cytometry of transduced cells was performed on a Epics Profile II Analyzer. Cells were analyzed using a 525 nm band pas filter set (Part #814036, Coulter Corp.). Cultures of nontransduced PA317, A375, and IGROV cells, as well as transduced PA317, A375, and IGROV cells that were 80–90% confluent were trypsin digested washed with RPMI with 10% FCS and resuspended at a concentration of approx. 1×10$^6$ cells/ml. All FACS analysis used the FL1 emission channel to monitor green fluorescence (normally a FITC monitor).

Results

Transfected cell lines. PA317 retroviral packaging cells were transiently transfected with pLNChGS65T. The construct fluoresces at many different levels. Nontransfected PA317 cells did not demonstrate green fluorescence. Fluorescence can be detected as early as 9 hours post-transfection. By 36 hours, 30–40% or more of the cells are easily visualized, and contain enough protein to produce an intense fluorescence. We did not observe any cytopathic or growth inhibiting effect due to pLNChGsS65T in transfected cells.

Transduced expression of GFP. After selection nearly 100% of PA317-HGS65T VPC were fluorescing with great intensity comparable to that of the transfected cells. A375 and IGROV cells were examined for fluorescence 72 hours post transduction for transduction efficiency. Both cell lines appear to be 50% fluorescent. After only 7 days of selection, A375 cells were at approximately 90% fluorescence. 75% of the total IGROV cells were fluorescent at 4 days post selection.

FACS analysis of GFP transduced cell lines. PA317, A375, and IGROV cells that had been transduced by LNCHGS65T VPC and selected were analyzed by FACS. Emission was detected at 525 nm. PA317-HGS65T were easily distinguished by a two log shift from nontransfected control PA317 cells by FACS analysis. Using the same 525 nm band pass filter, A375 melanoma cells transduced, not selected were readily detected after excitation with 488 nm light by a two log shift in detected fluorescence compared to the control nontransduced A375 cells IGROV cells transduced, not selected were readily detected after excitation with 488 nm light by a two log shift in detected fluorescence compared to the control nontransduced IGROV cells. These results demonstrate that GFP gene fluorescence can be quantified with available instrumentation.

EXAMPLE 3

Tracking and Quantitation of Retroviral-Mediated Transfer Using a Completely Humanized, Red-Shifted Green Fluorescent Protein Gene Cell Culture. The following cell lines were used: A375, a human melanoma cell line (ATCC, Manassas, Va., USA); IGROV, an ovarian carcinoma cell line (kindly provided by Patrick Hwu, National Cancer Institute); PA317, a murine amphotropic, RV-packaging cell line (kindly provided by A.D. Miller, University of Washington); and GPE86, a murine ecotropic, RV-packaging cell line (kindly provided by Arthur Banks, Columbia University). Cells were grown in RPMI supplemented with 10% fetal calf serum (FCS) (both obtained from Life Technologies, Gaithersburg, Md., USA) in monolayers at 37° C. and 5% $CO_2$. All cells were passaged and harvested by standard trypsin (Life Technologies) digestion at 37° C. Cells were routinely passaged at 80%–90% confluence.

Construction of GFP Retroviral Vector. Plasmid phGFP-S65T was obtained from CLONTECH Laboratories (Palo Alto, Calif., USA). Cloned construct plasmid DNA was transformed into MAX Efficiency DH5α™ Competent Cells (Life Technologies), and colonies were grown on L-broth supplemented with ampicillin (50 $\mu$g/mL) plates (LB/AMP). Positive colonies were grown in LB/AMP broth, and plasmid DNA was isolated using the plasmid kit from Qiagen (Chatsworth, Calif., USA). Plasmid phGFP-S65T was restriction-digested with HindIII and NotI to obtain the 750-bp hGFP-S65T open reading fragment, which was then gel-isolated (Jetsorb©; Genomed, Raleigh, N.C., USA). Plasmid pLNCX was restriction-digested with HindIII and HpaI. The hGFP-S65T fragment was then ligated into linearized pLNCX, followed by treatment with a Klenow enzyme to remove the NotI overhang. This 3' end was then ligated to the HpaI site to produce plasmid pLNChG65T.

Construction of the LNChG65T Vector-Producer Cell Line. GPE86 cells were plated in a 6-well dish (Falcon®) 24 hours before transfection. Cells that were at 30%–50% confluence were transfected with 5 $\mu$g of pLNChG65T plasmid DNA and 15 $\mu$L of DOTAP reagent (Boehringer Mannheim, Indianapolis, Ind., USA) according to the manufacturer's protocol. After 12 hours, the cells were rinsed, and 1 mL of fresh medium was placed in each well. RV supernatant was collected 24 hours later and filtered (0.45 $\mu$m; Corning Costar, Cambridge, Mass., USA); then 10 $\mu$g/mL of protamine sulfate solution were added. This supernatant was transferred to a 6-well dish containing PA317 cells that were at 30%–50% confluence. After 24 hours, both cell lines were trypsin-digested and transferred to a 10-cm tissue culture dish (Falcon). Cells were selected in 1 mg/mL G-418 (Genteticin®; Life Technologies for 10–14 days.

Transduction of A375 and IGROV Human Tumor Cell Lines. LNChG65T VPC cells were grown to 80%–90% confluence in Nunclon™ T-175 flasks (Allegiance Health Care, McGaw Park, Ill., USA). The medium was replaced with 30 mL of fresh medium, and 24 hours later the RV supernatant was collected, filtered and supplemented with 10 μg/mL protamine sulfate. A 375 and IGROV cells were plated onto 10-cm tissue culture dishes and in 6-well dishes containing sterile coverslips. Ten milliliters of the supernatant were added to the culture dishes, and 2 mL were added to each well of the 6-well plates. The supernatant was removed 24 hours later and replaced with fresh medium containing G-418 (1 mg/mL) and selected for 7–14 days.

Fluorescent Detection of GFP-Expressing Cells. The hGFP-S65T-expressing cells were visualized with a Nikon Labophot-2™ fluorescent microscope (Melville, N.Y., USA). The filter cube used in the microscope was the FITC dichroic filter set (excitation at 450–490 nm and emission at 520 nm). The coverslips from the 6-cell dishes were inverted and placed on a glass slide for viewing. Photographs were taken using the Microflex™ AFX-DX systems (Nikon).

Fluorescence-Activated Cell Sorter (FACS) Analysis of LNChG65T-Transduced Mammalian Cells. Cytometry of transduced cells was performed on an EPICS® Profile II analyzer (Coulter, Miami, Fla., USA) with an excitation source of 488 nm. Cells were analyzed using a 525-nm bandpass filter set (Part No. 814036; Coulter). Cultures of cells that were 80%–90% confluent were trypsin-digested, washed with RPMI with 10% FCS and resuspended at a concentration of approximately $1 \times 10^6$ cells/mL. All FACS analyses used the FL1 emission channel to monitor green fluorescence (normally at FITC monitor).

Results

Transfected Cell Lines. GPE86 RV-packaging cells were transfected with the construct pLN-ChG65T (FIG. 9). Once selected, nearly 100% of the cells emitted green fluorescence after excitation (data not shown). No cytopathic or growth-inhibiting effects due to the expression of pLNChG65T in transfected cells were observed.

Transduced Expression of GFP. The LNChG65T vector-producer cell line (VPC) exhibited intense fluorescence. A375-LNChG65T-transduced cells, examined 72 hours after transduction, demonstrated fluorescence in approximately 50% of the cells. After 7 days of G-418 selection, approximately 90% of the A375 (data not shown) and 70% of the IGROV cells demonstrated fluorescent activity. By 14 days after selection, both of the transduced cell lines demonstrated nearly 100% fluorescence. No significant background fluorescence was detected in nontransduced cells.

Figure 10A:
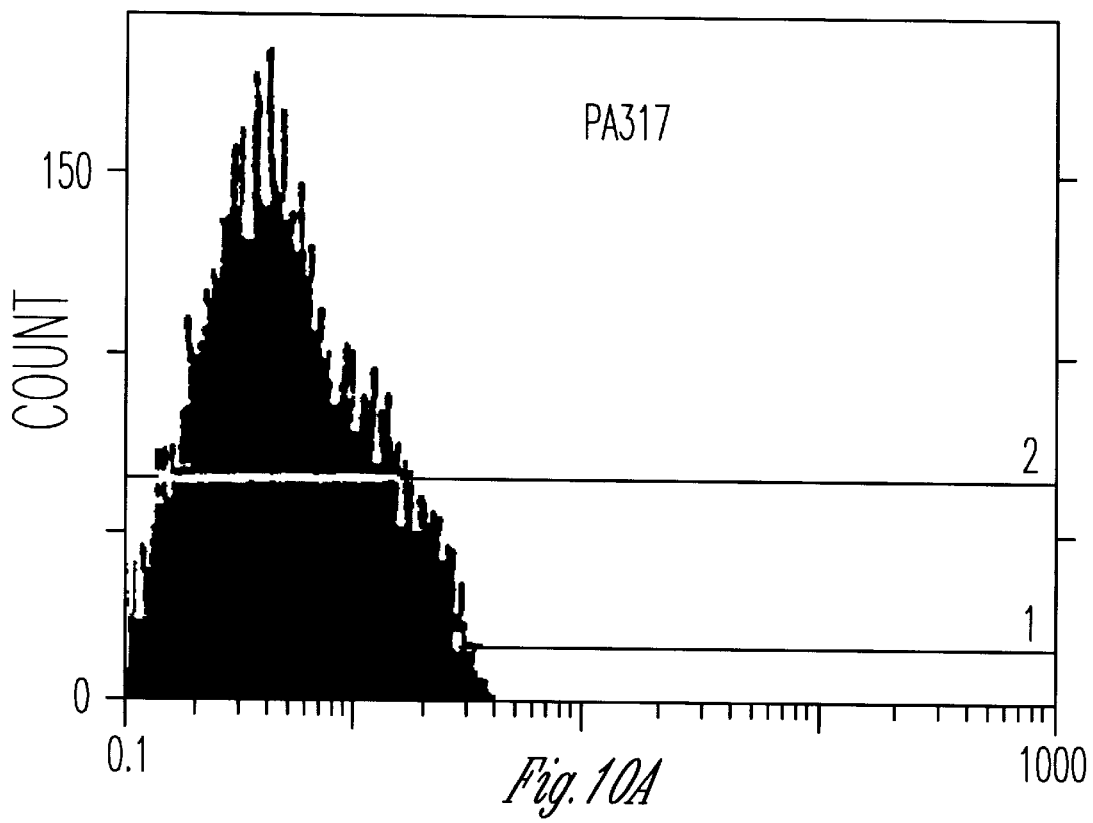
Figure 10B:
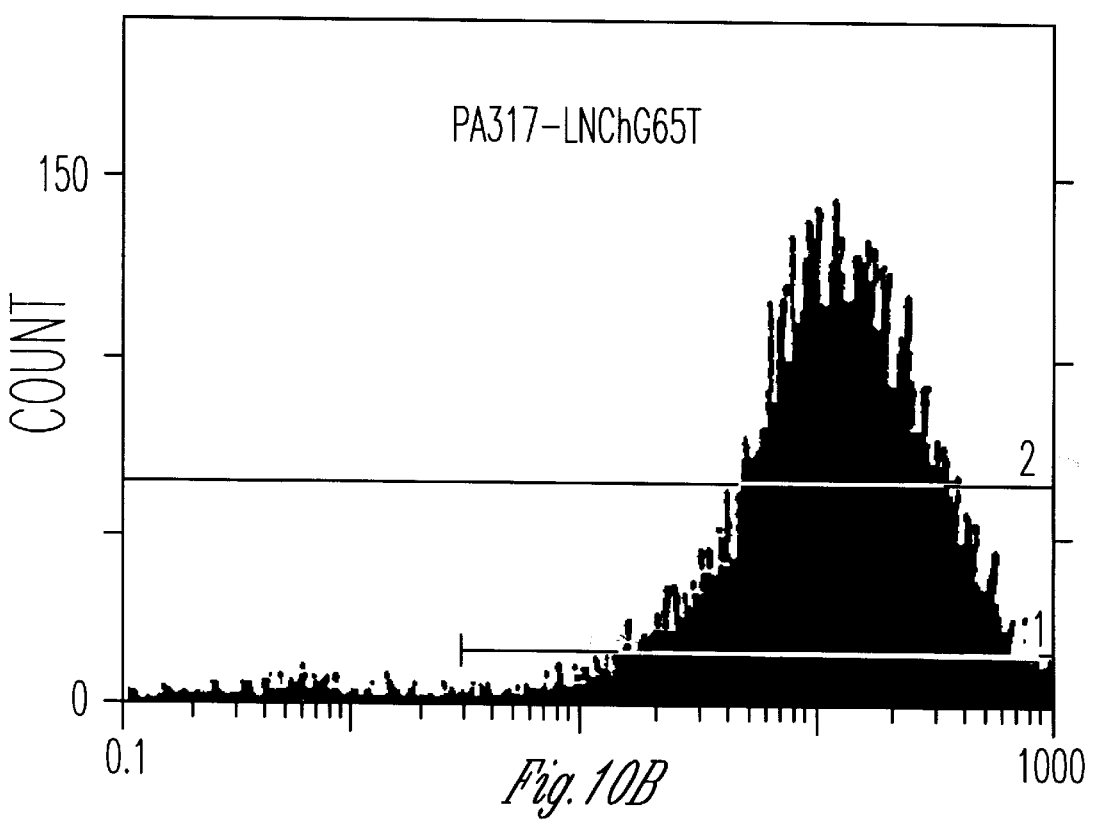
Figure 10C:
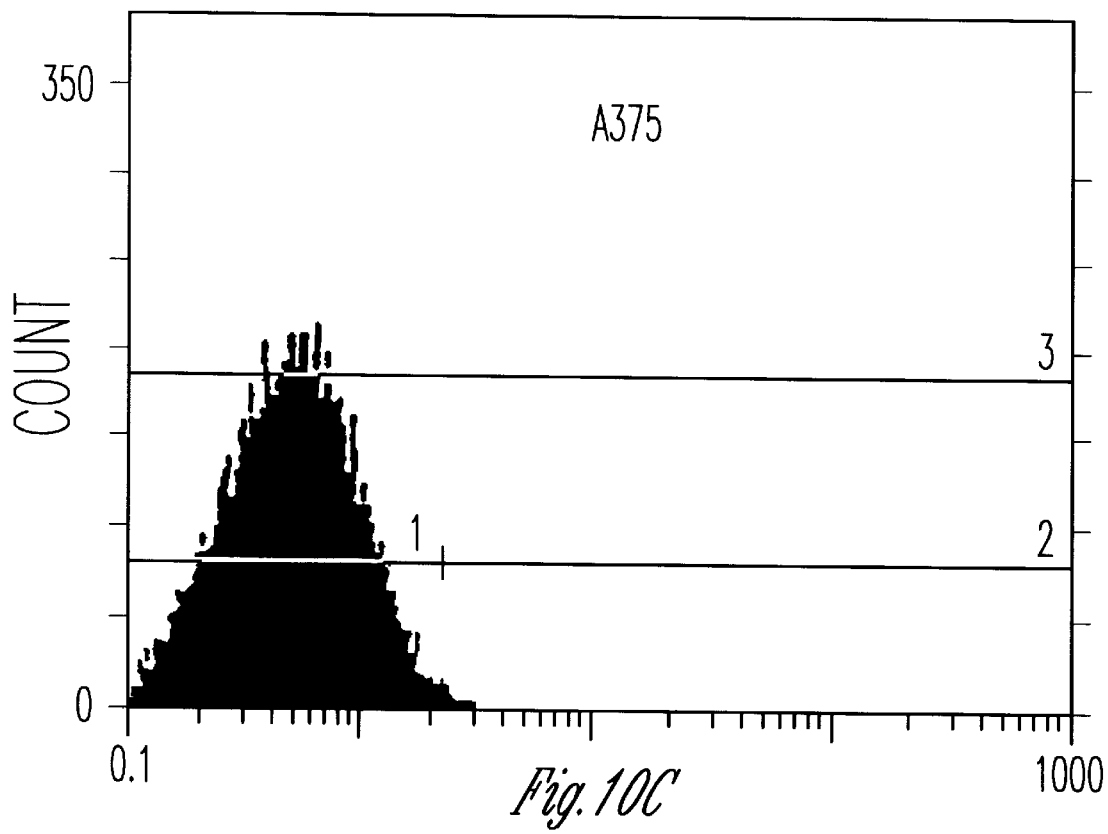
Figure 10D:
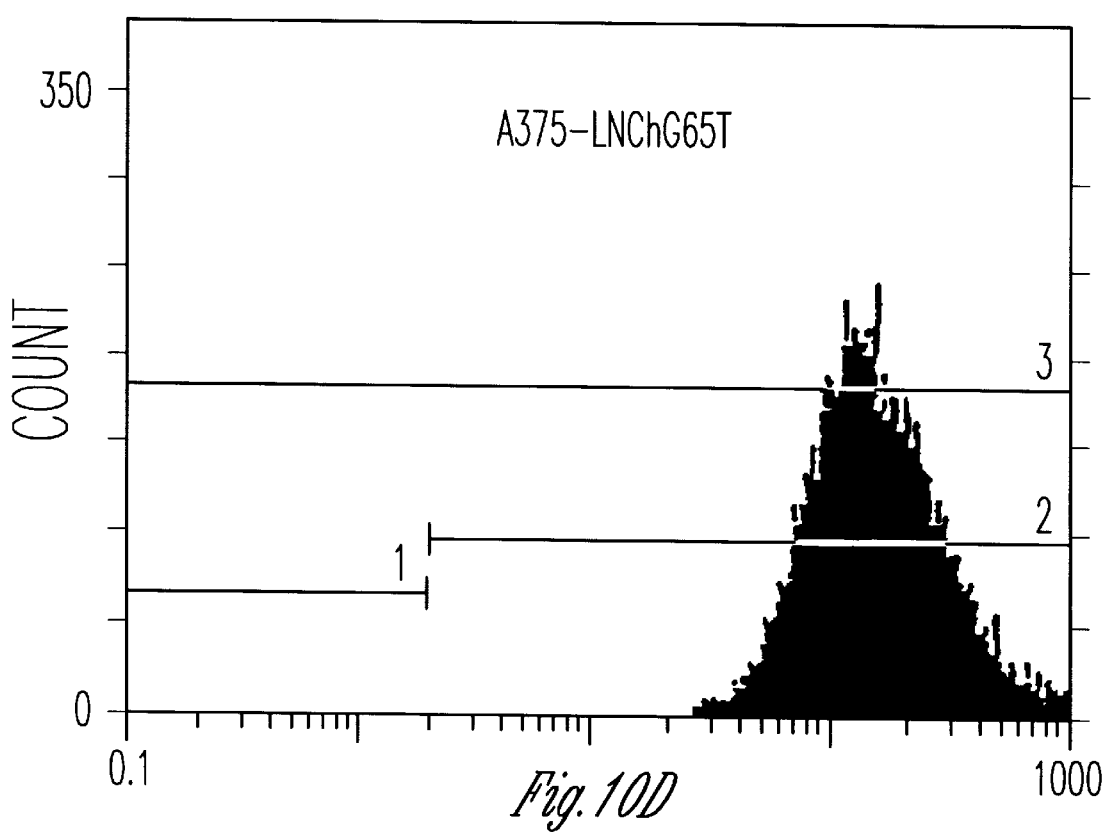
Figure 10E:
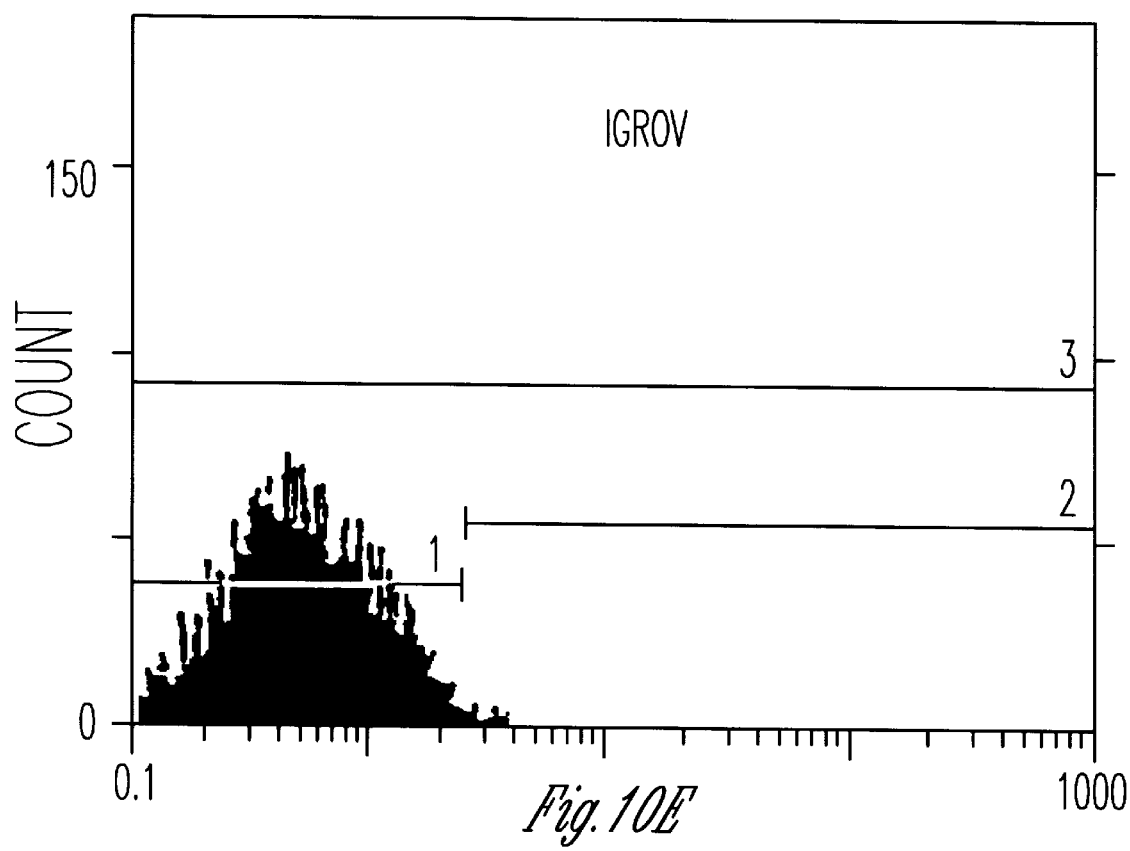
Figure 10F:
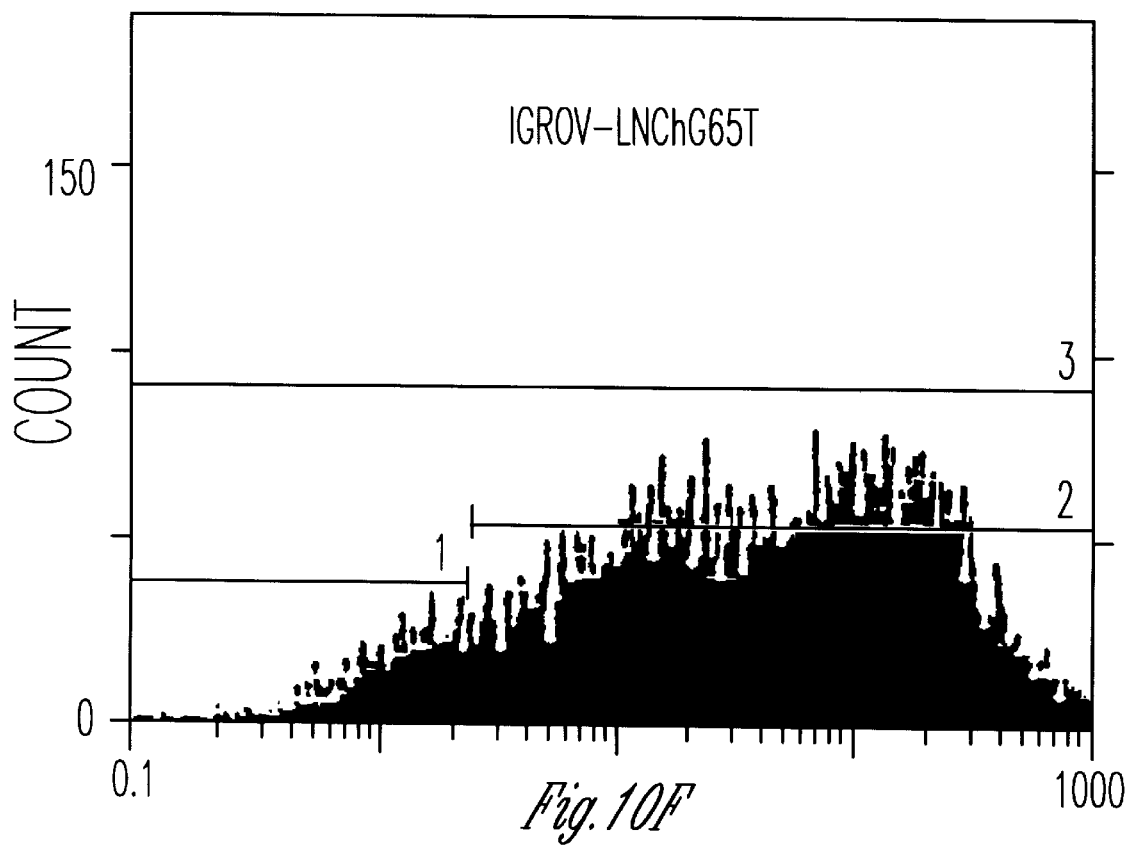

FACS Analysis of GFP-Transduced Cell Lines. PA317, A375 and IGROV cells transduced by the LNChG65T RV vector and selected in G-418 were analyzed by FACS. The PA317- and A375-transduced Cells (FIGS. 10B and D) were distinguished by up to a three log shift in mean fluorescent intensity in comparison to nontransduced control cells (FIGS. 10A and C). Transduced IGROV cells also showed a significant shift in fluorescence intensity.

EXAMPLE 4

Construction of a Vector Producer Cell Line. The hG65T gene was cloned into the retroviral vector pLNCX to produce the pLNChG65T vector (FIG. 9). The vector DNA was transfected with DOTAP into the ecotropic retroviral packaging cell line GP-E86. The supernatant from transfected GP-E86 cells was transferred onto murine amphotropic packaging cell line PA317. 24 hours later, cells were placed under G418 selection for two weeks. The fresh supernatants from LNChG65T vector producer cell line were used to transduce PBL.

PBL Transduction. Human peripheral blood mononuclear cells were isolated from health donors by density gradient centrifugation. Cells were cultured in RPMI 1640 medium, supplemented with 5% human AB serum in the presence of PHA at 1 μg/ml and hIL-2 at 100 U/ml. After 72 hours of incubation, cells were washed and cultured in phosphate-depleted RPMI 1640 medium containing 500 u/ml hIL-2 for 12 hours. PBL were pelleted and resuspended in supernatant from LNChG65T vector producer cells containing 500 U/ml hIL-2 and 10 mg/ml protamine. After 12 hours of incubation at 37° C., 5% $CO_2$, the phosphate-depletion-transduction cycle was repeated twice.

GFP expressing PBL were visualized 24–72 hours after transduction (FIG. 11). Immediately after the completion of transduction procedure PBL population was analyzed for GFP expression and phenotypes using FACS (Epics Profile II Analyzer, standard FITC filter). The population of PBL cultured under the same conditions, but not exposed to viral supernatant served as a control.

The results of FACS analysis show that about 30% of PBL population incubated with LNChG65T viral supernatant expressed GFP (FIG. 12) and the ratio of cells with different phenotypes was not affected by the transduction procedure (35.0% $CD4^+$, 59% $CD8^+$ cells).

Transduced PBL were placed under G418 selection for 7 days and then expanded for 5 days in RPMI 1640 containing 5% human serum and 500 U/ml IL-2.

Figure 13B:
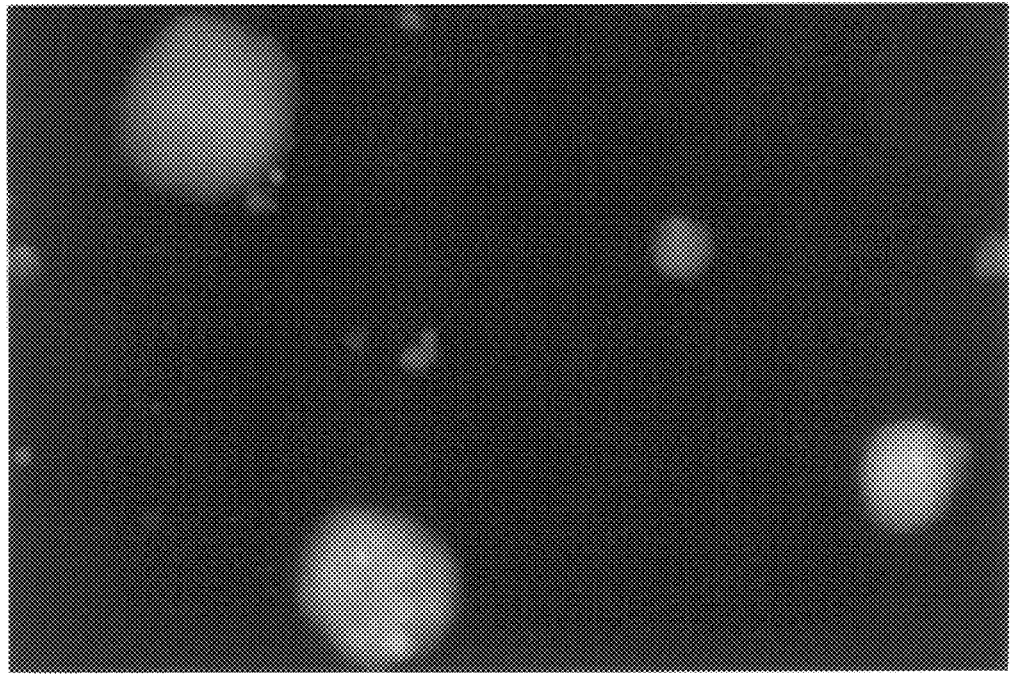

Microphotographs and FACS analysis of G418-selected PBL population are shown in FIGS. 13 and 14. Western analysis demonstrated high levels of GFP protein produced in the transduced cells (FIG. 15)

Alloreactivity of LNChG65T Transduced PBL. The capacity of LNChG65T transduced PBL to respond to an immunological stimulus was tested. The assay used the incorporation of [$^3$H]-thymidine to determine the proliferation rates after stimulation with irradiated LCL/HA lymphoblastoid cells or irradiated, pooled human peripheral blood mononuclear cells (PBMC). Control and transduced PBL cultures were washed twice and incubated in medium without IL-2 for 12 hours prior to stimulation with allogeneic cells. The cell mixtures were cultured in humidified 5% CO2 at 37° C. for 3 days and pulsed with 1 μCi of [$^3$H]-thymidine for the last 18 hours.

Incorporated radioactivity was measured by scintillation counting and was expressed as cpm of radioactivity.

TABLE 3

| Cell Line | +LCL/HA. NV cpm | −LCL/HA. NV cpm | +Pooled PBMC cpm | −Pooled PBMC cpm |
| --- | --- | --- | --- | --- |
| PBL.NV* | 25,840 | 570 | 31,650 | 320 |
| PBL.LNChG65T | 22,670 | 280 | 34,030 | 190 |

*PBL.NV-nontransduced cells

These results demonstrate that transduced peripheral blood lymphocytes remain alloreactive compared to non-transduced control cells.

Conclusion. The results of this study show that the GFP gene can be successfully transferred and stably expressed at high level in human PBL by means of retroviral vector delivery system. GFP expression does not affect the capacity of PBL to respond to an immunological stimulus.

The ability to efficiently sort transduced, living human lymphocytes without prolonged drug selection will allow clinical investigation into a variety of therapeutic gene transfer and marking studies in humans.

What is claimed is:

1. A recombinant DNA construct selected from the group consisting of pLEL (SEQ ID NO: 2), pLESN (SEQ ID NO: 3), pLNCE (SEQ ID NO: 5), pLNChRG (SEQ ID NO: 1), pLTKOCEGFP (SEQ ID NO: 6) and pLNChG65T (SEQ ID NO: 4).

2. An infectious virus comprising retroviral RNA transcribed from a construct according to claim 1 in a host viral packaging cell.

3. A mammalian cell, or cell derived therefrom, comprising at least one copy of a construct according to claim 1.

4. A method for transforming a mammalian cell comprising contacting said cell with the recombinant DNA construct according to claim 1 under conditions promoting infection of a cell by a retrovirus.

5. A method for identifying transformed cells to allow for direct observation of transferred genes into living cells comprising:

introducing to said cell a recombinant DNA construct according to claim 1, and measuring fluorescence of humanized red shifted green fluorescent protein, expressed by said transformed cells.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 7353 base pairs
      (B) TYPE: nucleic acid
      (C) STRANDEDNESS: single
      (D) TOPOLOGY: circular (ii) MOLECULE TYPE: other nucleic acid (iii) HYPOTHETICAL: NO (iv) ANTI-SENSE: NO (xi) SEQUENCE DESCRIPTION: SEQ ID NO:1:

```
GAATTCATAC CAGATCACCG AAAACTGTCC TCCAAATGTG TCCCCCTCAC ACTCCCAAAT    60

TCGCGGGCTT CTGCCTCTTA GACCACTCTA CCCTATTCCC CACACTCACC GGAGCCAAAG   120

CCGCGGCCCT TCCGTTTCTT TGCTTTTGAA AGACCCCACC CGTAGGTGGC AAGCTAGCTT   180

AAGTAACGCC ACTTTGCAAG GCATGGAAAA ATACATAACT GAGAATAGAA AAGTTCAGAT   240

CAAGGTCAGG AACAAAGAAA CAGCTGAATA CCAAACAGGA TATCTGTGGT AAGCGGTTCC   300

TGCCCCGGCT CAGGGCCAAG AACAGATGAG ACAGCTGAGT GATGGGCCAA ACAGGATATC   360

TGTGGTAAGC AGTTCCTGCC CCGGCTCGGG GCCAAGAACA GATGGTCCCC AGATGCGGTC   420

CAGCCCTCAG CAGTTTCTAG TGAATCATCA GATGTTTCCA GGGTGCCCCA AGGACCTGAA   480

AATGACCCTG TACCTTATTT GAACTAACCA ATCAGTTCGC TTCTCGCTTC TGTTCGCGCG   540

CTTCCGCTCT CCGAGCTCAA TAAAAGAGCC CACAACCCCT CACTCGGCGC GCCAGTCTTC   600

CGATAGACTG CGTCGCCCGG GTACCCGTAT TCCCAATAAA GCCTCTTGCT GTTTGCATCC   660

GAATCGTGGT CTCGCTGTTC CTTGGGAGGG TCTCCTCTGA GTGATTGACT ACCCACGACG   720

GGGGTCTTTC ATTTGGGGGC TCGTCCGGGA TTTGGAGACC CCTGCCCAGG GACCACCGAC   780

CCACCACCGG GAGGTAAGCT GGCCAGCAAC TTATCTGTGT CTGTCCGATT GTCTAGTGTC   840

TATGTTTGAT GTTATGCGCC TGCGTCTGTA CTAGTTAGCT AACTAGCTCT GTATCTGGCG   900

GACCCGTGGT GGAACTGACG AGTTCTGAAC ACCCGGCCGC AACCCTGGGA GACGTCCCAG   960

GGACTTTGGG GGCCGTTTTT GTGGCCCGAC CTGAGGAAGG GAGTCGATGT GGAATCCGAC  1020

CCCGTCAGGA TATGTGGTTC TGGTAGGAGA CGAGAACCTA AAACAGTTCC CGCCTCCGTC  1080

TGAATTTTTG CTTTCGGTTT GGAACCGAAG CCGCGCGTCT TGTCTGCTGC AGCGCTGCAG  1140

CATCGTTCTG TGTTGTCTCT GTCTGACTGT GTTTCTGTAT TTGTCTGAAA ATTAGGGCCA  1200

GACTGTTACC ACTCCCTTAA GTTTGACCTT AGGTCACTGG AAAGATGTCG AGCGGATCGC  1260

TCACAACCAG TCGGTAGATG TCAAGAAGAG ACGTTGGGTT ACCTTCTGCT CTGCAGAATG  1320

GCCAACCTTT AACGTCGGAT GGCCGCGAGA CGGCACCTTT AACCGAGACC TCATCACCCA  1380

GGTTAAGATC AAGGTCTTTT CACCTGGCCC GCATGGACAC CCAGACCAGG TCCCCTACAT  1440
```

-continued

```
CGTGACCTGG GAAGCCTTGG CTTTTGACCC CCCTCCCTGG GTCAAGCCCT TTGTACACCC    1500
TAAGCCTCCG CCTCCTCTTC CTCCATCCGC CCCGTCTCTC CCCCTTGAAC CTCCTCGTTC    1560
GACCCCGCCT CGATCCTCCC TTTATCCAGC CCTCACTCCT TCTCTAGGCG CCGGAATTCC    1620
GATCTGATCA AGAGACAGGA TGAGGATCGT TTCGCATGAT TGAACAAGAT GGATTGCACG    1680
CAGGTTCTCC GGCCGCTTGG GTGGAGAGGC TATTCGGCTA TGACTGGGCA ACAGACAA     1740
TCGGCTGCTC TGATGCCGCC GTGTTCCGGC TGTCAGCGCA GGGGCGCCCG GTTCTTTTTG    1800
TCAAGACCGA CCTGTCCGGT GCCCTGAATG AACTGCAGGA CGAGGCAGCG CGGCTATCGT    1860
GGCTGGCCAC GACGGGCGTT CCTTGCGCAG CTGTGCTCGA CGTTGTCACT GAAGCGGGAA    1920
GGGACTGGCT GCTATTGGGC GAAGTGCCGG GCAGGATCT CCTGTCATCT CACCTTGCTC    1980
CTGCCGAGAA AGTATCCATC ATGGCTGATG CAATGCGGCG GCTGCATACG CTTGATCCGG    2040
CTACCTGCCC ATTCGACCAC CAAGCGAAAC ATCGCATCGA GCGAGCACGT ACTCGGATGG    2100
AAGCCGGTCT TGTCGATCAG GATGATCTGG ACGAAGAGCA TCAGGGGCTC GCGCCAGCCG    2160
AACTGTTCGC CAGGCTCAAG GCGCGCATGC CCGACGGCGA GGATCTCGTC GTGACCCATG    2220
GCGATGCCTG CTTGCCGAAT ATCATGGTGG AAAATGGCCG CTTTTCTGGA TTCATCGACT    2280
GTGGCCGGCT GGGTGTGGCG GACCGCTATC AGGACATAGC GTTGGCTACC CGTGATATTG    2340
CTGAAGAGCT TGGCGGCGAA TGGGCTGACC GCTTCCTCGT GCTTTACGGT ATCGCCGCTC    2400
CCGATTCGCA GCGCATCGCC TTCTATCGCC TTCTTGACGA GTTCTTCTGA GCGGGACTCT    2460
GGGGTTCGAA ATGACCGACC AAGCGACGCC CAACCTGCCA TCACGAGATT TCGATTCCAC    2520
CGCCGCCTTC TATGAAAGGT TGGGCTTCGG AATCGTTTTC CGGGACGCCG GCTGGATGAT    2580
CCTCCAGCGC GGGGATCTCA TGCTGGAGTT CTTCGCCCAC CCCGGGCTCG ATCCCCTCGC    2640
GAGTTGGTTC AGCTGCTGCC TGAGGCTGGA CGACCTCGCG GAGTTCTACC GGCAGTGCAA    2700
ATCCGTCGGC ATCCAGGAAA CCAGCAGCGG CTATCCGCGC ATCCATGCCC CCGAACTGCA    2760
GGAGTGGGGA GGCACGATGG CCGCTTTGGT CGAGGCGGAT CCGGCCATTA GCCATATTAT    2820
TCATTGGTTA TATAGCATAA ATCAATATTG CTATTGGCC ATTGCATACG TTGTATCCAT    2880
ATCATAATAT GTACATTTAT ATTGGCTCAT GTCCAACATT ACCGCCATGT TGACATTGAT    2940
TATTGACTAG TTATTAATAG TAATCAATTA CGGGGTCATT AGTTCATAGC CCATATATGG    3000
AGTTCCGCGT TACATAACTT ACGGTAAATG GCCCGCCTGG CTGACCGCCC AACGACCCCC    3060
GCCCATTGAC GTCAATAATG ACGTATGTTC CCATAGTAAC GCCAATAGGG ACTTTCCATT    3120
GACGTCAATG GGTGGAGTAT TTACGGTAAA CTGCCCACTT GGCAGTACAT CAAGTGTATC    3180
ATATGCCAAG TACGCCCCCT ATTGACGTCA ATGACGGTAA ATGGCCCGCC TGGCATTATG    3240
CCCAGTACAT GACCTTATGG GACTTTCCTA CTTGGCAGTA CATCTACGTA TTAGTCATCG    3300
CTATTACCAT GGTGATGCGG TTTTGGCAGT ACATCAATGG GCGTGGATAG CGGTTTGACT    3360
CACGGGGATT TCCAAGTCTC CACCCCATTG ACGTCAATGG GAGTTTGTTT TGGCACCAAA    3420
ATCAACGGGA CTTTCCAAAA TGTCGTAACA ACTCCGCCCC ATTGACGCAA ATGGGCGGTA    3480
GGCATGTACG GTGGGAGGTC TATATAAGCA GAGCTCGTTT AGTGAACCGT CAGATCGCCT    3540
GGAGACGCCA TCCACGCTGT TTTGACCTCC ATAGAAGACA CCGGGACCGA TCCAGCCTCC    3600
GCGGCCCCAA GCTTGCCGCC ACCATGGTGA GCAAGGGCGA GGAGCTCTTC ACCGGGGTGG    3660
TGCCCATCCT GGTCGAGCTG GACGGCGACG TGAACGGCCA CAAGTTCAGC GTGTCCGGCG    3720
AGGGCGACCC CGATGCCACC TACGGCAAGC TGACCCTGAA GTTCATCTGC ACCACCGGCA    3780
AGCTGCCCGT GCCCTGGCCC ACCCTCGTCA CCACCTTCAC CTACGGCGTG CAGTGCTTCA    3840
```

```
GCCGCTACCC CGACCACATG AAGCAGCACG ACTTCTTCAA GTCCGCCATG CCCGAAGGCT    3900

ACGTCCAGGA GCGCACCATC TTCTTCAAGG ACGACGGCAA CTACAAGACC CGCGCCGAGG    3960

TGAAGTTCGA GGGCGACACC CTGGTGAACC GCATCGAGCT GAAGGGCATC GACTTCAAGG    4020

AGGACGGCAA CATCCTGGGG CACAAGCTGG AGTACAACTA CAACAGCCAC AACGTCTATA    4080

TCATGGCCGA CAAGCAGAAG AACGGCATCA AGGTGAACTT CAAGATCCCC CACAACATCG    4140

AGGACGGCAG CGTGCAGCTC GCCGACCACT ACCAGCAGAA CACCCCCATC GGCGACGGCC    4200

CCGTGCTGCT GCCCGACAAC CACTACCTGA GCACCCAGTC CGCCCTGAGC AAAGACCCCA    4260

ACGAGAAGCG CGATCACATG GTCCTGCTGG AGTTCGTGAC CGCCGCCGGG ATCACTCACG    4320

GCATGGACGA GCTGTACAAG TAAAGCGGCC AACATCGATA AAATAAAAGA TTTTATTTAG    4380

TCTCCAGAAA AAGGGGGGAA TGAAAGACCC CACCTGTAGG TTTGGCAAGC TAGCTTAAGT    4440

AACGCCATTT TGCAAGGCAT GGAAAAATAC ATAACTGAGA ATAGAGAAGT TCAGATCAAG    4500

GTCAGGAACA GATGGAACAG CTGAATATGG GCCAAACAGG ATATCTGTGG TAAGCAGTTC    4560

CTGCCCCGGC TCAGGGCCAA GAACAGATGG AACAGCTGAA TATGGGCCAA ACAGGATATC    4620

TGTGGTAAGC AGTTCCTGCC CCGGCTCAGG GCCAAGAACA GATGGTCCCC AGATGCGGTC    4680

CAGCCCTCAG CAGTTTCTAG AGAACCATCA GATGTTTCCA GGGTGCCCCA AGGACCTGAA    4740

ATGACCCTGT GCCTTATTTG AACTAACCAA TCAGTTCGCT TCTCGCTTCT GTTCGCGCGC    4800

TTCTGCTCCC CGAGCTCAAT AAAAGAGCCC ACAACCCCTC ACTCGGGGCG CCAGTCCTCC    4860

GATTGACTGA GTCGCCCGGG TACCCGTGTA TCCAATAAAC CCTCTTGCAG TTGCATCCGA    4920

CTTGTGGTCT CGCTGTTCCT TGGGAGGGTC TCCTCTGAGT GATTGACTAC CCGTCAGCGG    4980

GGGTCTTTCA TTTGGGGGCT CGTCCGGGAT CGGGAGACCC CTGCCCAGGG ACCACCGACC    5040

CACCACCGGG AGGTAAGCTG GCTGCCTCGC GCGTTTCGGT GATGACGGTG AAAACCTCTG    5100

ACACATGCAG CTCCCGGAGA CGGTCACAGC TTGTCTGTAA GCGGATGCCG GGAGCAGACA    5160

AGCCCGTCAG GGCGCGTCAG CGGGTGTTGG CGGGTGTCGG GGCGCAGCCA TGACCCAGTC    5220

ACGTAGCGAT AGCGGAGTGT ATACTGGCTT AACTATGCGG CATCAGAGCA GATTGTACTG    5280

AGAGTGCACC ATATGCGGTG TGAAATACCG CACAGATGCG TAAGGAGAAA ATACCGCATC    5340

AGGCGCTCTT CCGCTTCCTC GCTCACTGAC TCGCTGCGCT CGGTCGTTCG GCTGCGGCGA    5400

GCGGTATCAG CTCACTCAAA GGCGGTAATA CGGTTATCCA CAGAATCAGG GGATAACGCA    5460

GGAAAGAACA TGTGAGCAAA AGGCCAGCAA AAGGCCAGGA ACCGTAAAAA GGCCGCGTTG    5520

CTGGCGTTTT TCCATAGGCT CCGCCCCCCT GACGAGCATC ACAAAAATCG ACGCTCAAGT    5580

CAGAGGTGGC GAAACCCGAC AGGACTATAA AGATACCAGG CGTTTCCCCC TGGAAGCTCC    5640

CTCGTGCGCT CTCCTGTTCC GACCCTGCCG CTTACCGGAT ACCTGTCCGC CTTTCTCCCT    5700

TCGGGAAGCG TGGCGCTTTC TCATAGCTCA CGCTGTAGGT ATCTCAGTTC GGTGTAGGTC    5760

GTTCGCTCCA AGCTGGGCTG TGTGCACGAA CCCCCCGTTC AGCCCGACCG CTGCGCCTTA    5820

TCCGGTAACT ATCGTCTTGA GTCCAACCCG GTAAGACACG ACTTATCGCC ACTGGCAGCA    5880

GCCACTGGTA ACAGGATTAG CAGAGCGAGG TATGTAGGCG GTGCTACAGA GTTCTTGAAG    5940

TGGTGGCCTA ACTACGGCTA CACTAGAAGG ACAGTATTTG GTATCTGCGC TCTGCTGAAG    6000

CCAGTTACCT TCGGAAAAAG AGTTGGTAGC TCTTGATCCG GCAAACAAAC CACCGCTGGT    6060

AGCGGTGGTT TTTTTGTTTG CAAGCAGCAG ATTACGCGCA GAAAAAAAGG ATCTCAAGAA    6120

GATCCTTTGA TCTTTTCTAC GGGGTCTGAC GCTCAGTGGA ACGAAAACTC ACGTTAAGGG    6180
```

| | | |
|---|---|---|
| ATTTTGGTCA TGAGATTATC AAAAAGGATC TTCACCTAGA TCCTTTTAAA TTAAAAATGA | 6240 | |
| AGTTTTAAAT CAATCTAAAG TATATATGAG TAAACTTGGT CTGACAGTTA CCAATGCTTA | 6300 | |
| ATCAGTGAGG CACCTATCTC AGCGATCTGT CTATTTCGTT CATCCATAGT TGCCTGACTC | 6360 | |
| CCCGTCGTGT AGATAACTAC GATACGGGAG GGCTTACCAT CTGGCCCCAG TGCTGCAATG | 6420 | |
| ATACCGCGAG ACCCACGCTC ACCGGCTCCA GATTTATCAG CAATAAACCA GCCAGCCGGA | 6480 | |
| AGGGCCGAGC GCAGAAGTGG TCCTGCAACT TTATCCGCCT CCATCCAGTC TATTAATTGT | 6540 | |
| TGCCGGGAAG CTAGAGTAAG TAGTTCGCCA GTTAATAGTT TGCGCAACGT TGTTGCCATT | 6600 | |
| GCTGCAGGCA TCGTGGTGTC ACGCTCGTCG TTTGGTATGG CTTCATTCAG CTCCGGTTCC | 6660 | |
| CAACGATCAA GGCGAGTTAC ATGATCCCCC ATGTTGTGCA AAAAAGCGGT TAGCTCCTTC | 6720 | |
| GGTCCTCCGA TCGTTGTCAG AAGTAAGTTG GCCGCAGTGT TATCACTCAT GGTTATGGCA | 6780 | |
| GCACTGCATA ATTCTCTTAC TGTCATGCCA TCCGTAAGAT GCTTTTCTGT GACTGGTGAG | 6840 | |
| TACTCAACCA AGTCATTCTG AGAATAGTGT ATGCGGCGAC CGAGTTGCTC TTGCCCGGCG | 6900 | |
| TCAACACGGG ATAATACCGC GCCACATAGC AGAACTTTAA AAGTGCTCAT CATTGGAAAA | 6960 | |
| CGTTCTTCGG GGCGAAAACT CTCAAGGATC TTACCGCTGT TGAGATCCAG TTCGATGTAA | 7020 | |
| CCCACTCGTG CACCCAACTG ATCTTCAGCA TCTTTTACTT TCACCAGCGT TTCTGGGTGA | 7080 | |
| GCAAAAACAG GAAGGCAAAA TGCCGCAAAA AAGGGAATAA GGGCGACACG GAAATGTTGA | 7140 | |
| ATACTCATAC TCTTCCTTTT TCAATATTAT TGAAGCATTT ATCAGGGTTA TTGTCTCATG | 7200 | |
| AGCGGATACA TATTTGAATG TATTTAGAAA AATAAACAAA TAGGGGTTCC GCGCACATTT | 7260 | |
| CCCCGAAAAG TGCCACCTGA CGTCTAAGAA ACCATTATTA TCATGACATT AACCTATAAA | 7320 | |
| AATAGGCGTA TCACGAGGCC CTTTCGTCTT CAA | 7353 | |

(2) INFORMATION FOR SEQ ID NO:2:

(i) SEQUENCE CHARACTERISTICS:
        (A) LENGTH: 5363 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:2:

| | | |
|---|---|---|
| GAATTGCTAG CAATTGCTAG CAATTGCTAG CAATTCATAC CAGATCACCG AAAACTGTCC | 60 | |
| TCCAAATGTG TCCCCCTCAC ACTCCCAAAT TCGCGGGCTT CTGCCTCTTA GACCACTCTA | 120 | |
| CCCTATTCCC CACACTCACC GGAGCCAAAG CCGCGGCCCT TCCGTTTCTT TGCTTTTGAA | 180 | |
| AGACCCCACC CGTAGGTGGC AAGCTAGCTT AAGTAACGCC ACTTTGCAAG GCATGGAAAA | 240 | |
| ATACATAACT GAGAATAGAA AAGTTCAGAT CAAGGTCAGG AACAAAGAAA CAGCTGAATA | 300 | |
| CCAAACAGGA TATCTGTGGT AAGCGGTTCC TGCCCCGGCT CAGGGCCAAG AACAGATGAG | 360 | |
| ACAGCTGAGT GATGGGCCAA ACAGGATATC TGTGGTAAGC AGTTCCTGCC CCGGCTCGGG | 420 | |
| GCCAAGAACA GATGGTCCCC AGATGCGGTC CAGCCCTCAG CAGTTTCTAG TGAATCATCA | 480 | |
| GATGTTTCCA GGGTGCCCCA AGGACCTGAA AATGACCCTG TACCTTATTT GAACTAACCA | 540 | |
| ATCAGTTCGC TTCTCGCTTC TGTTCGCGCG CTTCCGCTCT CCGAGCTCAA TAAAAGAGCC | 600 | |
| CACAACCCCT CACTCGGCGC GCCAGTCTTC CGATAGACTG CGTCGCCCGG GTACCCGTAT | 660 | |

```
TCCCAATAAA GCCTCTTGCT GTTTGCATCC GAATCGTGGT CTCGCTGTTC CTTGGGAGGG      720

TCTCCTCTGA GTGATTGACT ACCCACGACG GGGGTCTTTC ATTTGGGGGC TCGTCCGGGA      780

TTTGGAGACC CCTGCCCAGG GACCACCGAC CCACCACCGG GAGGTAAGCT GGCCAGCAAC      840

TTATCTGTGT CTGTCCGATT GTCTAGTGTC TATGTTTGAT GTTATGCGCC TGCGTCTGTA      900

CTAGTTAGCT AACTAGCTCT GTATCTGGCG GACCCGTGGT GGAACTGACG AGTTCTGAAC      960

ACCCGGCCGC AACCCTGGGA GACGTCCCAG GGACTTTGGG GGCCGTTTTT GTGGCCCGAC     1020

CTGAGGAAGG GAGTCGATGT GGAATCCGAC CCCGTCAGGA TATGTGGTTC TGGTAGGAGA     1080

CGAGAACCTA AAACAGTTCC CGCCTCCGTC TGAATTTTTG CTTTCGGTTT GGAACCGAAG     1140

CCGCGCGTCT TGTCTGCTGC AGCGCTGCAG CATCGTTCTG TGTTGTCTCT GTCTGACTGT     1200

GTTTCTGTAT TTGTCTGAAA ATTAGGGCCA GACTGTTACC ACTCCCTTAA GTTTGACCTT     1260

AGGTCACTGG AAAGATGTCG AGCGGATCGC TCACAACCAG TCGGTAGATG TCAAGAAGAG     1320

ACGTTGGGTT ACCTTCTGCT CTGCAGAATG GCCAACCTTT AACGTCGGAT GGCCGCGAGA     1380

CGGCACCTTT AACCGAGACC TCATCACCCA GGTTAAGATC AAGGTCTTTT CACCTGGCCC     1440

GCATGGACAC CCAGACCAGG TCCCCTACAT CGTGACCTGG GAAGCCTTGG CTTTTGACCC     1500

CCCTCCCTGG GTCAAGCCCT TTGTACACCC TAAGCCTCCG CCTCCTCTTC CTCCATCCGC     1560

CCCGTCTCTC CCCCTTGAAC CTCCTCGTTC GACCCCGCCT CGATCCTCCC TTTATCCAGC     1620

CCTCACTCCT TCTCTAGGCG CCGGAATTCG TTGCTACCGG TCGCCAACAT GGTGAGCAAG     1680

GGCGAGGAGC TGTTCACCGG GGTGGTGCCC ATCCTGGTCG AGCTGGACGG CGACGTGAAC     1740

GGCCACAAGT TCAGCGTGTC CGGCGAGGGC GAGGGCGATG CCACCTACGG CAAGCTGACC     1800

CTGAAGTTCA TCTGCACCAC CGGCAAGCTG CCCGTGCCCT GGCCCACCCT CGTGACCACC     1860

CTGACCTACG GCGTGCAGTG CTTCAGCCGC TACCCCGACC ACATGAAGCA GCACGACGTC     1920

TTCAAGTCCG CCATGCCCGA AGGCTACGTC CAGGAGCGCA CCATCTTCTT CAAGGACGAC     1980

GGCAACTACA AGACCCGCGC CGAGGTGAAG TTCGAGGGCG ACACCCTGGT GAACCGCATC     2040

GAGCTGAAGG GCATCGACTT CAAGGAGGAC GGCAACATCC TGGGGCACAA GCTGGAGTAC     2100

AACTACAACA GCCACAACGT CTATATCATG GCCGACAAGC AGAAGAACGG CATCAAGGTG     2160

AACTTCAAGA TCCGCCACAA CATCGAGGAC GGCAGCGTGC AGCTCGCCGA CCACTACCAG     2220

CAGAACACCC CCATCGGCGA CGGCCCCGTG CTGCTGCCCG ACAACCACTA CCTGAGCACC     2280

CAGTCCGCCC TGAGCAAAGA CCCCAACGAG AAGCGCGATC ACATGGTCCT GCTGGAGTTC     2340

GTGACCGCCG CCGGGATCAC TCACGGCATG GACGAGCTGT ACAAGTAGCG GCCATGCTAA     2400

CTCGAGGATC CGAAAGACCC CACCTGTAGG TTTGGCAAGC TAGCTTAAGT AACGCCATTT     2460

TGCAAGGCAT GGAAAAATAC ATAACTGAGA ATAGAGAAGT TCAGATCAAG GTCAGGAACA     2520

GATGGAACAG CTGAATATGG GCCAAACAGG ATATCTGTGG TAAGCAGTTC CTGCCCCGGC     2580

TCAGGGCCAA GAACAGATGG AACAGCTGAA TATGGGCCAA ACAGGATATC TGTGGTAAGC     2640

AGTTCCTGCC CCGGCTCAGG GCCAAGAACA GATGGTCCCC AGATGCGGTC CAGCCCTCAG     2700

CAGTTTCTAG AGAACCATCA GATGTTTCCA GGGTGCCCCA AGGACCTGAA ATGACCCTGT     2760

GCCTTATTTG AACTAACCAA TCAGTTCGCT TCTCGCTTCT GTTCGCGCGC TTCTGCTCCC     2820

CGAGCTCAAT AAAAGAGCCC ACAACCCCTC ACTCGGGGCG CCAGTCCTCC GATTGACTGA     2880

GTCGCCCGGG TACCCGTGTA TCCAATAAAC CCTCTTGCAG TTGCATCCGA CTTGTGGTCT     2940

CGCTGTTCCT TGGGAGGGTC TCCTCTGAGT GATTGACTAC CCGTCAGCGG GGGTCTTTCA     3000

TTTGGGGGCT CGTCCGGGAT CGGGAGACCC CTGCCCAGGG ACCACCGACC CACCACCGGG     3060
```

```
AGGTAAGCTG GCTGCCTCGC GCGTTTCGGT GATGACGGTG AAAACCTCTG ACACATGCAG    3120

CTCCCGGAGA CGGTCACAGC TTGTCTGTAA GCGGATGCCG GGAGCAGACA AGCCCGTCAG    3180

GGCGCGTCAG CGGGTGTTGG CGGGTGTCGG GGCGCAGCCA TGACCCAGTC ACGTAGCGAT    3240

AGCGGAGTGT ATACTGGCTT AACTATGCGG CATCAGAGCA GATTGTACTG AGAGTGCACC    3300

ATATGCGGTG TGAAATACCG CACAGATGCG TAAGGAGAAA ATACCGCATC AGGCGCTCTT    3360

CCGCTTCCTC GCTCACTGAC TCGCTGCGCT CGGTCGTTCG GCTGCGGCGA GCGGTATCAG    3420

CTCACTCAAA GGCGGTAATA CGGTTATCCA CAGAATCAGG GGATAACGCA GGAAAGAACA    3480

TGTGAGCAAA AGGCCAGCAA AAGGCCAGGA ACCGTAAAAA GGCCGCGTTG CTGGCGTTTT    3540

TCCATAGGCT CCGCCCCCCT GACGAGCATC ACAAAAATCG ACGCTCAAGT CAGAGGTGGC    3600

GAAACCCGAC AGGACTATAA AGATACCAGG CGTTTCCCCC TGGAAGCTCC CTCGTGCGCT    3660

CTCCTGTTCC GACCCTGCCG CTTACCGGAT ACCTGTCCGC CTTTCTCCCT TCGGAAGCG    3720

TGGCGCTTTC TCATAGCTCA CGCTGTAGGT ATCTCAGTTC GGTGTAGGTC GTTCGCTCCA    3780

AGCTGGGCTG TGTGCACGAA CCCCCCGTTC AGCCCGACCG CTGCGCCTTA TCCGGTAACT    3840

ATCGTCTTGA GTCCAACCCG GTAAGACACG ACTTATCGCC ACTGGCAGCA GCCACTGGTA    3900

ACAGGATTAG CAGAGCGAGG TATGTAGGCG GTGCTACAGA GTTCTTGAAG TGGTGGCCTA    3960

ACTACGGCTA CACTAGAAGG ACAGTATTTG GTATCTGCGC TCTGCTGAAG CCAGTTACCT    4020

TCGGAAAAAG AGTTGGTAGC TCTTGATCCG GCAAACAAAC CACCGCTGGT AGCGGTGGTT    4080

TTTTTGTTTG CAAGCAGCAG ATTACGCGCA GAAAAAAGG ATCTCAAGAA GATCCTTTGA    4140

TCTTTTCTAC GGGGTCTGAC GCTCAGTGGA ACGAAAACTC ACGTTAAGGG ATTTTGGTCA    4200

TGAGATTATC AAAAAGGATC TTCACCTAGA TCCTTTTAAA TTAAAAATGA AGTTTTAAAT    4260

CAATCTAAAG TATATATGAG TAAACTTGGT CTGACAGTTA CCAATGCTTA ATCAGTGAGG    4320

CACCTATCTC AGCGATCTGT CTATTTCGTT CATCCATAGT TGCCTGACTC CCCGTCGTGT    4380

AGATAACTAC GATACGGGAG GGCTTACCAT CTGGCCCCAG TGCTGCAATG ATACCGCGAG    4440

ACCCACGCTC ACCGGCTCCA GATTTATCAG CAATAAACCA GCCAGCCGGA AGGGCCGAGC    4500

GCAGAAGTGG TCCTGCAACT TTATCCGCCT CCATCCAGTC TATTAATTGT TGCCGGGAAG    4560

CTAGAGTAAG TAGTTCGCCA GTTAATAGTT TGCGCAACGT TGTTGCCATT GCTGCAGGCA    4620

TCGTGGTGTC ACGCTCGTCG TTTGGTATGG CTTCATTCAG CTCCGGTTCC CAACGATCAA    4680

GGCGAGTTAC ATGATCCCCC ATGTTGTGCA AAAAAGCGGT TAGCTCCTTC GGTCCTCCGA    4740

TCGTTGTCAG AAGTAAGTTG GCCGCAGTGT TATCACTCAT GGTTATGGCA GCACTGCATA    4800

ATTCTCTTAC TGTCATGCCA TCCGTAAGAT GCTTTTCTGT GACTGGTGAG TACTCAACCA    4860

AGTCATTCTG AGAATAGTGT ATGCGGCGAC CGAGTTGCTC TTGCCCGGCG TCAACACGGG    4920

ATAATACCGC GCCACATAGC AGAACTTTAA AAGTGCTCAT CATTGGAAAA CGTTCTTCGG    4980

GGCGAAAACT CTCAAGGATC TTACCGCTGT TGAGATCCAG TTCGATGTAA CCCACTCGTG    5040

CACCCAACTG ATCTTCAGCA TCTTTTACTT TCACCAGCGT TTCTGGGTGA GCAAAAACAG    5100

GAAGGCAAAA TGCCGCAAAA AAGGGAATAA GGGCGACACG GAAATGTTGA ATACTCATAC    5160

TCTTCCTTTT TCAATATTAT TGAAGCATTT ATCAGGGTTA TTGTCTCATG AGCGGATACA    5220

TATTTGAATG TATTTAGAAA AATAAACAAA TAGGGGTTCC GCGCACATTT CCCCGAAAAG    5280

TGCCACCTGA CGTCTAAGAA ACCATTATTA TCATGACATT AACCTATAAA AATAGGCGTA    5340

TCACGAGGCC CTTTCGTCTT CAA                                           5363
```

(2) INFORMATION FOR SEQ ID NO:3:

(i) SEQUENCE CHARACTERISTICS:
        (A) LENGTH: 6620 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

```
GAATTGCTAG CAATTGCTAG CAATTGCTAG CAATTCATAC CAGATCACCG AAAACTGTCC      60

TCCAAATGTG TCCCCCTCAC ACTCCCAAAT TCGCGGGCTT CTGCCTCTTA GACCACTCTA     120

CCCTATTCCC CACACTCACC GGAGCCAAAG CCGCGGCCCT TCCGTTTCTT TGCTTTTGAA     180

AGACCCCACC CGTAGGTGGC AAGCTAGCTT AAGTAACGCC ACTTTGCAAG GCATGGAAAA     240

ATACATAACT GAGAATAGAA AAGTTCAGAT CAAGGTCAGG AACAAAGAAA CAGCTGAATA     300

CCAAACAGGA TATCTGTGGT AAGCGGTTCC TGCCCCGGCT CAGGGCCAAG AACAGATGAG     360

ACAGCTGAGT GATGGGCCAA ACAGGATATC TGTGGTAAGC AGTTCCTGCC CCGGCTCGGG     420

GCCAAGAACA GATGGTCCCC AGATGCGGTC CAGCCCTCAG CAGTTTCTAG TGAATCATCA     480

GATGTTTCCA GGGTGCCCCA AGGACCTGAA AATGACCCTG TACCTTATTT GAACTAACCA     540

ATCAGTTCGC TTCTCGCTTC TGTTCGCGCG CTTCCGCTCT CCGAGCTCAA TAAAAGAGCC     600

CACAACCCCT CACTCGGCGC GCCAGTCTTC CGATAGACTG CGTCGCCCGG GTACCCGTAT     660

TCCCAATAAA GCCTCTTGCT GTTTGCATCC GAATCGTGGT CTCGCTGTTC CTTGGGAGGG     720

TCTCCTCTGA GTGATTGACT ACCCACGACG GGGGTCTTTC ATTTGGGGGC TCGTCCGGGA     780

TTTGGAGACC CCTGCCCAGG GACCACCGAC CCACCACCGG GAGGTAAGCT GGCCAGCAAC     840

TTATCTGTGT CTGTCCGATT GTCTAGTGTC TATGTTTGAT GTTATGCGCC TGCGTCTGTA     900

CTAGTTAGCT AACTAGCTCT GTATCTGGCG GACCCGTGGT GGAACTGACG AGTTCTGAAC     960

ACCCGGCCGC AACCCTGGGA GACGTCCCAG GGACTTTGGG GGCCGTTTTT GTGGCCCGAC    1020

CTGAGGAAGG GAGTCGATGT GGAATCCGAC CCCGTCAGGA TATGTGGTTC TGGTAGGAGA    1080

CGAGAACCTA AAACAGTTCC CGCCTCCGTC TGAATTTTTG CTTTCGGTTT GGAACCGAAG    1140

CCGCGCGTCT TGTCTGCTGC AGCGCTGCAG CATCGTTCTG TGTTGTCTCT GTCTGACTGT    1200

GTTTCTGTAT TTGTCTGAAA ATTAGGGCCA GACTGTTACC ACTCCCTTAA GTTTGACCTT    1260

AGGTCACTGG AAAGATGTCG AGCGGATCGC TCACAACCAG TCGGTAGATG TCAAGAAGAG    1320

ACGTTGGGTT ACCTTCTGCT CTGCAGAATG GCCAACCTTT AACGTCGGAT GGCCGCGAGA    1380

CGGCACCTTT AACCGAGACC TCATCACCCA GGTTAAGATC AAGGTCTTTT CACCTGGCCC    1440

GCATGGACAC CCAGACCAGG TCCCCTACAT CGTGACCTGG GAAGCCTTGG CTTTTGACCC    1500

CCCTCCCTGG GTCAAGCCCT TTGTACACCC TAAGCCTCCG CCTCCTCTTC CTCCATCCGC    1560

CCCGTCTCTC CCCCTTGAAC CTCCTCGTTC GACCCCGCCT CGATCCTCCC TTTATCCAGC    1620

CCTCACTCCT TCTCTAGGCG CCGGAATTCG TTGCTACCGG TCGCCACCAT GGTGAGCAAG    1680

GGCGAGGAGC TGTTCACCGG GGTGGTGCCC ATCCTGGTCG AGCTGGACGG CGACGTGAAC    1740

GGCCACAAGT TCAGCGTGTC CGGCGAGGGC GAGGGCGATG CCACCTACGG CAAGCTGACC    1800

CTGAAGTTCA TCTGCACCAC CGGCAAGCTG CCCGTGCCCT GGCCCACCCT CGTGACCACC    1860
```

```
CTGACCTACG GCGTGCAGTG CTTCAGCCGC TACCCCGACC ACATGAAGCA GCACGACGTC    1920

TTCAAGTCCG CCATGCCCGA AGGCTACGTC CAGGAGCGCA CCATCTTCTT CAAGGACGAC    1980

GGCAACTACA AGACCCGCGC CGAGGTGAAG TTCGAGGGCG ACACCCTGGT GAACCGCATC    2040

GAGCTGAAGG GCATCGACTT CAAGGAGGAC GGCAACATCC TGGGGCACAA GCTGGAGTAC    2100

AACTACAACA GCCACAACGT CTATATCATG GCCGACAAGC AGAAGAACGG CATCAAGGTG    2160

AACTTCAAGA TCCGCCACAA CATCGAGGAC GGCAGCGTGC AGCTCGCCGA CCACTACCAG    2220

CAGAACACCC CCATCGGCGA CGGCCCCGTG CTGCTGCCCG ACAACCACTA CCTGAGCACC    2280

CAGTCCGCCC TGAGCAAAGA CCCCAACGAG AAGCGCGATC ACATGGTCCT GCTGGAGTTC    2340

GTGACCGCCG CCGGGATCAC TCACGGCATG GACGAGCTGT ACAAGTAGCG GCCATGCTAA    2400

CTCGAGGATC CGGCTGTGGA ATGTGTGTCA GTTAGGGTGT GGAAAGTCCC CAGGCTCCCC    2460

AGCAGGCAGA AGTATGCAAA GCATGCATCT CAATTAGTCA GCAACCAGGT GTGGAAAGTC    2520

CCCAGGCTCC CCAGCAGGCA GAAGTATGCA AAGCATGCAT CTCAATTAGT CAGCAACCAT    2580

AGTCCCGCCC CTAACTCCGC CCATCCCGCC CCTAACTCCG CCCAGTTCCG CCCATTCTCC    2640

GCCCCATGGC TGACTAATTT TTTTTATTTA TGCAGAGGCC GAGGCCGCCT CGGCCTCTGA    2700

GCTATTCCAG AAGTAGTGAG GAGGCTTTTT TGGAGGCCTA GGCTTTTGCA AAAAGCTTGG    2760

GCTGCAGGTC GAGGCGGATC TGATCAAGAG ACAGGATGAG GATCGTTTCG CATGATTGAA    2820

CAAGATGGAT TGCACGCAGG TTCTCCGGCC GCTTGGGTGG AGAGGCTATT CGGCTATGAC    2880

TGGGCACAAC AGACAATCGG CTGCTCTGAT GCCGCCGTGT TCCGGCTGTC AGCGCAGGGG    2940

CGCCCGGTTC TTTTTGTCAA GACCGACCTG TCCGGTGCCC TGAATGAACT GCAGGACGAG    3000

GCAGCGCGGC TATCGTGGCT GGCCACGACG GGCGTTCCTT GCGCAGCTGT GCTCGACGTT    3060

GTCACTGAAG CGGGAAGGGA CTGGCTGCTA TTGGGCGAAG TGCCGGGGCA GGATCTCCTG    3120

TCATCTCACC TTGCTCCTGC CGAGAAAGTA TCCATCATGG CTGATGCAAT GCGGCGGCTG    3180

CATACGCTTG ATCCGGCTAC CTGCCCATTC GACCACCAAG CGAAACATCG CATCGAGCGA    3240

GCACGTACTC GGATGAAGC CGGTCTTGTC GATCAGGATG ATCTGGACGA AGAGCATCAG    3300

GGGCTCGCGC CAGCCGAACT GTTCGCCAGG CTCAAGGCGC GCATGCCCGA CGGCGAGGAT    3360

CTCGTCGTGA CCCATGGCGA TGCCTGCTTG CCGAATATCA TGGTGGAAAA TGGCCGCTTT    3420

TCTGGATTCA TCGACTGTGG CCGGCTGGGT GTGGCGGACC GCTATCAGGA CATAGCGTTG    3480

GCTACCCGTG ATATTGCTGA AGAGCTTGGC GGCGAATGGG CTGACCGCTT CCTCGTGCTT    3540

TACGGTATCG CCGCTCCCGA TTCGCAGCGC ATCGCCTTCT ATCGCCTTCT TGACGAGTTC    3600

TTCTGAGCGG GACTCTGGGG TTCGATAAAA TAAAAGATTT TATTTAGTCT CCAGAAAAAG    3660

GGGGGAATGA AAGACCCCAC CTGTAGGTTT GGCAAGCTAG CTTAAGTAAC GCCATTTTGC    3720

AAGGCATGGA AAAATACATA ACTGAGAATA GAGAAGTTCA GATCAAGGTC AGGAACAGAT    3780

GGAACAGCTG AATATGGGCC AAACAGGATA TCTGTGGTAA GCAGTTCCTG CCCCGGCTCA    3840

GGGCCAAGAA CAGATGGAAC AGCTGAATAT GGGCCAAACA GGATATCTGT GGTAAGCAGT    3900

TCCTGCCCCG GCTCAGGGCC AAGAACAGAT GGTCCCCAGA TGCGGTCCAG CCCTCAGCAG    3960

TTTCTAGAGA ACCATCAGAT GTTTCCAGGG TGCCCCAAGG ACCTGAAATG ACCCTGTGCC    4020

TTATTTGAAC TAACCAATCA GTTCGCTTCT CGCTTCTGTT CGCGCGCTTC TGCTCCCCGA    4080

GCTCAATAAA AGAGCCCACA ACCCCTCACT CGGGGCGCCA GTCCTCCGAT TGACTGAGTC    4140

GCCCGGGTAC CCGTGTATCC AATAAACCCT CTTGCAGTTG CATCCGACTT GTGGTCTCGC    4200

TGTTCCTTGG GAGGGTCTCC TCTGAGTGAT TGACTACCCG TCAGCGGGGG TCTTTCATTT    4260
```

```
GGGGGCTCGT CCGGGATCGG GAGACCCCTG CCCAGGGACC ACCGACCCAC CACCGGGAGG    4320

TAAGCTGGCT GCCTCGCGCG TTTCGGTGAT GACGGTGAAA ACCTCTGACA CATGCAGCTC    4380

CCGGAGACGG TCACAGCTTG TCTGTAAGCG GATGCCGGGA GCAGACAAGC CCGTCAGGGC    4440

GCGTCAGCGG GTGTTGGCGG GTGTCGGGGC GCAGCCATGA CCCAGTCACG TAGCGATAGC    4500

GGAGTGTATA CTGGCTTAAC TATGCGGCAT CAGAGCAGAT TGTACTGAGA GTGCACCATA    4560

TGCGGTGTGA AATACCGCAC AGATGCGTAA GGAGAAAATA CCGCATCAGG CGCTCTTCCG    4620

CTTCCTCGCT CACTGACTCG CTGCGCTCGG TCGTTCGGCT GCGGCGAGCG GTATCAGCTC    4680

ACTCAAAGGC GGTAATACGG TTATCCACAG AATCAGGGGA TAACGCAGGA AAGAACATGT    4740

GAGCAAAAGG CCAGCAAAAG GCCAGGAACC GTAAAAAGGC CGCGTTGCTG GCGTTTTTCC    4800

ATAGGCTCCG CCCCCCTGAC GAGCATCACA AAAATCGACG CTCAAGTCAG AGGTGGCGAA    4860

ACCCGACAGG ACTATAAAGA TACCAGGCGT TTCCCCCTGG AAGCTCCCTC GTGCGCTCTC    4920

CTGTTCCGAC CCTGCCGCTT ACCGGATACC TGTCCGCCTT TCTCCCTTCG GGAAGCGTGG    4980

CGCTTTCTCA TAGCTCACGC TGTAGGTATC TCAGTTCGGT GTAGGTCGTT CGCTCCAAGC    5040

TGGGCTGTGT GCACGAACCC CCCGTTCAGC CCGACCGCTG CGCCTTATCC GGTAACTATC    5100

GTCTTGAGTC CAACCCGGTA AGACACGACT TATCGCCACT GGCAGCAGCC ACTGGTAACA    5160

GGATTAGCAG AGCGAGGTAT GTAGGCGGTG CTACAGAGTT CTTGAAGTGG TGGCCTAACT    5220

ACGGCTACAC TAGAAGGACA GTATTTGGTA TCTGCGCTCT GCTGAAGCCA GTTACCTTCG    5280

GAAAAAGAGT TGGTAGCTCT TGATCCGGCA ACAAACCAC CGCTGGTAGC GGTGGTTTTT    5340

TTGTTTGCAA GCAGCAGATT ACGCGCAGAA AAAAAGGATC TCAAGAAGAT CCTTTGATCT    5400

TTTCTACGGG GTCTGACGCT CAGTGGAACG AAAACTCACG TTAAGGGATT TTGGTCATGA    5460

GATTATCAAA AAGGATCTTC ACCTAGATCC TTTTAAATTA AAAATGAAGT TTAAATCAA    5520

TCTAAAGTAT ATATGAGTAA ACTTGGTCTG ACAGTTACCA ATGCTTAATC AGTGAGGCAC    5580

CTATCTCAGC GATCTGTCTA TTTCGTTCAT CCATAGTTGC CTGACTCCCC GTCGTGTAGA    5640

TAACTACGAT ACGGGAGGGC TTACCATCTG GCCCCAGTGC TGCAATGATA CCGCGAGACC    5700

CACGCTCACC GGCTCCAGAT TTATCAGCAA TAAACCAGCC AGCCGGAAGG GCCGAGCGCA    5760

GAAGTGGTCC TGCAACTTTA TCCGCCTCCA TCCAGTCTAT TAATTGTTGC CGGGAAGCTA    5820

GAGTAAGTAG TTCGCCAGTT AATAGTTTGC GCAACGTTGT TGCCATTGCT GCAGGCATCG    5880

TGGTGTCACG CTCGTCGTTT GGTATGGCTT CATTCAGCTC CGGTTCCCAA CGATCAAGGC    5940

GAGTTACATG ATCCCCCATG TTGTGCAAAA AAGCGGTTAG CTCCTTCGGT CCTCCGATCG    6000

TTGTCAGAAG TAAGTTGGCC GCAGTGTTAT CACTCATGGT TATGGCAGCA CTGCATAATT    6060

CTCTTACTGT CATGCCATCC GTAAGATGCT TTTCTGTGAC TGGTGAGTAC TCAACCAAGT    6120

CATTCTGAGA ATAGTGTATG CGGCGACCGA GTTGCTCTTG CCCGGCGTCA ACACGGGATA    6180

ATACCGCGCC ACATAGCAGA ACTTTAAAAG TGCTCATCAT TGGAAAACGT TCTTCGGGGC    6240

GAAAACTCTC AAGGATCTTA CCGCTGTTGA GATCCAGTTC GATGTAACCC ACTCGTGCAC    6300

CCAACTGATC TTCAGCATCT TTTACTTTCA CCAGCGTTTC TGGGTGAGCA AAAACAGGAA    6360

GGCAAAATGC CGCAAAAAAG GGAATAAGGG CGACACGGAA ATGTTGAATA CTCATACTCT    6420

TCCTTTTTCA ATATTATTGA AGCATTTATC AGGGTTATTG TCTCATGAGC GGATACATAT    6480

TTGAATGTAT TTAGAAAAAT AAACAAATAG GGGTTCCGCG CACATTTCCC CGAAAAGTGC    6540

CACCTGACGT CTAAGAAACC ATTATTATCA TGACATTAAC CTATAAAAAT AGGCGTATCA    6600
```

| CGAGGCCCTT TCGTCTTCAA | 6620 |

(2) INFORMATION FOR SEQ ID NO:4:

(i) SEQUENCE CHARACTERISTICS:
        (A) LENGTH: 7352 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:4:

| GAATTCATAC CAGATCACCG AAAACTGTCC TCCAAATGTG TCCCCCTCAC ACTCCCAAAT | 60 |
| TCGCGGGCTT CTGCCTCTTA GACCACTCTA CCCTATTCCC CACACTCACC GGAGCCAAAG | 120 |
| CCGCGGCCCT TCCGTTTCTT TGCTTTTGAA AGACCCCACC CGTAGGTGGC AAGCTAGCTT | 180 |
| AAGTAACGCC ACTTTGCAAG GCATGGAAAA ATACATAACT GAGAATAGAA AAGTTCAGAT | 240 |
| CAAGGTCAGG AACAAAGAAA CAGCTGAATA CCAAACAGGA TATCTGTGGT AAGCGGTTCC | 300 |
| TGCCCCGGCT CAGGGCCAAG AACAGATGAG ACAGCTGAGT GATGGGCCAA ACAGGATATC | 360 |
| TGTGGTAAGC AGTTCCTGCC CCGGCTCGGG GCCAAGAACA GATGGTCCCC AGATGCGGTC | 420 |
| CAGCCCTCAG CAGTTTCTAG TGAATCATCA GATGTTTCCA GGGTGCCCCA AGGACCTGAA | 480 |
| AATGACCCTG TACCTTATTT GAACTAACCA ATCAGTTCGC TTCTCGCTTC TGTTCGCGCG | 540 |
| CTTCCGCTCT CCGAGCTCAA TAAAAGAGCC CACAACCCCT CACTCGGCGC GCCAGTCTTC | 600 |
| CGATAGACTG CGTCGCCCGG GTACCCGTAT TCCCAATAAA GCCTCTTGCT GTTTGCATCC | 660 |
| GAATCGTGGT CTCGCTGTTC CTTGGGAGGG TCTCCTCTGA GTGATTGACT ACCCACGACG | 720 |
| GGGGTCTTTC ATTTGGGGGC TCGTCCGGGA TTTGGAGACC CCTGCCCAGG GACCACCGAC | 780 |
| CCACCACCGG GAGGTAAGCT GGCCAGCAAC TTATCTGTGT CTGTCCGATT GTCTAGTGTC | 840 |
| TATGTTTGAT GTTATGCGCC TGCGTCTGTA CTAGTTAGCT AACTAGCTCT GTATCTGGCG | 900 |
| GACCCGTGGT GGAACTGACG AGTTCTGAAC ACCCGGCCGC AACCCTGGGA GACGTCCCAG | 960 |
| GGACTTTGGG GGCCGTTTTT GTGGCCCGAC CTGAGGAAGG GAGTCGATGT GGAATCCGAC | 1020 |
| CCCGTCAGGA TATGTGGTTC TGGTAGGAGA CGAGAACCTA AAACAGTTCC CGCCTCCGTC | 1080 |
| TGAATTTTTG CTTTCGGTTT GGAACCGAAG CCGCGCGTCT TGTCTGCTGC AGCGCTGCAG | 1140 |
| CATCGTTCTG TGTTGTCTCT GTCTGACTGT GTTTCTGTAT TTGTCTGAAA ATTAGGGCCA | 1200 |
| GACTGTTACC ACTCCCTTAA GTTTGACCTT AGGTCACTGG AAAGATGTCG AGCGGATCGC | 1260 |
| TCACAACCAG TCGGTAGATG TCAAGAAGAG ACGTTGGGTT ACCTTCTGCT CTGCAGAATG | 1320 |
| GCCAACCTTT AACGTCGGAT GGCCGCGAGA CGGCACCTTT AACCGAGACC TCATCACCCA | 1380 |
| GGTTAAGATC AAGGTCTTTT CACCTGGCCC GCATGGACAC CCAGACCAGG TCCCCTACAT | 1440 |
| CGTGACCTGG GAAGCCTTGG CTTTTGACCC CCCTCCCTGG GTCAAGCCCT TTGTACACCC | 1500 |
| TAAGCCTCCG CCTCCTCTTC CTCCATCCGC CCCGTCTCTC CCCCTTGAAC CTCCTCGTTC | 1560 |
| GACCCCGCCT CGATCCTCCC TTTATCCAGC CCTCACTCCT TCTCTAGGCG CCGGAATTCC | 1620 |
| GATCTGATCA AGAGACAGGA TGAGGATCGT TTCGCATGAT TGAACAAGAT GGATTGCACG | 1680 |
| CAGGTTCTCC GGCCGCTTGG GTGGAGAGGC TATTCGGCTA TGACTGGGCA ACAGACAA | 1740 |
| TCGGCTGCTC TGATGCCGCC GTGTTCCGGC TGTCAGCGCA GGGGCGCCCG GTTCTTTTTG | 1800 |

-continued

```
TCAAGACCGA CCTGTCCGGT GCCCTGAATG AACTGCAGGA CGAGGCAGCG CGGCTATCGT      1860
GGCTGGCCAC GACGGGCGTT CCTTGCGCAG CTGTGCTCGA CGTTGTCACT GAAGCGGGAA      1920
GGGACTGGCT GCTATTGGGC GAAGTGCCGG GGCAGGATCT CCTGTCATCT CACCTTGCTC      1980
CTGCCGAGAA AGTATCCATC ATGGCTGATG CAATGCGGCG GCTGCATACG CTTGATCCGG      2040
CTACCTGCCC ATTCGACCAC CAAGCGAAAC ATCGCATCGA GCGAGCACGT ACTCGGATGG      2100
AAGCCGGTCT TGTCGATCAG GATGATCTGG ACGAAGAGCA TCAGGGGCTC GCGCCAGCCG      2160
AACTGTTCGC CAGGCTCAAG GCGCGCATGC CCGACGGCGA GGATCTCGTC GTGACCCATG      2220
GCGATGCCTG CTTGCCGAAT ATCATGGTGG AAAATGGCCG CTTTTCTGGA TTCATCGACT      2280
GTGGCCGGCT GGGTGTGGCG GACCGCTATC AGGACATAGC GTTGGCTACC CGTGATATTG      2340
CTGAAGAGCT TGGCGGCGAA TGGGCTGACC GCTTCCTCGT GCTTTACGGT ATCGCCGCTC      2400
CCGATTCGCA GCGCATCGCC TTCTATCGCC TTCTTGACGA GTTCTTCTGA GCGGGACTCT      2460
GGGGTTCGAA ATGACCGACC AAGCGACGCC CAACCTGCCA TCACGAGATT TCGATTCCAC      2520
CGCCGCCTTC TATGAAAGGT TGGGCTTCGG AATCGTTTTC CGGGACGCCG GCTGGATGAT      2580
CCTCCAGCGC GGGGATCTCA TGCTGGAGTT CTTCGCCCAC CCCGGGCTCG ATCCCCTCGC      2640
GAGTTGGTTC AGCTGCTGCC TGAGGCTGGA CGACCTCGCG GAGTTCTACC GGCAGTGCAA      2700
ATCCGTCGGC ATCCAGGAAA CCAGCAGCGG CTATCCGCGC ATCCATGCCC CGAACTGCA      2760
GGAGTGGGGA GGCACGATGG CCGCTTTGGT CGAGGCGGAT CCGGCCATTA GCCATATTAT      2820
TCATTGGTTA TATAGCATAA ATCAATATTG GCTATTGGCC ATTGCATACG TTGTATCCAT      2880
ATCATAATAT GTACATTTAT ATTGGCTCAT GTCCAACATT ACCGCCATGT TGACATTGAT      2940
TATTGACTAG TTATTAATAG TAATCAATTA CGGGGTCATT AGTTCATAGC CCATATATGG      3000
AGTTCCGCGT TACATAACTT ACGGTAAATG GCCCGCCTGG CTGACCGCCC AACGACCCCC      3060
GCCCATTGAC GTCAATAATG ACGTATGTTC CCATAGTAAC GCCAATAGGG ACTTTCCATT      3120
GACGTCAATG GGTGGAGTAT TTACGGTAAA CTGCCCACTT GGCAGTACAT CAAGTGTATC      3180
ATATGCCAAG TACGCCCCCT ATTGACGTCA ATGACGGTAA ATGGCCCGCC TGGCATTATG      3240
CCCAGTACAT GACCTTATGG GACTTTCCTA CTTGGCAGTA CATCTACGTA TTAGTCATCG      3300
CTATTACCAT GGTGATGCGG TTTTGGCAGT ACATCAATGG GCGTGGATAG CGGTTTGACT      3360
CACGGGGATT TCCAAGTCTC CACCCCATTG ACGTCAATGG GAGTTTGTTT TGGCACCAAA      3420
ATCAACGGGA CTTTCCAAAA TGTCGTAACA ACTCCGCCCC ATTGACGCAA ATGGGCGGTA      3480
GGCATGTACG GTGGGAGGTC TATATAAGCA GAGCTCGTTT AGTGAACCGT CAGATCGCCT      3540
GGAGACGCCA TCCACGCTGT TTTGACCTCC ATAGAAGACA CCGGGACCGA TCCAGCCTCC      3600
GCGGCCCCAA GCTTGTTGGC CGCCGCCACC ATGAGCAAGG GCGAGGAACT GTTCACTGGC      3660
GTGGTCCCAA TTCTCGTGGA ACTGGATGGC GATGTGAATG GCACAAATT TTCTGTCAGT      3720
GGAGAGGGTG AAGGTGATGC AACATACGGA AAGCTCACCC TGAAATTCAT CTGCACCACT      3780
GGAAAGCTCC CTGTGCCATG GCCAACACTG GTCACTACCT TCACCTATGG CGTGCAGTGC      3840
TTTTCCAGAT ACCCAGACCA TATGAAGCAG CATGACTTTT TCAAGAGTGC CATGCCCGAG      3900
GGCTATGTGC AGGAGAGAAC CATCTTTTTC AAAGATGACG GAACTACAA GACCCGCGCT      3960
GAAGTCAAGT TCGAAGGTGA CACCCTGGTG AATAGAATCG AGTTGAAGGG CATTGACTTT      4020
AAGGAAGATG GAAACATTCT CGGCCACAAG CTGGAATACA ACTATAACTC CCACAATGTG      4080
TACATCATGG CCGACAAGCA AAAGAATGGC ATCAAGGTCA ACTTCAAGAT CAGACACAAC      4140
ATTGAGGATG GATCCGTGCA GCTGGCCGAC CATTATCAAC AGAACACTCC AATCGGCGAC      4200
```

```
GGCCCTGTGC TCCTCCCAGA CAACCATTAC CTGTCCACCC AGTCTGCCCT GTCTAAAGAT    4260

CCCAACGAAA AGAGAGACCA CATGGTCCTG CTGGAGTTTG TGACCGCTGC TGGGATCACA    4320

CATGGCATGG ACGAGCTGTA CAAGTGAGCA ACATCGATAA AATAAAAGAT TTTATTTAGT    4380

CTCCAGAAAA AGGGGGGAAT GAAAGACCCC ACCTGTAGGT TTGGCAAGCT AGCTTAAGTA    4440

ACGCCATTTT GCAAGGCATG GAAAATACA TAACTGAGAA TAGAGAAGTT CAGATCAAGG     4500

TCAGGAACAG ATGGAACAGC TGAATATGGG CCAAACAGGA TATCTGTGGT AAGCAGTTCC    4560

TGCCCCGGCT CAGGGCCAAG AACAGATGGA ACAGCTGAAT ATGGGCCAAA CAGGATATCT    4620

GTGGTAAGCA GTTCCTGCCC CGGCTCAGGG CCAAGAACAG ATGGTCCCCA GATGCGGTCC    4680

AGCCCTCAGC AGTTTCTAGA GAACCATCAG ATGTTTCCAG GGTGCCCCAA GGACCTGAAA    4740

TGACCCTGTG CCTTATTTGA ACTAACCAAT CAGTTCGCTT CTCGCTTCTG TTCGCGCGCT    4800

TCTGCTCCCC GAGCTCAATA AAAGAGCCCA CAACCCCTCA CTCGGGGCGC CAGTCCTCCG    4860

ATTGACTGAG TCGCCCGGGT ACCCGTGTAT CCAATAAACC CTCTTGCAGT TGCATCCGAC    4920

TTGTGGTCTC GCTGTTCCTT GGGAGGGTCT CCTCTGAGTG ATTGACTACC CGTCAGCGGG    4980

GGTCTTTCAT TTGGGGGCTC GTCCGGGATC GGGAGACCCC TGCCCAGGGA CCACCGACCC    5040

ACCACCGGGA GGTAAGCTGG CTGCCTCGCG CGTTTCGGTG ATGACGGTGA AAACCTCTGA    5100

CACATGCAGC TCCCGGAGAC GGTCACAGCT TGTCTGTAAG CGGATGCCGG GAGCAGACAA    5160

GCCCGTCAGG GCGCGTCAGC GGGTGTTGGC GGGTGTCGGG GCGCAGCCAT GACCCAGTCA    5220

CGTAGCGATA GCGGAGTGTA TACTGGCTTA ACTATGCGGC ATCAGAGCAG ATTGTACTGA    5280

GAGTGCACCA TATGCGGTGT GAAATACCGC ACAGATGCGT AAGGAGAAAA TACCGCATCA    5340

GGCGCTCTTC CGCTTCCTCG CTCACTGACT CGCTGCGCTC GGTCGTTCGG CTGCGGCGAG    5400

CGGTATCAGC TCACTCAAAG GCGGTAATAC GGTTATCCAC AGAATCAGGG GATAACGCAG    5460

GAAAGAACAT GTGAGCAAAA GGCCAGCAAA AGGCCAGGAA CCGTAAAAAG GCCGCGTTGC    5520

TGGCGTTTTT CCATAGGCTC CGCCCCCCTG ACGAGCATCA CAAAAATCGA CGCTCAAGTC    5580

AGAGGTGGCG AAACCCGACA GGACTATAAA GATACCAGGC GTTTCCCCCT GGAAGCTCCC    5640

TCGTGCGCTC TCCTGTTCCG ACCCTGCCGC TTACCGGATA CCTGTCCGCC TTTCTCCCTT    5700

CGGGAAGCGT GGCGCTTTCT CATAGCTCAC GCTGTAGGTA TCTCAGTTCG GTGTAGGTCG    5760

TTCGCTCCAA GCTGGGCTGT GTGCACGAAC CCCCCGTTCA GCCCGACCGC TGCGCCTTAT    5820

CCGGTAACTA TCGTCTTGAG TCCAACCCGG TAAGACACGA CTTATCGCCA CTGGCAGCAG    5880

CCACTGGTAA CAGGATTAGC AGAGCGAGGT ATGTAGGCGG TGCTACAGAG TTCTTGAAGT    5940

GGTGGCCTAA CTACGGCTAC ACTAGAAGGA CAGTATTTGG TATCTGCGCT CTGCTGAAGC    6000

CAGTTACCTT CGGAAAAAGA GTTGGTAGCT CTTGATCCGG CAAACAAACC ACCGCTGGTA    6060

GCGGTGGTTT TTTTGTTTGC AAGCAGCAGA TTACGCGCAG AAAAAAAGGA TCTCAAGAAG    6120

ATCCTTTGAT CTTTTCTACG GGGTCTGACG CTCAGTGGAA CGAAAACTCA CGTTAAGGGA    6180

TTTTGGTCAT GAGATTATCA AAAAGGATCT TCACCTAGAT CCTTTTAAAT TAAAAATGAA    6240

GTTTTAAATC AATCTAAAGT ATATATGAGT AAACTTGGTC TGACAGTTAC CAATGCTTAA    6300

TCAGTGAGGC ACCTATCTCA GCGATCTGTC TATTTCGTTC ATCCATAGTT GCCTGACTCC    6360

CCGTCGTGTA GATAACTACG ATACGGGAGG GCTTACCATC TGGCCCCAGT GCTGCAATGA    6420

TACCGCGAGA CCCACGCTCA CCGGCTCCAG ATTTATCAGC AATAAACCAG CCAGCCGGAA    6480

GGGCCGAGCG CAGAAGTGGT CCTGCAACTT TATCCGCCTC CATCCAGTCT ATTAATTGTT    6540
```

-continued

```
GCCGGGAAGC TAGAGTAAGT AGTTCGCCAG TTAATAGTTT GCGCAACGTT GTTGCCATTG    6600

CTGCAGGCAT CGTGGTGTCA CGCTCGTCGT TTGGTATGGC TTCATTCAGC TCCGGTTCCC    6660

AACGATCAAG GCGAGTTACA TGATCCCCCA TGTTGTGCAA AAAAGCGGTT AGCTCCTTCG    6720

GTCCTCCGAT CGTTGTCAGA AGTAAGTTGG CCGCAGTGTT ATCACTCATG GTTATGGCAG    6780

CACTGCATAA TTCTCTTACT GTCATGCCAT CCGTAAGATG CTTTTCTGTG ACTGGTGAGT    6840

ACTCAACCAA GTCATTCTGA GAATAGTGTA TGCGGCGACC GAGTTGCTCT TGCCCGGCGT    6900

CAACACGGGA TAATACCGCG CCACATAGCA GAACTTTAAA AGTGCTCATC ATTGGAAAAC    6960

GTTCTTCGGG GCGAAAACTC TCAAGGATCT TACCGCTGTT GAGATCCAGT TCGATGTAAC    7020

CCACTCGTGC ACCCAACTGA TCTTCAGCAT CTTTTACTTT CACCAGCGTT TCTGGGTGAG    7080

CAAAAACAGG AAGGCAAAAT GCCGCAAAAA AGGGAATAAG GGCGACACGG AAATGTTGAA    7140

TACTCATACT CTTCCTTTTT CAATATTATT GAAGCATTTA TCAGGGTTAT TGTCTCATGA    7200

GCGGATACAT ATTTGAATGT ATTTAGAAAA ATAAACAAAT AGGGGTTCCG CGCACATTTC    7260

CCCGAAAAGT GCCACCTGAC GTCTAAGAAA CCATTATTAT CATGACATTA ACCTATAAAA    7320

ATAGGCGTAT CACGAGGCCC TTTCGTCTTC AA                                  7352
```

(2) INFORMATION FOR SEQ ID NO:5:

(i) SEQUENCE CHARACTERISTICS:
        (A) LENGTH: 7160 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:5:

```
GAATTCATAC CAGATCACCG AAAACTGTCC TCCAAATGTG TCCCCCTCAC ACTCCCAAAT      60

TCGCGGGCTT CTGCCTCTTA GACCACTCTA CCCTATTCCC CACACTCACC GGAGCCAAAG     120

CCGCGGCCCT TCCGTTTCTT TGCTTTTGAA AGACCCCACC CGTAGGTGGC AAGCTAGCTT     180

AAGTAACGCC ACTTTGCAAG GCATGGAAAA ATACATAACT GAGAATAGAA AAGTTCAGAT     240

CAAGGTCAGG AACAAAGAAA CAGCTGAATA CCAAACAGGA TATCTGTGGT AAGCGGTTCC     300

TGCCCCGGCT CAGGGCCAAG AACAGATGAG ACAGCTGAGT GATGGGCCAA ACAGGATATC     360

TGTGGTAAGC AGTTCCTGCC CCGGCTCGGG GCCAAGAACA GATGGTCCCC AGATGCGGTC     420

CAGCCCTCAG CAGTTTCTAG TGAATCATCA GATGTTTCCA GGGTGCCCCA AGGACCTGAA     480

AATGACCCTG TACCTTATTT GAACTAACCA ATCAGTTCGC TTCTCGCTTC TGTTCGCGCG     540

CTTCCGCTCT CCGAGCTCAA TAAAAGAGCC CACAACCCCT CACTCGGCGC GCCAGTCTTC     600

CGATAGACTG CGTCGCCCGG GTACCCGTAT TCCCAATAAA GCCTCTTGCT GTTTGCATCC     660

GAATCGTGGT CTCGCTGTTC CTTGGGAGGG TCTCCTCTGA GTGATTGACT ACCCACGACG     720

GGGGTCTTTC ATTTGGGGGC TCGTCCGGGA TTTGGAGACC CCTGCCCAGG GACCACCGAC     780

CCACCACCGG GAGGTAAGCT GGCCAGCAAC TTATCTGTGT CTGTCCGATT GTCTAGTGTC     840

TATGTTTGAT GTTATGCGCC TGCGTCTGTA CTAGTTAGCT AACTAGCTCT GTATCTGGCG     900

GACCCGTGGT GGAACTGACG AGTTCTGAAC ACCCGGCCGC AACCCTGGGA GACGTCCCAG     960

GGACTTTGGG GGCCGTTTTT GTGGCCCGAC CTGAGGAAGG GAGTCGATGT GGAATCCGAC    1020
```

-continued

| | |
|---|---|
| CCCGTCAGGA TATGTGGTTC TGGTAGGAGA CGAGAACCTA AAACAGTTCC CGCCTCCGTC | 1080 |
| TGAATTTTTG CTTTCGGTTT GGAACCGAAG CCGCGCGTCT TGTCTGCTGC AGCGCTGCAG | 1140 |
| CATCGTTCTG TGTTGTCTCT GTCTGACTGT GTTTCTGTAT TTGTCTGAAA ATTAGGGCCA | 1200 |
| GACTGTTACC ACTCCCTTAA GTTTGACCTT AGGTCACTGG AAAGATGTCG AGCGGATCGC | 1260 |
| TCACAACCAG TCGGTAGATG TCAAGAAGAG ACGTTGGGTT ACCTTCTGCT CTGCAGAATG | 1320 |
| GCCAACCTTT AACGTCGGAT GGCCGCGAGA CGGCACCTTT AACCGAGACC TCATCACCCA | 1380 |
| GGTTAAGATC AAGGTCTTTT CACCTGGCCC GCATGGACAC CCAGACCAGG TCCCCTACAT | 1440 |
| CGTGACCTGG GAAGCCTTGG CTTTTGACCC CCCTCCCTGG GTCAAGCCCT TTGTACACCC | 1500 |
| TAAGCCTCCG CCTCCTCTTC CTCCATCCGC CCCGTCTCTC CCCCTTGAAC CTCCTCGTTC | 1560 |
| GACCCCGCCT CGATCCTCCC TTTATCCAGC CCTCACTCCT TCTCTAGGCG CCGGAATTCC | 1620 |
| GATCTGATCA AGAGACAGGA TGAGGATCGT TTCGCATGAT TGAACAAGAT GGATTGCACG | 1680 |
| CAGGTTCTCC GGCCGCTTGG GTGGAGAGGC TATTCGGCTA TGACTGGGCA CAACAGACAA | 1740 |
| TCGGCTGCTC TGATGCCGCC GTGTTCCGGC TGTCAGCGCA GGGGCGCCCG GTTCTTTTTG | 1800 |
| TCAAGACCGA CCTGTCCGGT GCCCTGAATG AACTGCAGGA CGAGGCAGCG CGGCTATCGT | 1860 |
| GGCTGGCCAC GACGGGCGTT CCTTGCGCAG CTGTGCTCGA CGTTGTCACT GAAGCGGGAA | 1920 |
| GGGACTGGCT GCTATTGGGC GAAGTGCCGG GGCAGGATCT CCTGTCATCT CACCTTGCTC | 1980 |
| CTGCCGAGAA AGTATCCATC ATGGCTGATG CAATGCGGCG GCTGCATACG CTTGATCCGG | 2040 |
| CTACCTGCCC ATTCGACCAC CAAGCGAAAC ATCGCATCGA GCGAGCACGT ACTCGGATGG | 2100 |
| AAGCCGGTCT TGTCGATCAG GATGATCTGG ACGAAGAGCA TCAGGGGCTC GCGCCAGCCG | 2160 |
| AACTGTTCGC CAGGCTCAAG GCGCGCATGC CCGACGGCGA GGATCTCGTC GTGACCCATG | 2220 |
| GCGATGCCTG CTTGCCGAAT ATCATGGTGG AAAATGGCCG CTTTTCTGGA TTCATCGACT | 2280 |
| GTGGCCGGCT GGGTGTGGCG GACCGCTATC AGGACATAGC GTTGGCTACC CGTGATATTG | 2340 |
| CTGAAGAGCT TGGCGGCGAA TGGGCTGACC GCTTCCTCGT GCTTTACGGT ATCGCCGCTC | 2400 |
| CCGATTCGCA GCGCATCGCC TTCTATCGCC TTCTTGACGA GTTCTTCTGA GCGGGACTCT | 2460 |
| GGGGTTCGAA ATGACCGACC AAGCGACGCC CAACCTGCCA TCACGAGATT TCGATTCCAC | 2520 |
| CGCCGCCTTC TATGAAAGGT TGGGCTTCGG AATCGTTTTC CGGGACGCCG GCTGGATGAT | 2580 |
| CCTCCAGCGC GGGGATCTCA TGCTGGAGTT CTTCGCCCAC CCCGGGCTCG ATCCCCTCGC | 2640 |
| GAGTTGGTTC AGCTGCTGCC TGAGGCTGGA CGACCTCGCG GAGTTCTACC GGCAGTGCAA | 2700 |
| ATCCGTCGGC ATCCAGGAAA CCAGCAGCGG CTATCCGCGC ATCCATGCCC CCGAACTGCA | 2760 |
| GGAGTGGGGA GGCACGATGG CCGCTTTGGT CGAGGCGGAT CCGCGGCCGC CTAGTTATTA | 2820 |
| ATAGTAATCA ATTACGGGGT CATTAGTTCA TAGCCCATAT ATGGAGTTCC GCGTTACATA | 2880 |
| ACTTACGGTA AATGGCCCGC CTGGCTGACC GCCCAACGAC CCCCGCCCAT TGACGTCAAT | 2940 |
| AATGACGTAT GTTCCCATAG TAACGCCAAT AGGGACTTTC CATTGACGTC AATGGGTGGA | 3000 |
| GTATTTACGG TAAACTGCCC ACTTGGCAGT ACATCAAGTG TATCATATGC CAAGTACGCC | 3060 |
| CCCTATTGAC GTCAATGACG GTAAATGGCC CGCCTGGCAT TATGCCCAGT ACATGACCTT | 3120 |
| ATGGGACTTT CCTACTTGGC AGTACATCTA CGTATTAGTC ATCGCTATTA CCATGGTGAT | 3180 |
| GCGGTTTTGG CAGTACATCA ATGGGCGTGG ATAGCGGTTT GACTCACGGG GATTTCCAAG | 3240 |
| TCTCCACCCC ATTGACGTCA ATGGGAGTTT GTTTTGGCAC CAAAATCAAC GGGACTTTCC | 3300 |
| AAAATGTCGT AACAACTCCG CCCCATTGAC GCAAATGGGC GGTAGGCGTG TACGGTGGGA | 3360 |
| GGTCTATATA AGCAGAGCTG GTTTAGTGAA CCGTCAGATC CGCTAGCGCT ACCGGTCGCC | 3420 |

-continued

```
ACCATGGTGA GCAAGGGCGA GGAGCTGTTC ACCGGGGTGG TGCCCATCCT GGTCGAGCTG      3480

GACGGCGACG TGAACGGCCA CAAGTTCAGC GTGTCCGGCG AGGGCGAGGG CGATGCCACC      3540

TACGGCAAGC TGACCCTGAA GTTCATCTGC ACCACCGGCA AGCTGCCCGT GCCCTGGCCC      3600

ACCCTCGTGA CCACCCTGAC CTACGGCGTG CAGTGCTTCA GCCGCTACCC CGACCACATG      3660

AAGCAGCACG ACGTCTTCAA GTCCGCCATG CCCGAAGGCT ACGTCCAGGA GCGCACCATC      3720

TTCTTCAAGG ACGACGGCAA CTACAAGACC CGCGCCGAGG TGAAGTTCGA GGGCGACACC      3780

CTGGTGAACC GCATCGAGCT GAAGGGCATC GACTTCAAGG AGGACGGCAA CATCCTGGGG      3840

CACAAGCTGG AGTACAACTA CAACAGCCAC AACGTCTATA TCATGGCCGA CAAGCAGAAG      3900

AACGGCATCA AGGTGAACTT CAAGATCCGC CACAACATCG AGGACGGCAG CGTGCAGCTC      3960

GCCGACCACT ACCAGCAGAA CACCCCCATC GGCGACGGCC CCGTGCTGCT GCCCGACAAC      4020

CACTACCTGA GCACCCAGTC CGCCCTGAGC AAAGACCCCA ACGAGAAGCG CGATCACATG      4080

GTCCTGCTGG AGTTCGTGAC CGCCGCCGGG ATCACTCACG GCATGGACGA GCTGTACAAG      4140

TAGCGGCCAA GCTTGTTAAC ATCGATAAAA TAAAAGATTT TATTTAGTCT CCAGAAAAAG      4200

GGGGGAATGA AAGACCCCAC CTGTAGGTTT GGCAAGCTAG CTTAAGTAAC GCCATTTTGC      4260

AAGGCATGGA AAAATACATA ACTGAGAATA GAGAAGTTCA GATCAAGGTC AGGAACAGAT      4320

GGAACAGCTG AATATGGGCC AAACAGGATA TCTGTGGTAA GCAGTTCCTG CCCCGGCTCA      4380

GGGCCAAGAA CAGATGGAAC AGCTGAATAT GGGCCAAACA GGATATCTGT GGTAAGCAGT      4440

TCCTGCCCCG GCTCAGGGCC AAGAACAGAT GGTCCCCAGA TGCGGTCCAG CCCTCAGCAG      4500

TTTCTAGAGA ACCATCAGAT GTTTCCAGGG TGCCCCAAGG ACCTGAAATG ACCCTGTGCC      4560

TTATTTGAAC TAACCAATCA GTTCGCTTCT CGCTTCTGTT CGCGCGCTTC TGCTCCCCGA      4620

GCTCAATAAA AGAGCCCACA ACCCCTCACT CGGGGCGCCA GTCCTCCGAT TGACTGAGTC      4680

GCCCGGGTAC CCGTGTATCC AATAAACCCT CTTGCAGTTG CATCCGACTT GTGGTCTCGC      4740

TGTTCCTTGG GAGGGTCTCC TCTGAGTGAT TGACTACCCG TCAGCGGGGG TCTTTCATTT      4800

GGGGGCTCGT CCGGGATCGG GAGACCCCTG CCCAGGGACC ACCGACCCAC CACCGGGAGG      4860

TAAGCTGGCT GCCTCGCGCG TTTCGGTGAT GACGGTGAAA ACCTCTGACA CATGCAGCTC      4920

CCGGAGACGG TCACAGCTTG TCTGTAAGCG GATGCCGGGA GCAGACAAGC CCGTCAGGGC      4980

GCGTCAGCGG GTGTTGGCGG GTGTCGGGGC GCAGCCATGA CCCAGTCACG TAGCGATAGC      5040

GGAGTGTATA CTGGCTTAAC TATGCGGCAT CAGAGCAGAT TGTACTGAGA GTGCACCATA      5100

TGCGGTGTGA AATACCGCAC AGATGCGTAA GGAGAAAATA CCGCATCAGG CGCTCTTCCG      5160

CTTCCTCGCT CACTGACTCG CTGCGCTCGG TCGTTCGGCT GCGGCGAGCG GTATCAGCTC      5220

ACTCAAAGGC GGTAATACGG TTATCCACAG AATCAGGGGA TAACGCAGGA AAGAACATGT      5280

GAGCAAAAGG CCAGCAAAAG GCCAGGAACC GTAAAAAGGC CGCGTTGCTG GCGTTTTTCC      5340

ATAGGCTCCG CCCCCCTGAC GAGCATCACA AAAATCGACG CTCAAGTCAG AGGTGGCGAA      5400

ACCCGACAGG ACTATAAAGA TACCAGGCGT TTCCCCCTGG AAGCTCCCTC GTGCGCTCTC      5460

CTGTTCCGAC CCTGCCGCTT ACCGGATACC TGTCCGCCTT TCTCCCTTCG GAAGCGTGG      5520

CGCTTTCTCA TAGCTCACGC TGTAGGTATC TCAGTTCGGT GTAGGTCGTT CGCTCCAAGC      5580

TGGGCTGTGT GCACGAACCC CCCGTTCAGC CCGACCGCTG CGCCTTATCC GGTAACTATC      5640

GTCTTGAGTC CAACCCGGTA AGACACGACT TATCGCCACT GGCAGCAGCC ACTGGTAACA      5700

GGATTAGCAG AGCGAGGTAT GTAGGCGGTG CTACAGAGTT CTTGAAGTGG TGGCCTAACT      5760
```

```
ACGGCTACAC TAGAAGGACA GTATTTGGTA TCTGCGCTCT GCTGAAGCCA GTTACCTTCG      5820

GAAAAAGAGT TGGTAGCTCT TGATCCGGCA ACAAACCAC CGCTGGTAGC GGTGGTTTTT       5880

TTGTTTGCAA GCAGCAGATT ACGCGCAGAA AAAAGGATC TCAAGAAGAT CCTTTGATCT       5940

TTTCTACGGG GTCTGACGCT CAGTGGAACG AAAACTCACG TTAAGGGATT TGGTCATGA       6000

GATTATCAAA AAGGATCTTC ACCTAGATCC TTTTAAATTA AAAATGAAGT TTTAAATCAA      6060

TCTAAAGTAT ATATGAGTAA ACTTGGTCTG ACAGTTACCA ATGCTTAATC AGTGAGGCAC      6120

CTATCTCAGC GATCTGTCTA TTTCGTTCAT CCATAGTTGC CTGACTCCCC GTCGTGTAGA      6180

TAACTACGAT ACGGGAGGGC TTACCATCTG GCCCCAGTGC TGCAATGATA CCGCGAGACC      6240

CACGCTCACC GGCTCCAGAT TTATCAGCAA TAAACCAGCC AGCCGGAAGG GCCGAGCGCA      6300

GAAGTGGTCC TGCAACTTTA TCCGCCTCCA TCCAGTCTAT TAATTGTTGC CGGGAAGCTA      6360

GAGTAAGTAG TTCGCCAGTT AATAGTTTGC GCAACGTTGT TGCCATTGCT GCAGGCATCG      6420

TGGTGTCACG CTCGTCGTTT GGTATGGCTT CATTCAGCTC CGGTTCCCAA CGATCAAGGC      6480

GAGTTACATG ATCCCCCATG TTGTGCAAAA AAGCGGTTAG CTCCTTCGGT CCTCCGATCG      6540

TTGTCAGAAG TAAGTTGGCC GCAGTGTTAT CACTCATGGT TATGGCAGCA CTGCATAATT      6600

CTCTTACTGT CATGCCATCC GTAAGATGCT TTTCTGTGAC TGGTGAGTAC TCAACCAAGT      6660

CATTCTGAGA ATAGTGTATG CGGCGACCGA GTTGCTCTTG CCCGGCGTCA ACACGGGATA      6720

ATACCGCGCC ACATAGCAGA ACTTTAAAAG TGCTCATCAT TGGAAAACGT TCTTCGGGGC      6780

GAAAACTCTC AAGGATCTTA CCGCTGTTGA GATCCAGTTC GATGTAACCC ACTCGTGCAC      6840

CCAACTGATC TTCAGCATCT TTTACTTTCA CCAGCGTTTC TGGGTGAGCA AAAACAGGAA      6900

GGCAAAATGC CGCAAAAAAG GGAATAAGGG CGACACGGAA ATGTTGAATA CTCATACTCT      6960

TCCTTTTTCA ATATTATTGA AGCATTTATC AGGGTTATTG TCTCATGAGC GGATACATAT      7020

TTGAATGTAT TTAGAAAAAT AAACAAATAG GGGTTCCGCG CACATTTCCC CGAAAAGTGC      7080

CACCTGACGT CTAAGAAACC ATTATTATCA TGACATTAAC CTATAAAAAT AGGCGTATCA      7140

CGAGGCCCTT TCGTCTTCAA                                                  7160

(2) INFORMATION FOR SEQ ID NO:6:

(i) SEQUENCE CHARACTERISTICS:
        (A) LENGTH: 7235 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:6:

GAATTGCTAG CAATTGCTAG CAATTGCTAG CAATTCATAC CAGATCACCG AAAACTGTCC       60

TCCAAATGTG TCCCCCTCAC ACTCCCAAAT TCGCGGGCTT CTGCCTCTTA GACCACTCTA      120

CCCTATTCCC CACACTCACC GGAGCCAAAG CCGCGGCCCT TCCGTTTCTT TGCTTTTGAA      180

AGACCCCACC CGTAGGTGGC AAGCTAGCTT AAGTAACGCC ACTTTGCAAG GCATGGAAAA      240

ATACATAACT GAGAATAGAA AAGTTCAGAT CAAGGTCAGG AACAAAGAAA CAGCTGAATA      300

CCAAACAGGA TATCTGTGGT AAGCGGTTCC TGCCCCGGCT CAGGGCCAAG AACAGATGAG      360

ACAGCTGAGT GATGGGCCAA ACAGGATATC TGTGGTAAGC AGTTCCTGCC CCGGCTCGGG      420
```

-continued

```
GCCAAGAACA GATGGTCCCC AGATGCGGTC CAGCCCTCAG CAGTTTCTAG TGAATCATCA      480

GATGTTTCCA GGGTGCCCCA AGGACCTGAA AATGACCCTG TACCTTATTT GAACTAACCA      540

ATCAGTTCGC TTCTCGCTTC TGTTCGCGCG CTTCCGCTCT CCGAGCTCAA TAAAAGAGCC      600

CACAACCCCT CACTCGGCGC GCCAGTCTTC CGATAGACTG CGTCGCCCGG GTACCCGTAT      660

TCCCAATAAA GCCTCTTGCT GTTTGCATCC GAATCGTGGT CTCGCTGTTC CTTGGGAGGG      720

TCTCCTCTGA GTGATTGACT ACCCACGACG GGGGTCTTTC ATTTGGGGGC TCGTCCGGGA      780

TTTGGAGACC CCTGCCCAGG GACCACCGAC CCACCACCGG GAGGTAAGCT GGCCAGCAAC      840

TTATCTGTGT CTGTCCGATT GTCTAGTGTC TATGTTTGAT GTTATGCGCC TGCGTCTGTA      900

CTAGTTAGCT AACTAGCTCT GTATCTGGCG GACCCGTGGT GGAACTGACG AGTTCTGAAC      960

ACCCGGCCGC AACCCTGGGA GACGTCCCAG GGACTTTGGG GGCCGTTTTT GTGGCCCGAC     1020

CTGAGGAAGG GAGTCGATGT GGAATCCGAC CCCGTCAGGA TATGTGGTTC TGGTAGGAGA     1080

CGAGAACCTA AAACAGTTCC CGCCTCCGTC TGAATTTTTG CTTTCGGTTT GGAACCGAAG     1140

CCGCGCGTCT TGTCTGCTGC AGCGCTGCAG CATCGTTCTG TGTTGTCTCT GTCTGACTGT     1200

GTTTCTGTAT TTGTCTGAAA ATTAGGGCCA GACTGTTACC ACTCCCTTAA GTTTGACCTT     1260

AGGTCACTGG AAAGATGTCG AGCGGATCGC TCACAACCAG TCGGTAGATG TCAAGAAGAG     1320

ACGTTGGGTT ACCTTCTGCT CTGCAGAATG GCCAACCTTT AACGTCGGAT GGCCGCGAGA     1380

CGGCACCTTT AACCGAGACC TCATCACCCA GGTTAAGATC AAGGTCTTTT CACCTGGCCC     1440

GCATGGACAC CCAGACCAGG TCCCCTACAT CGTGACCTGG GAAGCCTTGG CTTTTGACCC     1500

CCCTCCCTGG GTCAAGCCCT TTGTACACCC TAAGCCTCCG CCTCCTCTTC CTCCATCCGC     1560

CCCGTCTCTC CCCCTTGAAC CTCCTCGTTC GACCCCGCCT CGATCCTCCC TTTATCCAGC     1620

CCTCACTCCT TCTCTAGGCG CCGGAATTCG GCTTCCAAGC TTCGGCCAGC GCCTTGTAGA     1680

AGCGCGTATG GCTTCGTACC CCTGCCATCA ACACGCGTCT GCGTTCGACC AGGCTGCGCG     1740

TTCTCGCGGC CATAGCAACC GACGTACGGC GTTGCGCCCT CGCCGGCAGC AAGAAGCCAC     1800

GGAAGTCCGC CTGGAGCAGA AAATGCCCAC GCTACTGCGG GTTTATATAG ACGGTCCTCA     1860

CGGGATGGGG AAAACCACCA CCACGCAACT GCTGGTGGCC CTGGGTTCGC GCGACGATAT     1920

CGTCTACGTA CCCGAGCCGA TGACTTACTG GCGGGTGCTG GGGGCTTCCG AGACAATCGC     1980

GAACATCTAC ACCACACAAC ACCGCCTCGA CCAGGGTGAG ATATCGGCCG GGACGCGGC      2040

GGTGGTAATG ACAAGCGCCC AGATAACAAT GGGCATGCCT TATGCCGTGA CCGACGCCGT     2100

TCTGGCTCCT CATGTCGGGG GGGAGGCTGG GAGTTCACAT GCCCCGCCCC CGGCCCTCAC     2160

CCTCATCTTC GACCGCCATC CCATCGCCGC CCTCCTGTGC TACCCGGCCG CGCGATACCT     2220

TATGGGCAGC ATGACCCCCC AGGCCGTGCT GGCGTTCGTG GCCCTCATCC CGCCGACCTT     2280

GCCCGGCACA AACATCGTGT TGGGGCCCT TCCGGAGGAC AGACACATCG ACCGCCTGGC      2340

CAAACGCCAG CGCCCCGGCG AGCGGCTTGA CCTGGCTATG CTGGCCGCGA TTCGCCGCGT     2400

TTACGGGCTG CTTGCCAATA CGGTGCGGTA TCTGCAGGGC GGCGGGTCGT GGTGGGAGGA     2460

TTGGGGACAG CTTTCGGGGA CGGCCGTGCC GCCCCAGGGT GCCGAGCCCC AGAGCAACGC     2520

GGGCCCACGA CCCCATATCG GGACACGTT ATTTACCCTG TTTCGGGCCC CCGAGTTGCT      2580

GGCCCCCAAC GGCGACCTGT ATAACGTGTT TGCCTGGGCC TTGGACGTCT TGGCCAAACG     2640

CCTCCGTCCC ATGCACGTCT TTATCCTGGA TTACGACCAA TCGCCCGCCG GCTGCCGGGA     2700

CGCCCTGCTG CAACTTACCT CCGGGATGGT CCAGACCCAC GTCACCACCC CAGGCTCCAT     2760

ACCGACGATC TGCGACCTGG CGCGCACGTT TGCCCGGGAG ATGGGGGAGG CTAACTGAAA     2820
```

-continued

```
CACGGAAGGA GACAATACCG GAAGCTTGGA AGCCGAATTC GTTAACTCGA GGGATCCGCG    2880

GCCGCCTAGT TATTAATAGT AATCAATTAC GGGGTCATTA GTTCATAGCC CATATATGGA    2940

GTTCCGCGTT ACATAACTTA CGGTAAATGG CCCGCCTGGC TGACCGCCCA ACGACCCCCG    3000

CCCATTGACG TCAATAATGA CGTATGTTCC CATAGTAACG CCAATAGGGA CTTTCCATTG    3060

ACGTCAATGG GTGGAGTATT TACGGTAAAC TGCCCACTTG GCAGTACATC AAGTGTATCA    3120

TATGCCAAGT ACGCCCCCTA TTGACGTCAA TGACGGTAAA TGGCCCGCCT GGCATTATGC    3180

CCAGTACATG ACCTTATGGG ACTTTCCTAC TTGGCAGTAC ATCTACGTAT TAGTCATCGC    3240

TATTACCATG GTGATGCGGT TTTGGCAGTA CATCAATGGG CGTGGATAGC GGTTTGACTC    3300

ACGGGGATTT CCAAGTCTCC ACCCCATTGA CGTCAATGGG AGTTTGTTTT GGCACCAAAA    3360

TCAACGGGAC TTTCCAAAAT GTCGTAACAA CTCCGCCCCA TTGACGCAAA TGGGCGGTAG    3420

GCGTGTACGG TGGGAGGTCT ATATAAGCAG AGCTGGTTTA GTGAACCGTC AGATCCGCTA    3480

GCGCTACCGG TCGCCACCAT GGTGAGCAAG GGCGAGGAGC TGTTCACCGG GGTGGTGCCC    3540

ATCCTGGTCG AGCTGGACGG CGACGTGAAC GGCCACAAGT TCAGCGTGTC CGGCGAGGGC    3600

GAGGGCGATG CCACCTACGG CAAGCTGACC CTGAAGTTCA TCTGCACCAC CGGCAAGCTG    3660

CCCGTGCCCT GGCCCACCCT CGTGACCACC CTGACCTACG GCGTGCAGTG CTTCAGCCGC    3720

TACCCCGACC ACATGAAGCA GCACGACGTC TTCAAGTCCG CCATGCCCGA AGGCTACGTC    3780

CAGGAGCGCA CCATCTTCTT CAAGGACGAC GGCAACTACA AGACCCGCGC CGAGGTGAAG    3840

TTCGAGGGCG ACACCCTGGT GAACCGCATC GAGCTGAAGG GCATCGACTT CAAGGAGGAC    3900

GGCAACATCC TGGGGCACAA GCTGGAGTAC AACTACAACA GCCACAACGT CTATATCATG    3960

GCCGACAAGC AGAAGAACGG CATCAAGGTG AACTTCAAGA TCCGCCACAA CATCGAGGAC    4020

GGCAGCGTGC AGCTCGCCGA CCACTACCAG CAGAACACCC CCATCGGCGA CGGCCCCGTG    4080

CTGCTGCCCG ACAACCACTA CCTGAGCACC CAGTCCGCCC TGAGCAAAGA CCCCAACGAG    4140

AAGCGCGATC ACATGGTCCT GCTGGAGTTC GTGACCGCCG CCGGGATCAC TCACGGCATG    4200

GACGAGCTGT ACAAGTAGCG GCCAAGCTTG TTAACATCGA TAAAATAAAA GATTTTATTT    4260

AGTCTCCAGA AAAAGGGGGG AATGAAAGAC CCCACCTGTA GGTTTGGCAA GCTAGCTTAA    4320

GTAACGCCAT TTTGCAAGGC ATGGAAAAAT ACATAACTGA GAATAGAGAA GTTCAGATCA    4380

AGGTCAGGAA CAGATGGAAC AGCTGAATAT GGGCCAAACA GGATATCTGT GGTAAGCAGT    4440

TCCTGCCCCG GCTCAGGGCC AAGAACAGAT GGAACAGCTG AATATGGGCC AAACAGGATA    4500

TCTGTGGTAA GCAGTTCCTG CCCCGGCTCA GGGCCAAGAA CAGATGGTCC CCAGATGCGG    4560

TCCAGCCCTC AGCAGTTTCT AGAGAACCAT CAGATGTTTC CAGGGTGCCC CAAGGACCTG    4620

AAATGACCCT GTGCCTTATT TGAACTAACC AATCAGTTCG CTTCTCGCTT CTGTTCGCGC    4680

GCTTCTGCTC CCCGAGCTCA ATAAAAGAGC CCACAACCCC TCACTCGGGG CGCCAGTCCT    4740

CCGATTGACT GAGTCGCCCG GGTACCCGTG TATCCAATAA ACCCTCTTGC AGTTGCATCC    4800

GACTTGTGGT CTCGCTGTTC CTTGGGAGGG TCTCCTCTGA GTGATTGACT ACCCGTCAGC    4860

GGGGGTCTTT CATTTGGGGG CTCGTCCGGG ATCGGAGAC CCCTGCCCAG GGACCACCGA    4920

CCCACCACCG GGAGGTAAGC TGGCTGCCTC GCGCGTTTCG GTGATGACGG TGAAAACCTC    4980

TGACACATGC AGCTCCCGGA GACGGTCACA GCTTGTCTGT AAGCGGATGC CGGGAGCAGA    5040

CAAGCCCGTC AGGGCGCGTC AGCGGGTGTT GGCGGGTGTC GGGGCGCAGC CATGACCCAG    5100

TCACGTAGCG ATAGCGGAGT GTATACTGGC TTAACTATGC GGCATCAGAG CAGATTGTAC    5160
```

-continued

```
TGAGAGTGCA CCATATGCGG TGTGAAATAC CGCACAGATG CGTAAGGAGA AAATACCGCA    5220

TCAGGCGCTC TTCCGCTTCC TCGCTCACTG ACTCGCTGCG CTCGGTCGTT CGGCTGCGGC    5280

GAGCGGTATC AGCTCACTCA AAGGCGGTAA TACGGTTATC CACAGAATCA GGGGATAACG    5340

CAGGAAAGAA CATGTGAGCA AAAGGCCAGC AAAAGGCCAG GAACCGTAAA AAGGCCGCGT    5400

TGCTGGCGTT TTTCCATAGG CTCCGCCCCC CTGACGAGCA TCACAAAAAT CGACGCTCAA    5460

GTCAGAGGTG GCGAAACCCG ACAGGACTAT AAAGATACCA GGCGTTTCCC CCTGGAAGCT    5520

CCCTCGTGCG CTCTCCTGTT CCGACCCTGC CGCTTACCGG ATACCTGTCC GCCTTTCTCC    5580

CTTCGGGAAG CGTGGCGCTT TCTCATAGCT CACGCTGTAG GTATCTCAGT TCGGTGTAGG    5640

TCGTTCGCTC CAAGCTGGGC TGTGTGCACG AACCCCCCGT TCAGCCCGAC CGCTGCGCCT    5700

TATCCGGTAA CTATCGTCTT GAGTCCAACC CGGTAAGACA CGACTTATCG CCACTGGCAG    5760

CAGCCACTGG TAACAGGATT AGCAGAGCGA GGTATGTAGG CGGTGCTACA GAGTTCTTGA    5820

AGTGGTGGCC TAACTACGGC TACACTAGAA GGACAGTATT TGGTATCTGC GCTCTGCTGA    5880

AGCCAGTTAC CTTCGGAAAA AGAGTTGGTA GCTCTTGATC CGGCAAACAA ACCACCGCTG    5940

GTAGCGGTGG TTTTTTTGTT TGCAAGCAGC AGATTACGCG CAGAAAAAAA GGATCTCAAG    6000

AAGATCCTTT GATCTTTTCT ACGGGGTCTG ACGCTCAGTG GAACGAAAAC TCACGTTAAG    6060

GGATTTTGGT CATGAGATTA TCAAAAGGA TCTTCACCTA GATCCTTTTA AATTAAAAAT     6120

GAAGTTTTAA ATCAATCTAA AGTATATATG AGTAAACTTG GTCTGACAGT TACCAATGCT    6180

TAATCAGTGA GGCACCTATC TCAGCGATCT GTCTATTTCG TTCATCCATA GTTGCCTGAC    6240

TCCCCGTCGT GTAGATAACT ACGATACGGG AGGGCTTACC ATCTGGCCCC AGTGCTGCAA    6300

TGATACCGCG AGACCCACGC TCACCGGCTC CAGATTTATC AGCAATAAAC CAGCCAGCCG    6360

GAAGGGCCGA GCGCAGAAGT GGTCCTGCAA CTTTATCCGC CTCCATCCAG TCTATTAATT    6420

GTTGCCGGGA AGCTAGAGTA AGTAGTTCGC CAGTTAATAG TTTGCGCAAC GTTGTTGCCA    6480

TTGCTGCAGG CATCGTGGTG TCACGCTCGT CGTTTGGTAT GGCTTCATTC AGCTCCGGTT    6540

CCCAACGATC AAGGCGAGTT ACATGATCCC CCATGTTGTG CAAAAAAGCG GTTAGCTCCT    6600

TCGGTCCTCC GATCGTTGTC AGAAGTAAGT TGGCCGCAGT GTTATCACTC ATGGTTATGG    6660

CAGCACTGCA TAATTCTCTT ACTGTCATGC CATCCGTAAG ATGCTTTTCT GTGACTGGTG    6720

AGTACTCAAC CAAGTCATTC TGAGAATAGT GTATGCGGCG ACCGAGTTGC TCTTGCCCGG    6780

CGTCAACACG GGATAATACC GCGCCACATA GCAGAACTTT AAAAGTGCTC ATCATTGGAA    6840

AACGTTCTTC GGGGCGAAAA CTCTCAAGGA TCTTACCGCT GTTGAGATCC AGTTCGATGT    6900

AACCCACTCG TGCACCCAAC TGATCTTCAG CATCTTTTAC TTTCACCAGC GTTTCTGGGT    6960

GAGCAAAAAC AGGAAGGCAA AATGCCGCAA AAAAGGGAAT AAGGGCGACA CGGAAATGTT    7020

GAATACTCAT ACTCTTCCTT TTTCAATATT ATTGAAGCAT TTATCAGGGT TATTGTCTCA    7080

TGAGCGGATA CATATTTGAA TGTATTTAGA AAAATAAACA AATAGGGGTT CCGCGCACAT    7140

TTCCCCGAAA AGTGCCACCT GACGTCTAAG AAACCATTAT TATCATGACA TTAACCTATA    7200

AAAATAGGCG TATCACGAGG CCCTTTCGTC TTCAA                               7235
```

(2) INFORMATION FOR SEQ ID NO:7:

(i) SEQUENCE CHARACTERISTICS:
  (A) LENGTH: 36 base pairs
  (B) TYPE: nucleic acid
  (C) STRANDEDNESS: single
  (D) TOPOLOGY: linear

```
        (ii) MOLECULE TYPE: other nucleic acid
             (A) DESCRIPTION: /desc = "primer"

(iii) HYPOTHETICAL: NO (iv) ANTI-SENSE: NO (xi) SEQUENCE DESCRIPTION: SEQ ID NO:7:

GGGAAGCTTT TATTATTTGT ATAGTTCATC CATGCC                                36

(2) INFORMATION FOR SEQ ID NO:8:

(i) SEQUENCE CHARACTERISTICS:
             (A) LENGTH: 36 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(iii) HYPOTHETICAL: NO (iv) ANTI-SENSE: NO (xi) SEQUENCE DESCRIPTION: SEQ ID NO:8:

GGGAAGCTTG CGCGTATGGG TAAAGGAGAA GAACTT                                36

(2) INFORMATION FOR SEQ ID NO:9:

(i) SEQUENCE CHARACTERISTICS:
             (A) LENGTH: 54 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(iii) HYPOTHETICAL: NO (iv) ANTI-SENSE: NO (xi) SEQUENCE DESCRIPTION: SEQ ID NO:9:

GGATCTAGAG GATCCGCGGC CGCCTAGTTA TTAATAGTAA TCAATTACGG GGTC            54

(2) INFORMATION FOR SEQ ID NO:10:

(i) SEQUENCE CHARACTERISTICS:
             (A) LENGTH: 48 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(iii) HYPOTHETICAL: NO (iv) ANTI-SENSE: NO (xi) SEQUENCE DESCRIPTION: SEQ ID NO:10:

GGAAAGCTTC TATCATTATT GAGCTCGAGA TCTGAGTCCG GACTTGTA                   48
```